(12) United States Patent
Minami et al.

(10) Patent No.: US 12,265,157 B2
(45) Date of Patent: Apr. 1, 2025

(54) IMAGING DEVICE

(71) Applicant: Miraxia Edge Technology Corporation, Kyoto (JP)

(72) Inventors: Yuki Minami, Osaka (JP); Takuya Asano, Hyogo (JP); Takamasa Ando, Osaka (JP); Toshiya Fujii, Shiga (JP)

(73) Assignee: MIRAXIA EDGE TECHNOLOGY CORPORATION, Kyoto (JP)

( * ) Notice: Subject to any disclaimer, the term of this patent is extended or adjusted under 35 U.S.C. 154(b) by 966 days.

(21) Appl. No.: 17/344,692

(22) Filed: Jun. 10, 2021

(65) Prior Publication Data
US 2021/0302590 A1 Sep. 30, 2021

Related U.S. Application Data

(63) Continuation of application No. PCT/JP2019/043944, filed on Nov. 8, 2019.

(30) Foreign Application Priority Data

Dec. 14, 2018 (JP) ................................. 2018-234498

(51) Int. Cl.
*G01S 17/894* (2020.01)
*G01S 7/481* (2006.01)
(Continued)

(52) U.S. Cl.
CPC .......... *G01S 17/894* (2020.01); *G01S 7/4816* (2013.01); *G01S 7/4861* (2013.01); *G01S 7/4865* (2013.01); *G01S 7/497* (2013.01); *H04N 23/72* (2023.01)

(58) Field of Classification Search
CPC ........ G01S 7/894; G01S 7/4865; G01S 7/497; G01S 7/4861; G01S 7/4816; G01S 7/484;
(Continued)

(56) References Cited

U.S. PATENT DOCUMENTS 6,373,557 B1 4/2002 Mengel et al.
10,775,506 B2 * 9/2020 Hirasawa ................ G01S 17/10
(Continued)

FOREIGN PATENT DOCUMENTS

EP 3193190 A1 7/2017
JP 2002-500367 A 1/2002
(Continued)

OTHER PUBLICATIONS

International Search Report issued in corresponding International Patent Application No. PCT/JP2019/043944, dated Feb. 4, 2020, with English translation.

*Primary Examiner* — Daniel L Murphy
(74) *Attorney, Agent, or Firm* — Rimon P.C.

(57) ABSTRACT

An imaging device includes: a solid-state image sensor that is exposed to reflection light from an object and accumulates signal charges; and a control arithmetic device that controls irradiation by an infrared light source and exposure of the solid-state image sensor. The solid-state image sensor includes: photoelectric converters that convert the reflection light from the object into the signal charges; and charge accumulators that accumulate the signal charges. The imaging device performs, within one frame period, m types of exposure sequences (m is an integer greater than or equal to four) for controlling the irradiation and the exposure; assigns the charge accumulators exclusively to the m types of exposure sequences; accumulates, into the charge accumulators, the signal charges obtained from n (n is an integer greater than or equal to three) of the photoelectric converters in at least one type of exposure sequence among the m types of exposure sequences.

20 Claims, 34 Drawing Sheets

(51) Int. Cl.
*G01S 7/4861* (2020.01)
*G01S 7/4865* (2020.01)
*G01S 7/497* (2006.01)
*H04N 23/72* (2023.01)

(58) Field of Classification Search
CPC ..... G01S 7/4863; G01S 17/10; H04N 5/2352; H04N 23/72; H04N 23/73; H04N 23/74; H04N 25/71; A61B 5/026; G01C 3/06
USPC ........................................................ 356/5.01
See application file for complete search history.

(56) References Cited

U.S. PATENT DOCUMENTS

| | | |
|---|---|---|
| 2010/0231774 A1 | 9/2010 | Tashiro |
| 2015/0092019 A1 | 4/2015 | Asano et al. |
| 2016/0320486 A1 | 11/2016 | Murai et al. |
| 2017/0307359 A1 | 10/2017 | Yates |
| 2018/0176496 A1 | 6/2018 | Nakamura et al. |
| 2019/0007592 A1 | 1/2019 | Otani et al. |
| 2019/0025414 A1 | 1/2019 | Van Der Tempel et al. |
| 2019/0280030 A1 | 9/2019 | Kuwahara et al. |

FOREIGN PATENT DOCUMENTS

| | | |
|---|---|---|
| JP | 2010-213231 A | 9/2010 |
| JP | 6008148 B2 | 10/2016 |
| JP | 2018-96988 A | 6/2018 |
| WO | 2014/002415 A1 | 1/2014 |
| WO | 2015/107869 A1 | 7/2015 |
| WO | 2017/150246 A1 | 9/2017 |
| WO | 2018/101049 A1 | 6/2018 |

* cited by examiner

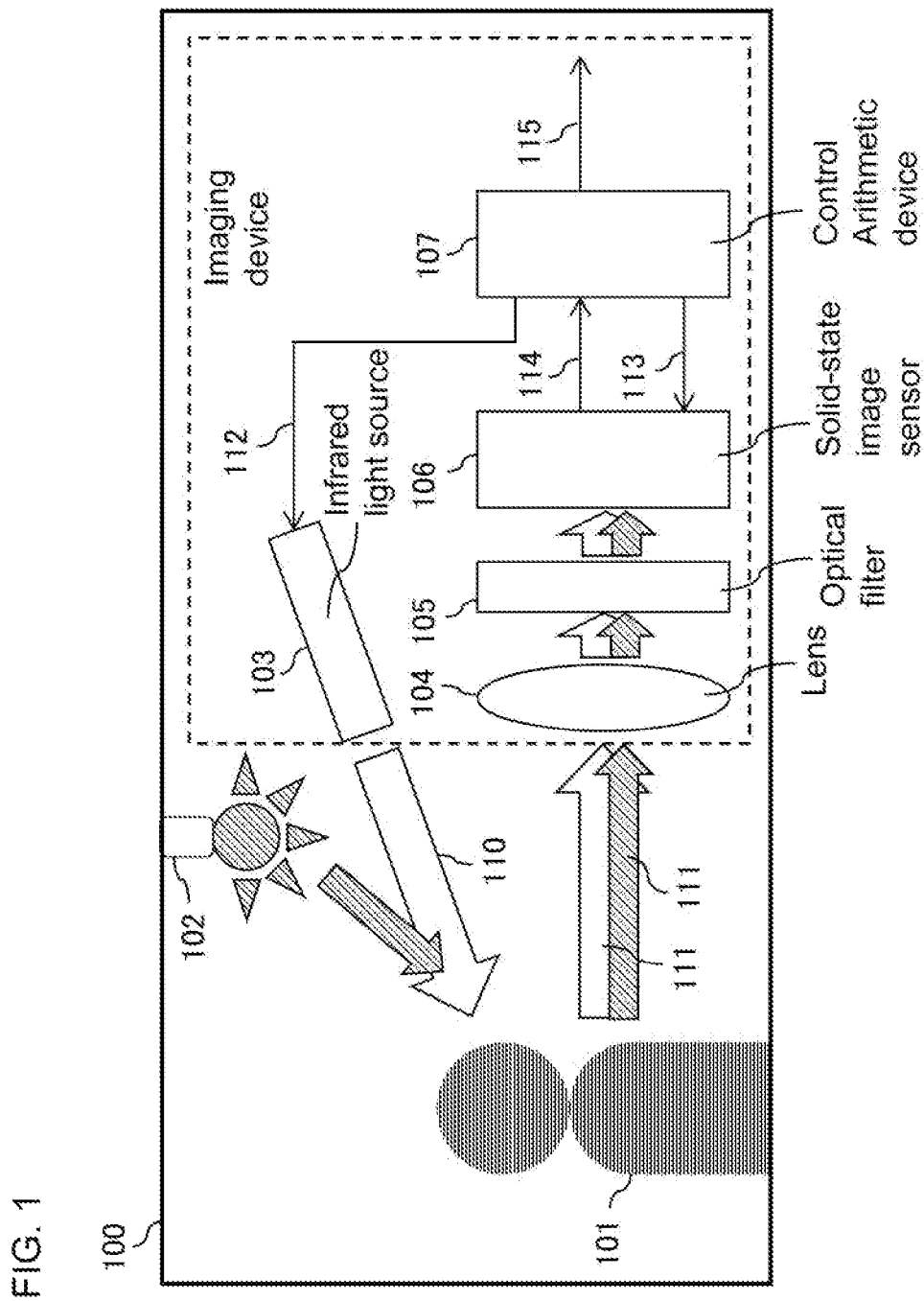

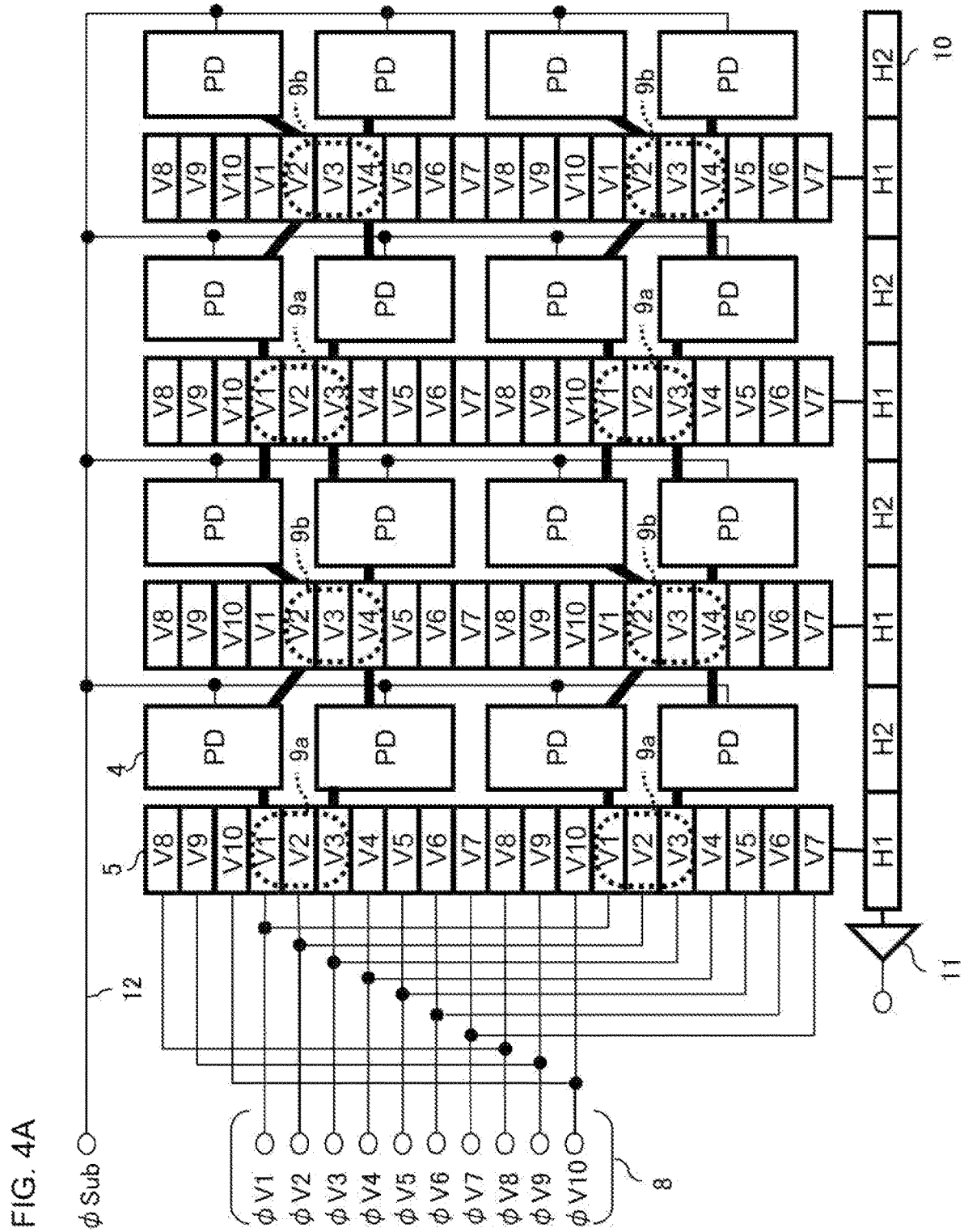

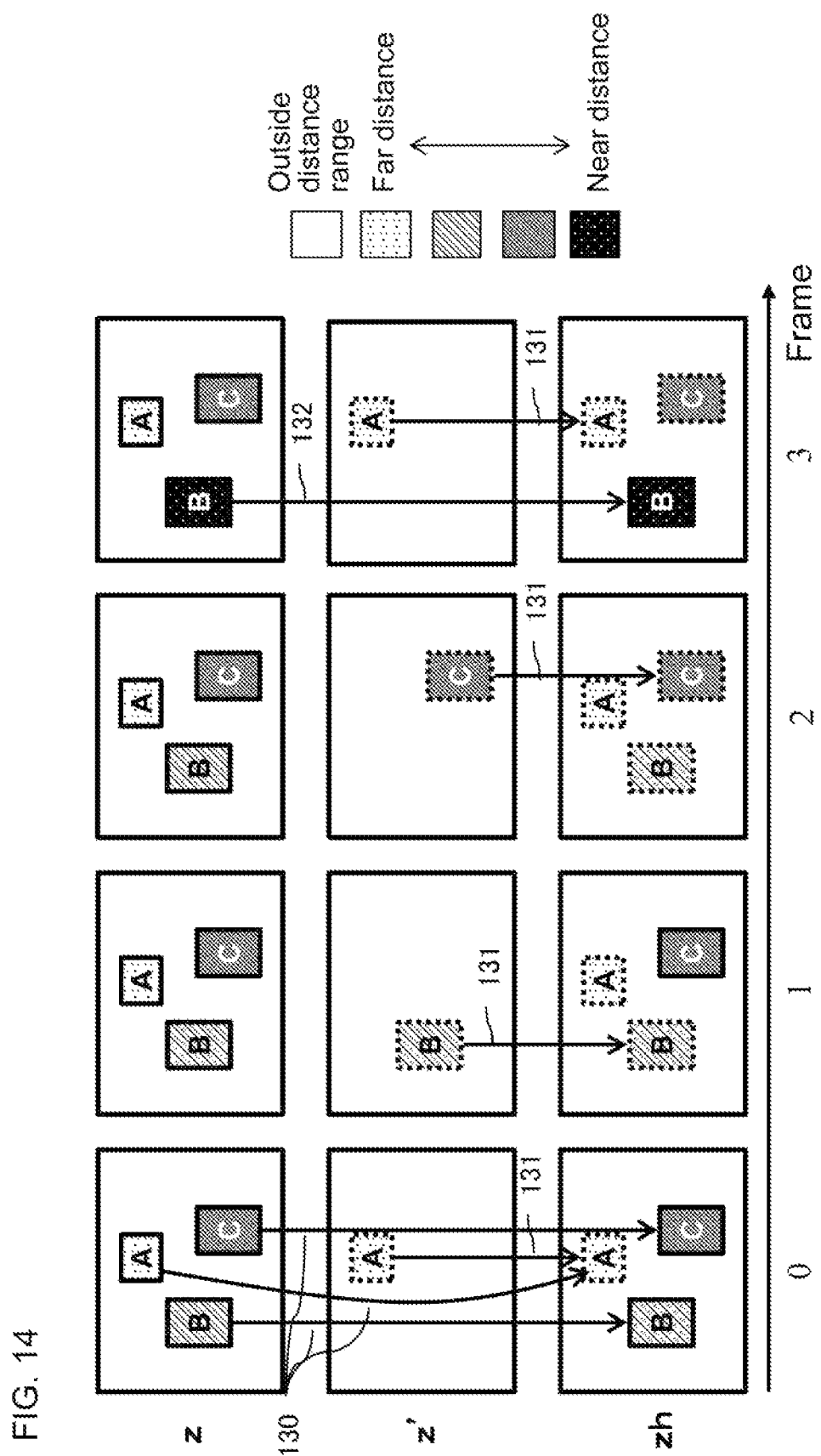

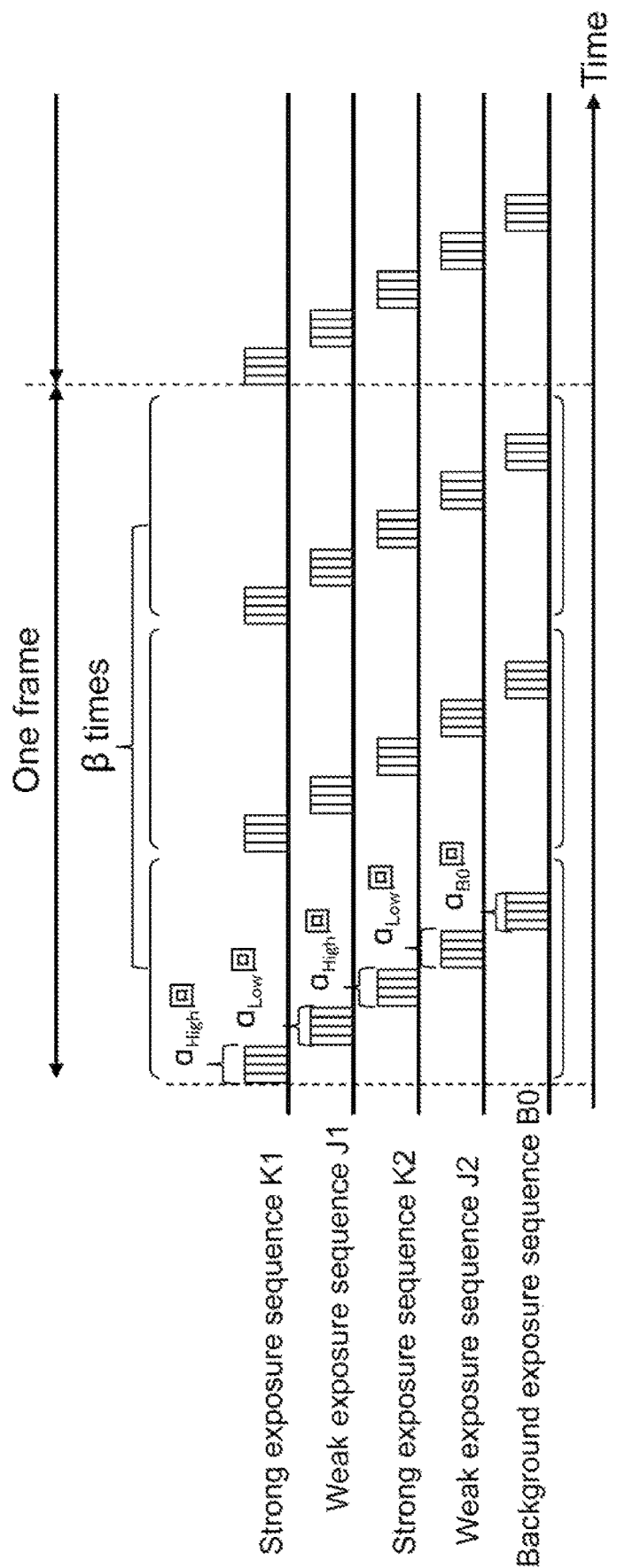

IMAGING DEVICE

CROSS REFERENCE TO RELATED APPLICATIONS

This is a continuation application of PCT International Application No. PCT/JP2019/043944 filed on Nov. 8, 2019, designating the United States of America, which is based on and claims priority of Japanese Patent Application No. 2018-234498 filed on Dec. 14, 2018. The entire disclosures of the above-identified applications, including the specifications, drawings and claims are incorporated herein by reference in their entirety.

FIELD

The present disclosure relates to an imaging device that irradiates an object with light from a light source, converts reflection light to an electric signal, and outputs the resulting electric signal.

BACKGROUND

A time of flight (TOF) technique is used to detect a physical object, such as an obstruction. In the TOF technique, the distance between a light source and an object is measured by use of the time of flight it takes for light to travel between the light source and the object. For example, according to Patent Literature 1, an object is irradiated with a pulsed light, and reflection light from the object is measured in two different periods. Then, the distance to the object is calculated based on the ratio of these reflection light. Moreover, according to one technique used in the field of biometry and material analysis, an object is irradiated with light, and the information on the inside of the object is acquired contactlessly based on the information on the light that has been diffusedly reflected inside the object. For example, according to Patent Literature 2, an object is irradiated with a pulsed light, and reflection light from the object is measured in each of a period in which the amount of reflection light increases and a period in which the amount of reflection light decreases. Thus, the information on the inside of the object at its shallow part and its deep part is acquired.

Typically, in the two techniques described above, the reflection light is measured by use of an image sensor, and the image sensor is exposed only for period $\Delta t$ in which the measurement is to be carried out. In other words, the reflection light is converted to signal charges by photoelectric converters (photodiodes (PDs)) disposed in a matrix, and the resultant signal charges are accumulated in a charge accumulator. In this example, the charge accumulator is implemented by a vertical transferrer (a vertical charge coupled device (VCCD)) in a case where the charge accumulator is a CCD image sensor or by a floating diffusion (FD) capacitance in a case where the charge accumulator is a metal oxide semiconductor (MOS) image sensor. In the above example, period $\Delta t$ determines moving distance $z=c\times\Delta t$ of the light needed for the measurement (c represents the speed of light) and is required to be a short period of from several picoseconds to ten-odd nanoseconds as this period $\Delta t$ affects the accuracy in measuring the distance and the accuracy in separating between the information on the object at its shallow part and the information on the object at its deep part in the two techniques described above. Accordingly, in order to obtain signal charges that are sufficient for the measurement, a set of the irradiation with the pulsed light and the exposure of the pulsed light needs to be repeated a plurality of times within one frame period, and the signal charges need to be accumulated. Moreover, when the reflection light is measured in a plurality of different periods, this requires a charge accumulator that is sufficient to independently accumulate the signal charges needed for each measurement.

CITATION LIST

Patent Literature

PTL 1: Japanese Unexamined Patent Application Publication (Translation of PCT Application) No. 2002-500367
PTL 2: Japanese Patent No. 6008148
PTL 3: Japanese Unexamined Patent Application Publication No. 2018-96988

SUMMARY

Technical Problem

In using the two techniques described above, there may be a case where an additional measurement is to be performed with the period for which the reflection light is measured or other conditions modified. For example, when an influence of light (background light) that enters an image sensor irrespective of the irradiation with a pulsed light is to be canceled, a measurement is carried out without the irradiation of a pulsed light, and the result obtained in this measurement may be subtracted from the result of measurement carried out with the irradiation of a pulsed light. Moreover, in some other conceivable cases, more accurate information may be acquired by dividing more finely the period in which the measurement is carried out, or a measurement suitable to the characteristics of an object to be measured may be carried out by changing the intensity or the wavelength of a pulsed light. However, when the period in which or the condition under which the measurement is carried out is modified as described above, this results in an increase in the mechanisms for independently accumulating the signal charges needed for each measurement or results in a decrease in the numerical aperture, and in turn the signal charges that are output from the photoelectric converters are reduced. In addition, the aforementioned modification requires the exposure to be performed with one frame period being divided into a plurality of periods or divided according to a plurality of conditions, and this generally reduces the signal charges greatly in each measurement. Accordingly, this poses a problem in that the accuracy of the information calculated from these signal charges is also reduced greatly.

According to Patent Literature 3, which addresses these issues, signal charges that are output from two photoelectric converters adjacent to each other in the vertical direction or in the horizontal direction are added and accumulated in a vertical transferrer. Thus, the number of phases of the vertical transferrer required per photoelectric converter is saved, and the amount of signal charges accumulated in each divided exposure is increased. Moreover, the combination of the photoelectric converters from which the electric charges are obtained and added is changed between the odd number rows and the even number rows or between the even number columns and the odd number columns, and thus any decrease in the spatial resolution associated with the addition of the signal charges is mitigated. However, when there are four or more types of periods in which or conditions under which the measurement is carried out, the amount of signal charges becomes insufficient.

The present disclosure is directed to providing an imaging device that can accumulate a sufficient amount of signal charges even when there are four or more types of periods in which or conditions under which a measurement is carried out and calculate the distance to an object or the information on the inside of the object with high accuracy.

Solution to Problem

To address the above, an imaging device according to one aspect of the present disclosure includes: a light source that irradiates an object with light; a solid-state image sensor that is exposed to reflection light from the object and accumulates the reflection light as a signal charge; and a controller that controls irradiation by the light source and exposure of the solid-state image sensor, wherein the solid-state image sensor includes: a plurality of photoelectric converters that convert the reflection light from the object into signal charges that are each the signal charge, and a plurality of charge accumulators that accumulate the signal charges, and the imaging device: performs, within one frame period, m types of exposure sequences (m is an integer greater than or equal to four) for controlling the irradiation and the exposure, assigns the plurality of charge accumulators exclusively to the m types of exposure sequences, and accumulates, into the plurality of charge accumulators, the signal charges obtained from n photoelectric converters (n is an integer greater than or equal to three) among the plurality of photoelectric converters in at least one type of exposure sequence among the m types of exposure sequences.

Advantageous Effects

The present disclosure can provide an imaging device that calculates the distance to an object or the information on the inside of the object with high accuracy.

BRIEF DESCRIPTION OF DRAWINGS

These and other advantages and features will become apparent from the following description thereof taken in conjunction with the accompanying Drawings, by way of non-limiting examples of embodiments disclosed herein.

FIG. 1 is a diagram showing a schematic configuration of a time of flight (TOF) imaging device according to Embodiment 1, 2 or 3.

FIG. 4A is a diagram showing a configuration example of a solid-state image sensor according to Embodiment 1, 2, 3, or 4.

FIG. 14 is an illustration for describing an operation of a distance corrector according to Embodiment 2.

FIG. 17 is an illustration for describing an operation timing of the imaging device according to Embodiment 3.

DESCRIPTION OF EMBODIMENTS

Figure 2A:
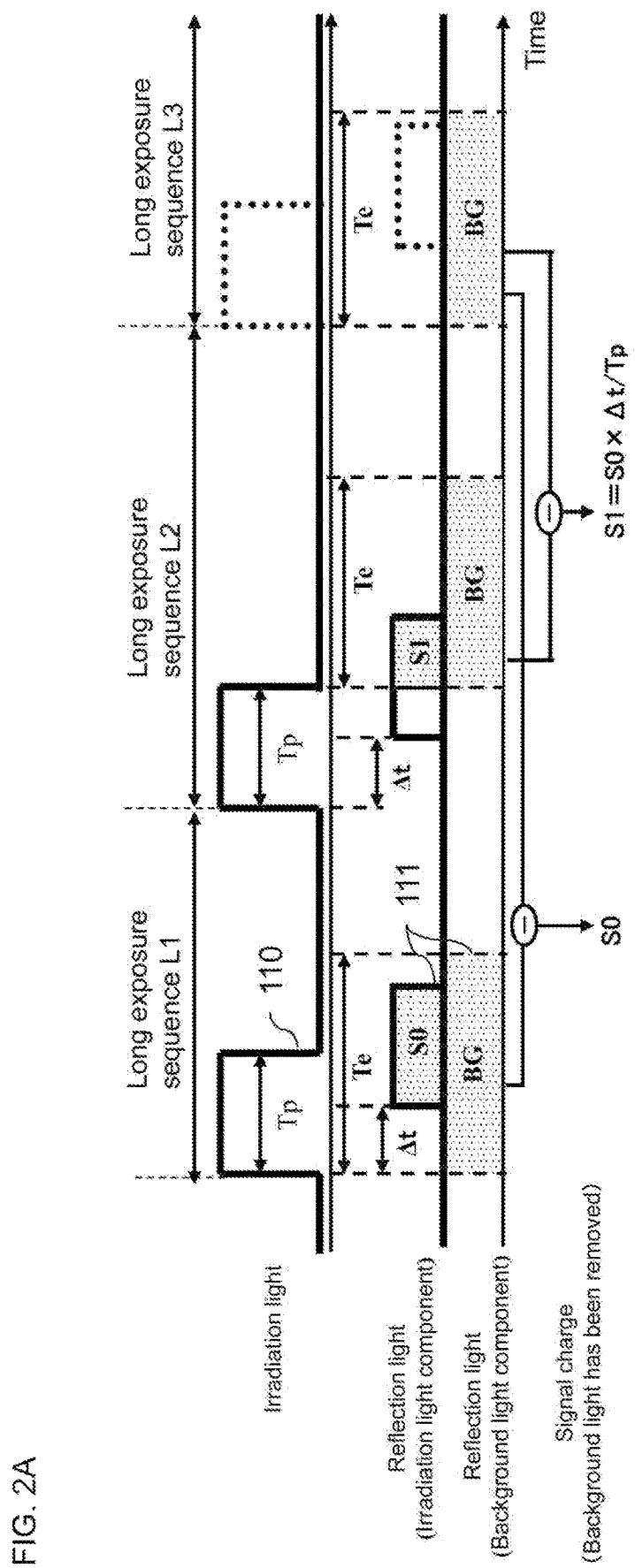
FIG. 2A is an illustration for describing an operation timing example and an operation principle of the imaging device according to Embodiment 1 or 2.

Hereinafter, some embodiments of the present disclosure will be described with reference to the drawings. Although the following description makes reference to the appended drawings, this is merely for the purpose of providing examples, and the present disclosure should not be limited by the description and the appended drawings.

In the drawings, elements indicating substantially identical configurations, operations, and effects are given identical reference characters.

Embodiment 1

Described in Embodiment 1 is an imaging device that can accumulate a sufficient amount of signal charges even when there are four or more types of periods in which or conditions under which a measurement is carried out and that can calculate the distance to an object with high accuracy. Specifically, described is a configuration example of an imaging device that can expand the distance range in which the range finding can be carried out by use of a long exposure period and a short exposure period and that can improve the accuracy of the measurement in a broad distance range spanning from a close distance to a far distance.

FIG. 1 is a diagram showing schematically a configuration of a time of flight (TOF) range finding device according to Embodiment 1, 2, or 3 and any element surrounding the range finding device. As shown in FIG. 1, in shooting space 100 with background light illumination 102, object 101 is irradiated with pulsed irradiation light 110 having a wavelength of 850 nm or 940 nm emitted from infrared light source 103. Reflection light 111 of irradiation light 110 reflected off object 101 is received by solid-state image sensor 106 via optical lens 104 and optical filter 105. Solid-state image sensor 106 is, for example, a CCD image sensor. Optical filter 105 transmits light in a near-infrared wavelength range of around 850 nm or 940 nm. An image formed by solid-state image sensor 106 is converted to a signal charge (this operation is referred to below as an exposure), and solid-state image sensor 106 outputs signal charge amount 114 to control arithmetic device 107. Control arithmetic device 107 performs control 112 of controlling the irradiation timing of infrared light source 103 and control 113 of controlling the exposure timing of solid-state image sensor 106. Thus, control arithmetic device 107 obtains six types of signal charge amounts 114 from solid-state image sensor 106, calculates two types of distances to object 101, and outputs the calculated distances in the form of distance signal 115. Infrared light source 103, optical lens 104, optical filter 105, solid-state image sensor 106, and control arithmetic device 107 constitute the range finding device. In this example, control arithmetic device 107 is implemented by a combination of a central processing unit (CPU), a field programmable gate array (FPGA), a digital signal processor (DPS), an analog front end (AFE), and so on, for example.

In FIG. 1, infrared light source 103 irradiates an object with light. Solid-state image sensor 106 is exposed to reflection light from the object and accumulates the reflection light in the form of a signal charge. Control arithmetic device 107 controls the irradiation by infrared light source 103 and the exposure of solid-state image sensor 106.

In the following, solid-state image sensor 106 and control arithmetic device 107 will be described further.

FIG. 4A is a configuration diagram of solid-state image sensor 106 according to the present embodiment. In FIG. 4A, only four pixels in the vertical direction and only four pixels in the horizontal direction are depicted for the sake of simplifying the drawing. Solid-state image sensor 106 includes a plurality of photoelectric converters (photodiodes) 4, vertical transferrers 5, horizontal transferrer 10, and charge detector 11. The plurality of photoelectric converters 4 are disposed in a matrix on a semiconductor substrate, and each photoelectric converter 4 converts reflection light 111 from object 101 into a signal charge. Vertical transferrers 5 each accumulate signal charges read out from corresponding photoelectric converters 4 and transfer the signal charges in the row direction (in the vertical direction). Horizontal transferrer 10 transfers the signal charges that have been transferred by vertical transferrers 5 into the column direction (in the horizontal direction). Charge detector 11 outputs the signal charges transferred by horizontal transferrer 10.

Solid-state image sensor 106 includes the plurality of photoelectric converters 4, which each convert reflection light from an object into a signal charge, and a plurality of charge accumulators that each accumulate signal charges. In the configuration example shown in FIG. 4A, the plurality of charge accumulators are implemented by signal packets formed as potential wells in vertical transferrers 5.

Control arithmetic device 107 performs m types of exposure sequences (m is an integer greater than or equal to four) within one frame period in order to control the irradiation and the exposure. In this case, control arithmetic device 107 assigns the charge accumulators exclusively to the m types of exposure sequences. In at least one type of exposure sequence among the m types of exposure sequences, control arithmetic device 107 accumulates the signal charges obtained from n photoelectric converters (n is an integer greater than or equal to three) into the charge accumulators.

In this example, solid-state image sensor 106 is an interline transfer CCD. For example, vertical transferrers 5 are each a ten-phase drive system with ten gates of vertical transfer electrodes 8 per two photoelectric converters 4 that are adjacent in the vertical direction, and horizontal transferrer 10 is a two-phase drive system. Of vertical transfer electrodes 8, φV1 and φV3 serve also as readout electrodes for four photoelectric converters 4 connected to corresponding vertical transferrer 5 in the odd number columns, and φV2 and φV4 serve also as readout electrodes for four photoelectric converters 4 connected to corresponding vertical transferrer 5 in the even number columns. With this configuration, the signal charges accumulated in four photoelectric converters 4 are added and read out to the position indicated, for example, by corresponding signal packet 9a of each vertical transferrer 5 in the odd number columns when a high voltage is being applied to φV1 and φV3 or added and read out to the position indicated, for example, by corresponding signal packet 9b of each vertical transferrer 5 in the even number columns when a high voltage is being applied to φV2 and φV4. Thereafter, the signal charges in vertical transferrers 5 are transferred in the column direction upon a voltage being applied to vertical transfer electrodes 8.

Photoelectric converters 4 are provided with vertical overflow drain (VOD) 12 for sweeping the signal charges. Although VOD 12 is depicted in the lateral direction of the pixels in order to facilitate the understanding of the present disclosure, VOD 12 extends in the bulk direction of the pixels (in the depthwise direction of the semiconductor substrate) in reality. Upon a high voltage being applied to electrode φSub connected to the substrate of VOD 12, the signal charges in all photoelectric converters 4 are discharged at once to the substrate.

With the configuration described above, solid-state image sensor 106 adds the signal charges accumulated in four photoelectric converters 4 and allocates and accumulates the added signal charges into vertical transferrers 5 in the odd number columns or vertical transferrers 5 in the even number columns. Thus, the types of the signal charges that solid-state image sensor 106 can accumulate while retaining its sensitivity becomes double the types of the signal charges that the solid-state image sensor disclosed in Patent Literature 3 can accumulate. In this example, vertical transferrers 5 are each a ten-phase drive system. Therefore, provided that a signal charge is accumulated in at a minimum of two phases, three types of signal charges can be accumulated in each vertical transferrer 5 in the odd number columns, and another three types of signal charges can be accumulated in each vertical transferrer 5 in the even number columns. Therefore, a total of six types of signal charges can be accumulated.

Figure 4B:
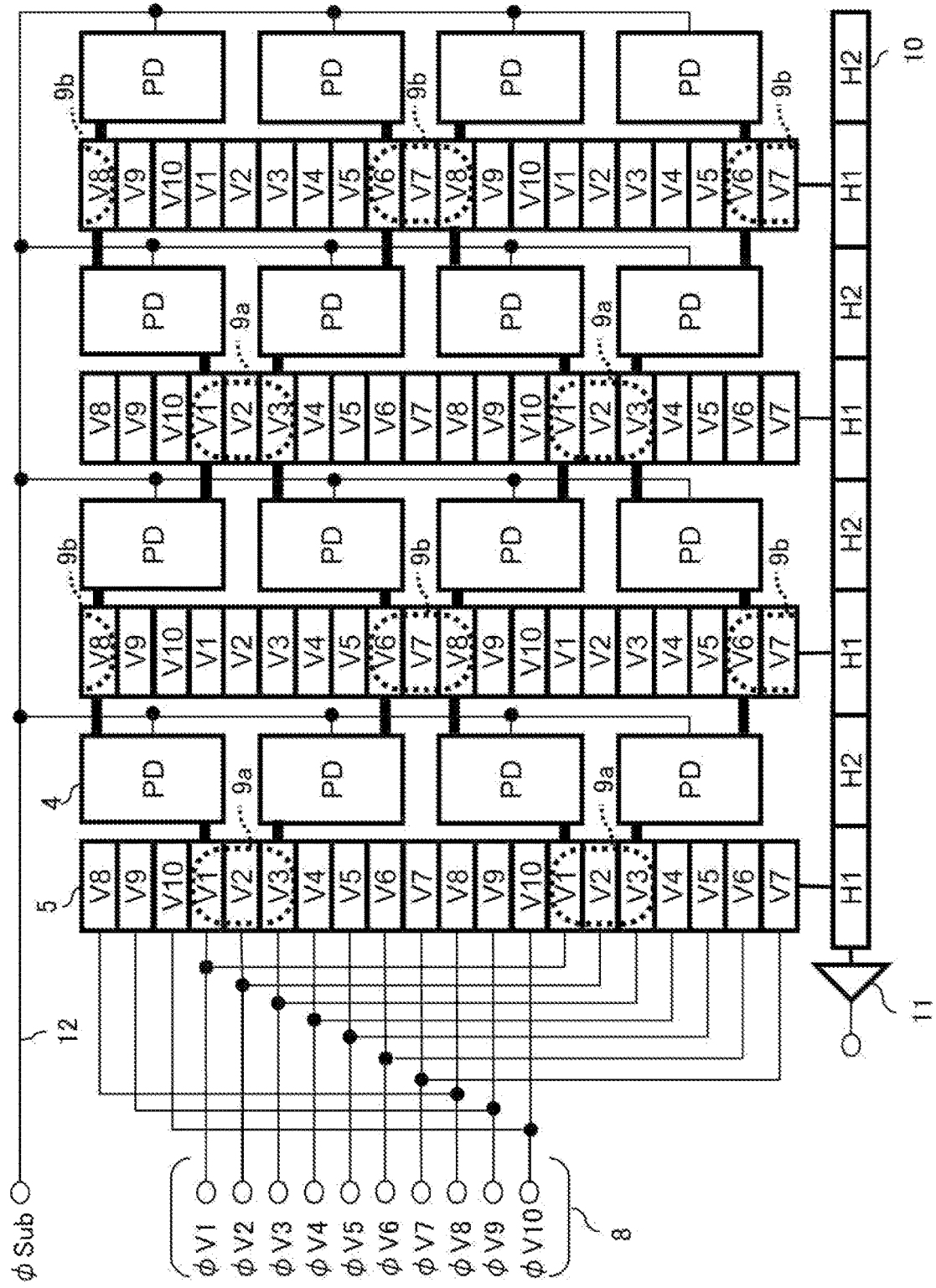
FIG. 4B is a diagram showing another configuration example of the solid-state image sensor according to Embodiment 1, 2, 3, or 4.

In this example, as shown in FIG. 4B, vertical transferrers 5 may be disposed such that photoelectric converters 4 that read out their signal charges into vertical transferrers 5 in the odd number columns and photoelectric converters 4 that read out their signal charges into vertical transferrers 5 in the even number columns are not level with each other in the column direction. In this case, an interpolation process may be performed by use of the signal charges accumulated in vertical transferrers 5 in the odd number columns and the signal charges accumulated in vertical transferrers 5 in the even number columns. Then, an improvement in the spatial resolution in the vertical direction can be expected, as compared to the configuration shown in FIG. 4A.

Moreover, the number of photoelectric converters 4 from which the signal charges are read out to be added may be increased to, for example, six or so, and the sensitivity may thus be further improved. However, there may be a trade-off between the improvement in the sensitivity and the decrease in the spatial resolution.

Figure 2B:
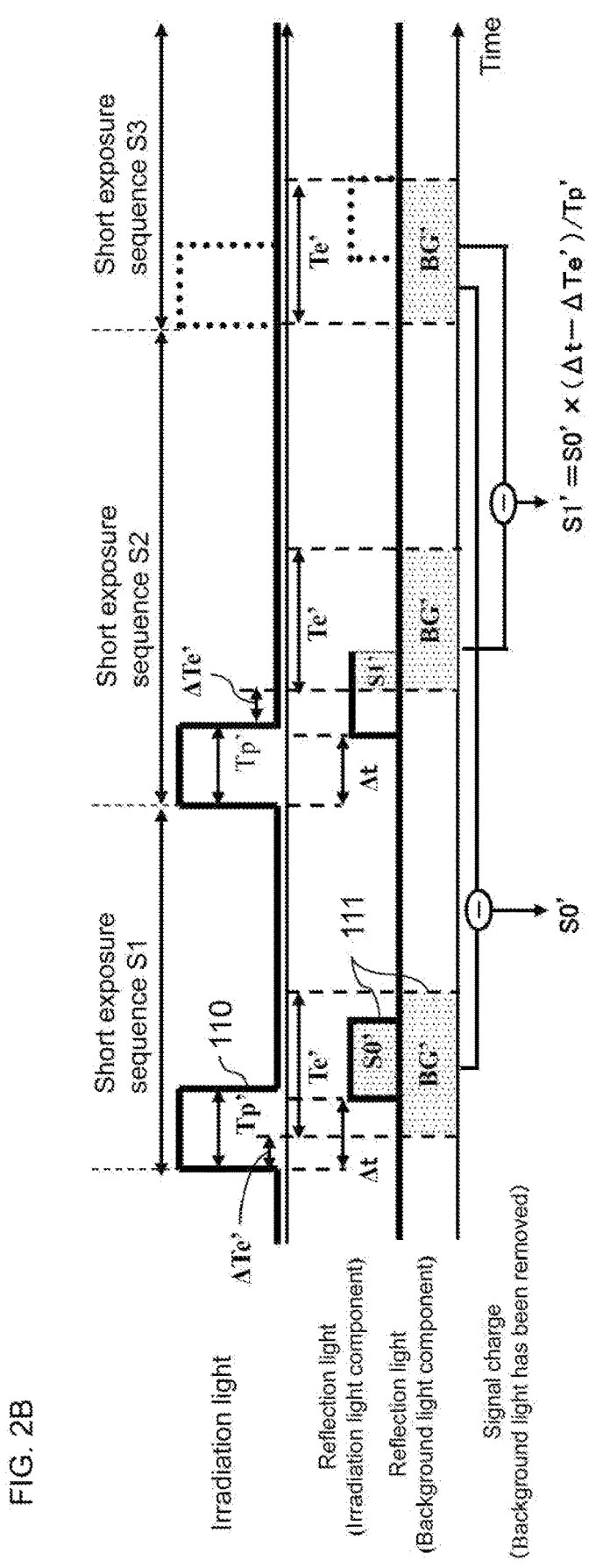
FIG. 2B is an illustration for describing another operation timing example and an operation principle of the imaging device according to Embodiment 1 or 2.
Figure 2C:
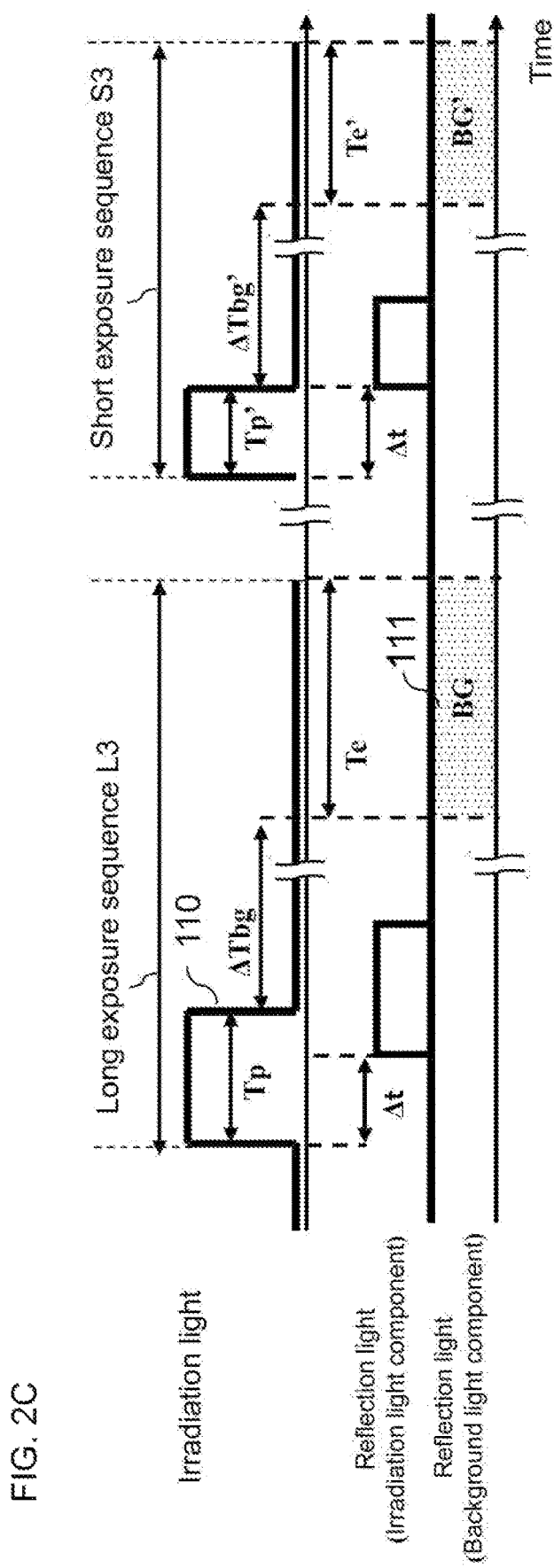
FIG. 2C is an illustration for describing yet another operation timing example and an operation principle of the imaging device according to Embodiment 1 or 2.

FIGS. 2A to 2C are illustrations for describing an operation timing and an operation principle of the range finding device according to the present embodiment. As shown in FIGS. 2A and 2B, an operation of the range finding device includes a total of six types of exposure sequences, namely long exposure sequences L1 to L3 and short exposure sequences S1 to S3. These exposure sequences are implemented as control arithmetic device 107 performs control 112 of controlling the irradiation timing of infrared light source 103 and control 113 of controlling the exposure timing of solid-state image sensor 106, and one type of signal charge is obtained in each of the exposure sequences. In this example, the pulse duration (the irradiation time) of irradiation light 110 is denoted by Tp and Tp' that is shorter than Tp, the delay between irradiation light 110 and reflection light 111 is denoted by Δt, and the length of the exposure period is denoted by Te and Te' that is shorter than Te.

First, as shown in FIG. 2A, in long exposure sequence L1, control arithmetic device 107 performs control 112 of controlling the irradiation timing and control 113 of controlling the exposure timing such that the exposure period starts at the rise of irradiation light 110 and includes the fall of reflection light 111. Thus, control arithmetic device 107 obtains signal charge S0+BG that is based on reflection light 111. Next, in long exposure sequence L2, control arithmetic device 107 performs control 112 of controlling the irradiation timing and control 113 of controlling the exposure timing such that the exposure period starts at the fall of irradiation light 110. Thus, control arithmetic device 107 obtains signal charge S1+BG that is based on reflection light 111. Moreover, in long exposure sequence L3, control arithmetic device 107 performs control 112 of controlling the irradiation timing and control 113 of controlling the exposure timing such that only the exposure is carried out without the irradiation of irradiation light 110. Thus, control arithmetic device 107 obtains signal charge BG that is based on reflection light 111. Thereafter, control arithmetic device 107 extracts signal charges S0 and S1 that are not dependent on the background light by subtracting BG from each of S0+BG and S1+BG.

In a similar manner, as shown in FIG. 2B, in short exposure sequence S1, control arithmetic device 107 performs control 112 of controlling the irradiation timing and control 113 of controlling the exposure timing such that the exposure period starts at a point that is ΔTe' past the rise of irradiation light 110 and includes the fall of reflection light 111. Thus, control arithmetic device 107 obtains signal charge S0'+BG' that is based on reflection light 111. Next, in short exposure sequence S2, control arithmetic device 107 performs control 112 of controlling the irradiation timing and control 113 of controlling the exposure timing such that the exposure period starts at a point that is ΔTe' past the fall of irradiation light 110. Thus, control arithmetic device 107 obtains signal charge S1'+BG' that is based on reflection light 111. Moreover, in short exposure sequence S3, control arithmetic device 107 performs control 112 of controlling the irradiation timing and control 113 of controlling the exposure timing such that only the exposure is carried out without the irradiation of irradiation light 110. Thus, control arithmetic device 107 obtains signal charge BG' that is based on reflection light 111. Thereafter, control arithmetic device 107 extracts signal charges S0' and S1' that are not dependent on the background light by subtracting BG' from each of S0'+BG' and S1'+BG'.

In this example, the irradiation of irradiation light 110 is not performed in long exposure sequence L3 and in short exposure sequence S3, as shown in FIGS. 2A and 2B. Alternatively, as shown in FIG. 2C, the irradiation of irradiation light 110 may be performed, and the starting time of the exposure period may be delayed by time ΔTbg and time ΔTbg' in which the irradiation light component included in reflection light 111 is attenuated to a negligible level. Thus, solid-state image sensor 106 may be exposed only to the background light component.

Figure 3:
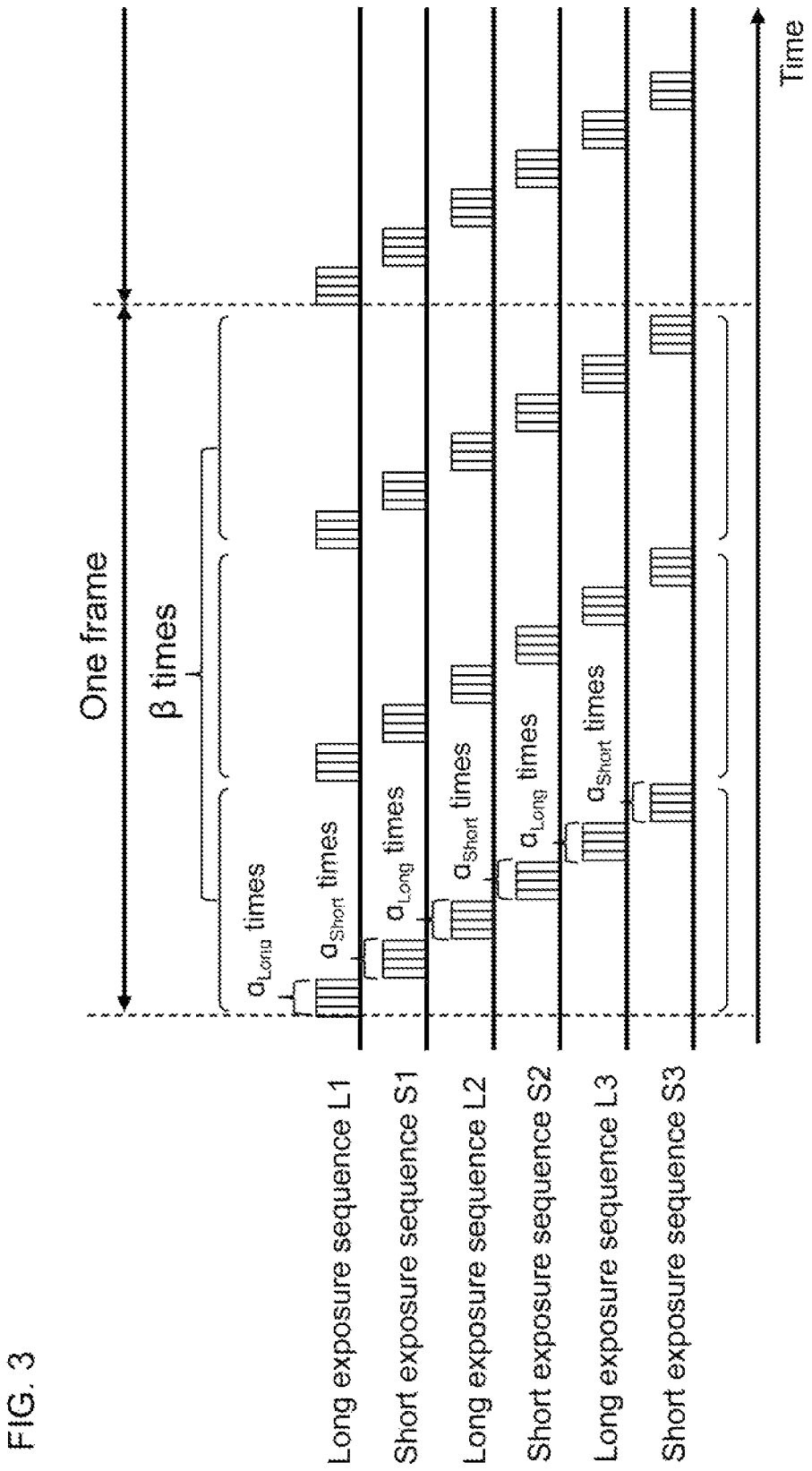
FIG. 3 is an illustration for describing an operation timing of the imaging device according to Embodiment 1 or 2.

Moreover, each exposure sequence is depicted only once in FIGS. 2A and 2B for the sake of simplifying the description. In implementation, however, as shown in FIG. 3, long exposure sequences L1 to L3 are each repeated $\alpha_{Long} \times \beta$ times in one frame period, and short exposure sequences S1 to S3 are each repeated $\alpha_{Short} \times \beta$ times in one frame period, in order to obtain a sufficient amount of signal charges from the standpoint of the S/N ratio. In this example, short exposure sequences S1 to S3 each have an irradiation time and an exposure period that are shorter than the irradiation time and the exposure period of each of long exposure sequences L1 to L3. Therefore, $\alpha_{Short}$ is set to $\alpha_{Long} \times Tp/Tp'$, for example, to mitigate the difference in the sensitivity between S0 and S0' and S1 and S1'.

In this example, in a case where an object to which the distance is to be measured is a moving object, one set in which each long exposure sequence is repeated $\alpha_{Long}$ times and each short exposure sequence is repeated $\alpha_{Short}$ times is repeated $\beta$ times. This, however, may not be applicable in a case where object 101 is a stationary object.

Figure 5:
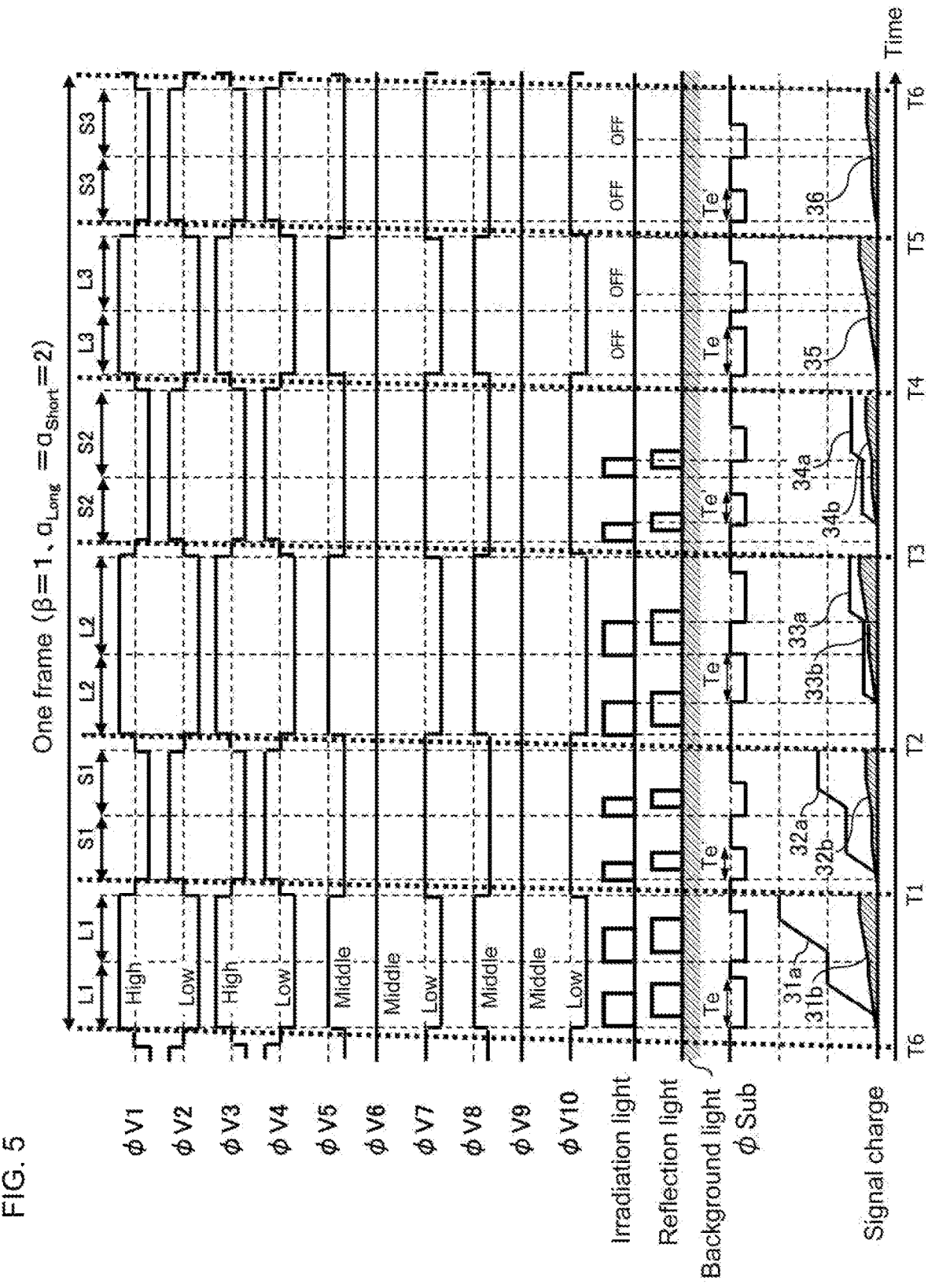
FIG. 5 is an illustration for describing a drive timing of a photoelectric converter and a vertical transferrer according to Embodiment 1 or 2.

Next, with reference to FIG. 5 and FIGS. 7 to 12, an operation timing of solid-state image sensor 106 in each exposure sequence will be described. FIG. 5 shows an example of a drive timing of photoelectric converters 4 and vertical transferrers 5 in the six types of exposure sequences constituting one frame period. FIGS. 7 to 12 provide visual representations of the addition and the transfer of the signal charges. In FIG. 5, for the sake of simplifying the description, an operation corresponding to only a segment where $\beta=1$ is depicted, and each exposure sequence is repeated twice ($\alpha_{Long}=\alpha_{Short}=2$). Meanwhile, in FIGS. 7 to 12, the directions in which the signal charges are read out and transferred are indicated by corresponding arrows.

First, in long exposure sequence L1 shown in FIG. 5, the voltages of φV1 and φV3 are each set to the High level, and the voltages of φV2 and φV4 are each set to the Low level. This produces a state in which the signal charges can be read out from four photoelectric converters 4 connected to V1 and V3 of corresponding vertical transferrer 5 in the odd number columns. In this example, the voltage of φSub is set to the Low level for exposure period Te in synchronization with the irradiation light. Thus, signal charges 31 from four photoelectric converters 4 are accumulated into corresponding vertical transferrer 5 in the odd number columns, as shown in (a) in FIG. 7. Each signal charge 31 includes irradiation light component 31a and background light component 31b. Signal charges 31 are accumulated separately in V1 and V3 of corresponding vertical transferrer 5. When the voltages of φV1, φV2, and φV3 are each set to the Middle level at time T1 shown in FIG. 5, signal charges 31 are turned into one packet, as shown in (b) in FIG. 7, and this means that the signal charges from four photoelectric converters 4 have been added. Thereafter, as shown in (c) in FIG. 7, signal charges 31 are transferred vertically in the forward direction (in the downward direction of the drawing) and become accumulated in V2 to V4.

Next, in short exposure sequence S1 shown in FIG. 5, the voltages of φV2 and φV4 are each set to the High level, and the voltages of φV1 and φV3 are each set to the Low level. This produces a state in which the signal charges can be read out from four photoelectric converters 4 connected to V2 and V4 of corresponding vertical transferrer 5 in the even number columns. In this example, the voltage of φSub is set to the Low level for exposure period Te' in synchronization with the irradiation light. Thus, signal charges 32 from four photoelectric converters 4 are accumulated into corresponding vertical transferrer 5 in the even number columns, as shown in (a) in FIG. 8. Each signal charge 32 includes irradiation light component 32a and background light component 32b. Signal charges 31 and signal charges 32 are each accumulated separately in V2 and V4 of corresponding vertical transferrer 5. When the voltages of φV2, φV3, and φV4 are each set to the Middle level at time T2 shown in FIG. 5, signal charges 31 and signal charges 32 are each turned into one packet, as shown in (b) in FIG. 8. Thereafter, as shown in (c) in FIG. 8, signal charges 31 and signal charges 32 are each transferred vertically in the forward direction (in the downward direction of the drawing) and become accumulated in V5 and V6.

Next, in long exposure sequence L2 shown in FIG. 5, solid-state image sensor 106 is driven in a manner similar to that in long exposure sequence L1 with the starting time of the exposure period shifted. Thus, as shown in (a) in FIG. 9, signal charges 33 from four photoelectric converters 4 are accumulated into corresponding vertical transferrer 5 in the odd number columns. At this point, since signal charges 31 have each been moved already to V5 and V6 through the foregoing transfer in the forward direction, signal charges 31 do not get mixed with signal charges 33. Each signal charge 33 includes irradiation light component 33a and background light component 33b. Signal charges 33 are accumulated separately in V1 and V3 of corresponding vertical transferrer 5. When the voltages of φV1, φV2, and φV3 are each set to the Middle level at time T3 shown in FIG. 5, signal charges 33 are turned into one packet, as shown in (b) in FIG. 9, and this means that the signal charges from four photoelectric converters 4 have been added. Thereafter, as shown in (c) in FIG. 9, signal charges 33 are each transferred vertically in the forward direction (in the downward direction of the drawing) and become accumulated in V2 to V4.

Next, in short exposure sequence S2 shown in FIG. 5, solid-state image sensor 106 is driven in a manner similar to that in long exposure sequence L2 with the starting time of the exposure period shifted. Thus, as shown in (a) in FIG. 10, signal charges 34 from four photoelectric converters 4 are accumulated into corresponding vertical transferrer 5 in the even number columns. At this point, since signal charges 32 have each been accumulated already in V5 and V6 through the foregoing transfer in the forward direction, signal charges 32 do not get mixed with signal charges 34. Each signal charge 34 includes irradiation light component 34a and background light component 34b. Signal charges 33 and signal charges 34 are each accumulated separately in V2 and V4 of corresponding vertical transferrer 5. When the voltages of φV2, φV3, and φV4 are each set to the Middle level at time T4 shown in FIG. 5, signal charges 33 and signal charges 34 are each turned into one packet, as shown in (b) in FIG. 10. Thereafter, as shown in (c) in FIG. 10, signal charges 33 and signal charges 34 are each transferred vertically in the forward direction (in the downward direction of the drawing) and become accumulated in V5 and V6.

Next, in long exposure sequence L3 shown in FIG. 5, solid-state image sensor 106 is driven in a manner similar to that in long exposure sequence L1 without the irradiation by the infrared light source. Thus, as shown in (a) in FIG. 11, signal charges 35 from four photoelectric converters 4 are accumulated into corresponding vertical transferrer 5 in the odd number columns. At this point, since signal charges 33 have each been moved already to V5 and V6 through the foregoing transfer in the forward direction, signal charges 33 do not get mixed with signal charges 35. Signal charges 35 are accumulated separately in V1 and V3 of corresponding vertical transferrer 5. When the voltages of φV1, φV2, and φV3 are each set to the Middle level at time T5 shown in FIG. 5, signal charges 35 are turned into one packet, as shown in (b) in FIG. 11, and this means that the signal charges from four photoelectric converters 4 have been added. Thereafter, as shown in (c) in FIG. 11, signal charges 35 are each transferred vertically in the forward direction (in the downward direction of the drawing) and become accumulated in V2 to V4.

Lastly, in short exposure sequence S3 shown in FIG. 5, solid-state image sensor 106 is driven in a manner similar to that in short exposure sequence S1 without the irradiation by the infrared light source. Thus, as shown in (a) in FIG. 12, signal charges 36 from four photoelectric converters 4 are accumulated into corresponding vertical transferrer 5 in the even number columns. At this point, since signal charges 34 have each been accumulated already in V5 and V6 through the foregoing transfer in the forward direction, signal charges 34 do not get mixed with signal charges 36. Signal charges 35 and signal charges 36 are each accumulated separately in V2 and V4 of corresponding vertical transferrer 5. When the voltages of φV2, φV3, and φV4 are each set to the Middle level at time T6 shown in FIG. 5, signal charges 35 and signal charges 36 are each turned into one packet, as shown in (b) in FIG. 12. Thereafter, as shown in (c) in FIG. 12, signal charges 31 to signal charges 36 are each transferred vertically in the reverse direction (in the upward direction of the drawing), and this produces a state in which signal charges 31 and signal charges 32 are each accumulated in V1 to V3, that is, a state in which long exposure sequence L1 can be executed again.

Repeating the above-described operation 1 times allows the six types of signal charges with respect to reflection light 111 corresponding to one frame period to be accumulated into vertical transferrers 5 independently and with high sensitivity.

In this example, signal charges 31, signal charges 33, and signal charges 35 may be accumulated in vertical transferrers 5 in the even number columns, and signal charges 32, signal charges 34, and signal charges 36 may be accumulated in vertical transferrers 5 in the odd number columns. In this case, φV6 and φV8 serve as the readout electrodes for photoelectric converters 4 in the odd number columns. Moreover, the types of signal charges to be accumulated in vertical transferrers 5 in the odd number columns and the types of signal charges to be accumulated in vertical transferrers 5 in the even number column may be switched in every frame. In this case, the signal charges are interlaced in the column direction between frames, and this provides an expectation that the spatial resolution of distance signal 115 in the horizontal direction can be improved.

In the example described above, solid-state image sensor 106 is a CCD image sensor. Alternatively, solid-state image sensor 106 may be a complementary metal-oxide semiconductor (CMOS) image sensor.

Expression 1 and Expression 2 below are for a calculator that calculates two types of distances z and z' in control arithmetic device 107 according to the present embodiment. When the speed of light is denoted by c, distance z is calculated through Expression 1 by use of signal charges S0 and S1, in which the influence of the background light obtained in long exposure sequences L1 to L3 has been removed. In a similar manner, distance z' is calculated through Expression 2 by use of signal charges S0' and S1', in which the influence of the background light obtained in short exposure sequences S1 to S3 has been removed. Moreover, $\Delta Te'$ serves as the lower limit of distance z' and as a parameter that determines the degree of overlap between the distance range of distance z and the distance range of distance z'.

$$z = c \times \Delta t/2 =$$

$$(c \times Tp/2) \times (\Delta t/Tp) =$$

$$(c \times Tp/2) \times (S1/S0) \qquad \text{Expression 1}$$

$$z' = c \times \Delta t/2 =$$

$$(c \times Tp'/2) \times (\Delta t/Tp') =$$

$$(c \times Tp'/2) \times (S1'/S0') =$$

$$(c \times Tp'/2) \times (S1'/S0') + (c \times \Delta Te'/2) \qquad \text{Expression 2}$$

Herein, when a case where $\Delta Te' = 0$ is considered, although distances z and z' ideally take the same value, in reality, a difference in the precision arises between distances z and z' since the calculation is performed by use of the signal charge amounts quantized to a finite resolution. For example, provided that S1/S0 and S1'/S0' are each quantized to the N-bit integer precision, the unit distance of distance z is $(c \times Tp/2)/2N$, and the unit distance of distance z' is $(c \times Tp'/2)/2N$. Therefore, distance z' has a higher distance precision. Meanwhile, the maximum value of distance z is $(c \times Tp/2) \times (2N-1)/2N$, and the maximum value of distance z' is $(c \times Tp'/2) \times (2N-1)/2N$. Therefore, distance z has a greater distance range. Accordingly, calculating the two types of distances z and z' makes it possible to achieve both the range finding in a broad distance range and the range finding with high distance precision.

The length of the irradiation time and the length of the exposure period may each be set to the same length between long exposure sequences L1 to L3 and short exposure sequences S1 to S3 (i.e., Tp=Tp', Te=Te'). In addition, the signal charges may be accumulated and the distances may be calculated with $\Delta Te'$ set to Tp. In this case, distances z and z' have the same distance precision, and the combination of distances z and z' yields the distance range that is twice the distance range of distance z.

The operation described above makes it possible to accumulate the six types of signal charges independently in the vertical transferrers in one frame period. Moreover, since the signal charges from the four photoelectric converters are added, the sensitivity increases substantially twofold as compared with a conventional method in which the signal charges from two photoelectric converters are added. Therefore, any decrease in each charge amount associated with an increase in the number of types of signal charges to be accumulated can be canceled out. Accordingly, two types of distances having different distance ranges and different distance precisions can be calculated with high accuracy, and this makes it possible to achieve both the range finding in a broad distance range and the range finding with high distance precision.

As described thus far, the imaging device according to Embodiment 1 includes solid-state image sensor 106 and control arithmetic device 107. Solid-state image sensor 106 is exposed to reflection light from an object and accumulates the reflection light in the form of a signal charge. Control arithmetic device 107 controls the irradiation by infrared light source 103 and the exposure of solid-state image sensor 106. Solid-state image sensor 106 includes a plurality of photoelectric converters 4 and a plurality of charge accumulators. The plurality of photoelectric converters 4 each convert reflection light from an object into a signal charge, and the plurality of charge accumulators accumulate the signal charges. The imaging device performs m types of exposure sequences (m is an integer greater than or equal to four) within one frame period in order to control the irradiation and the exposure, assigns the charge accumulators exclusively to the m types of exposure sequences, and accumulates the signal charges obtained from n photoelectric converters (n is an integer greater than or equal to three) into the charge accumulators in at least one type of exposure sequence among the m types of exposure sequences.

In this configuration, control arithmetic device 107 may repeatedly perform at least one type of exposure sequence within one frame period.

In this configuration, control arithmetic device 107 may set a correspondence between a set of n photoelectric converters and one charge accumulator and accumulate the signal charges obtained from the n photoelectric converters into the corresponding charge accumulator.

In this configuration, control arithmetic device 107 may add the signal charges obtained from the n photoelectric converters and accumulate the resultant signal charges into the corresponding charge accumulator in at least one type of exposure sequence.

Moreover, the m types of exposure sequences may differ from each other in terms of at least one of the irradiation intensity of the light source, the irradiation time of the light source, the irradiation wavelength of the light source, or the exposure period of the image sensor.

Control arithmetic device 107 may change the photoelectric converts constituting the set of the n photoelectric converters in every k type of exposure sequence (k is an integer greater than or equal to one).

In this configuration, the imaging device may set the number of repetitions of the m types of exposure sequences based on the irradiation intensity of the light source, the irradiation time of the light source, the irradiation wavelength of the light source, and the exposure period of the solid-state image sensor.

In this configuration, the imaging device may change, in every frame, the photoelectric converters constituting the set of the n photoelectric converters from which the signal charges are read out and added.

In this configuration, the m may be five or six, the plurality of photoelectric converters may be disposed in a matrix, the imaging device may repeat the exposure sequences of five or six types a plurality of times in one frame period, and the n photoelectric converters may be a set of four photoelectric converters, among the plurality of photoelectric converters, that are disposed in two rows by two columns.

In this configuration, the imaging device may be a time of flight (TOF) range finding device, and the imaging device may include a distance calculator that calculates the distance to the object by use of the signal charges accumulated in the charge accumulators in at least two types of exposure sequences among the m types of exposure sequences.

In this configuration, the m types of exposure sequences may include a long exposure sequence and a short exposure sequence, the irradiation time of the light source and the exposure period of the solid-state image sensor may each be set longer in the long exposure sequence than in the short exposure sequence, and the distance calculator may calculate at least two types of distances to the object based on the m types of exposure sequences.

In this configuration, the imaging device may be a TOF range finding device, the photoelectric converters may be disposed in a matrix, the m types of exposure sequences may include first to third long exposure sequences and first to third short exposure sequences, the irradiation time of the light source and the exposure period of the solid-state image sensor may each be longer in the first to third long exposure sequences than in the first to third short exposure sequences, the exposure period in the second long exposure sequence may differ from the exposure period in the first long exposure sequence, the exposure period in the second short exposure sequence may differ from the exposure period in the first short exposure sequence, the third long exposure sequence and the third short exposure sequence may each involve the exposure to background light that includes no reflection light component associated with the irradiation by the light source, the first to third long exposure sequences and the first to third short exposure sequences may each be repeated a plurality of times within one frame period, the n photoelectric converters may be four photoelectric converters, among the plurality of photoelectric converters, that are disposed in two rows by two columns, and the imaging device may include a distance calculator that calculates two types of distances to the object by use of the signal charges that are accumulated in the first to third long exposure sequences and the signal charges that are added and accumulated in the first to third short exposure sequences.

In this configuration, the irradiation by the light source may be performed in the third long exposure sequence and the third short exposure sequence, and the period after the reflection light has become extinct may serve as the exposure period.

Embodiment 2

Now, an imaging device according to Embodiment 2 will be described with the description centered on the differences from the imaging device according to Embodiment 1. In the configuration example described in Embodiment 2, in an environment where so-called multipass of coexisting direct reflection wave and indirect reflection wave is likely to occur, any erroneous measurement caused by such multipass is suppressed or warned. Accordingly, like the imaging device according to Embodiment 1, the imaging device according to the present embodiment has the schematic configuration of the imaging device shown in FIG. 1, includes the solid-state image sensor shown in FIGS. 4A and 4B, and operates in accordance with the operation timings shown in FIGS. 2A to 2C and in accordance with the drive timing shown in FIG. 5. In the imaging device according to the present embodiment, in addition to the configuration of the imaging device according to Embodiment 1, control arithmetic device 107 further includes a distance range determiner that determines the range of distance z' and a distance corrector that corrects distance z by use of distance z'. In this example, distance z corresponds to the distance measured through long exposure sequences L1 to L3 or the distance range in which the distance can be measured through long exposure sequences L1 to L3. Meanwhile, distance z' corresponds to the distance measured through short exposure sequences S1 to S3 or the distance range in which the distance can be measured through short exposure sequences S1 to S3.

The distance range determiner is provided with a full scan mode and a selective scan mode. In the full scan mode, the distance range determiner shifts the distance range of distance z' by a predefined amount in every frame. In the selective scan mode, the distance range determiner scans the distance range of distance z' based on the distribution of distances z in preceding frames.

Figure 13A:
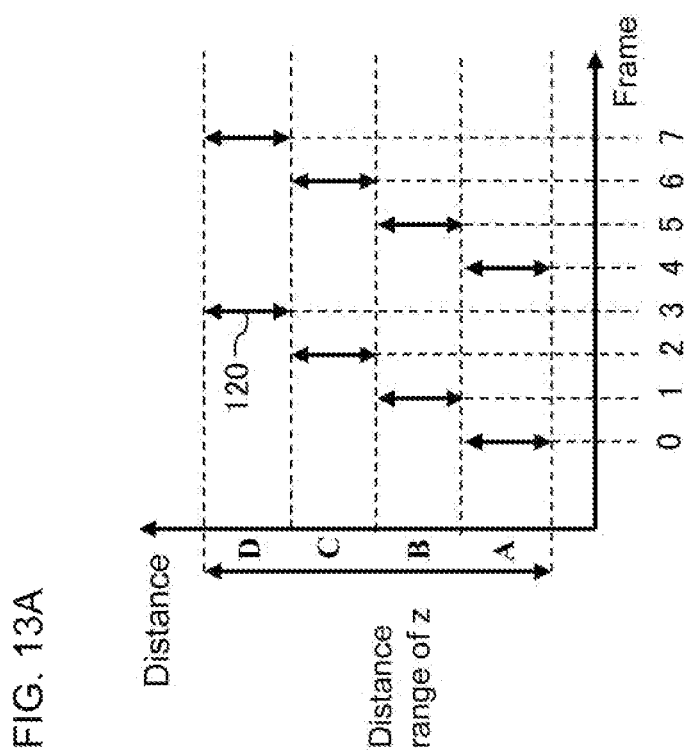
FIG. 13A is an illustration for describing an operation example of a distance range setter according to Embodiment 2.

As shown in FIG. 13A, in the full scan mode, the distance range determiner determines $\Delta Te'$ such that distance range 120 of distance z' overlaps a part of the distance range of distance z (i.e., $\Delta Te'+Tp' \le Tp$, based on Expression 2) and performs the scan on a frame by frame basis. For example, in a case where $Tp=4Tp'$, the distance range determiner sets distance range 120 of distance z' to distance range A by setting $\Delta Te'$ to 0 in frame 0, sets distance range 120 of distance z' to distance range B by setting $\Delta Te'$ to $Tp'$ in frame 1, sets distance range 120 of distance z' to distance range C by setting $\Delta Te'$ to $2Tp'$ in frame 2, sets distance range 120 of distance z' to distance range D by setting $\Delta Te'$ to $3Tp'$ in frame 3, and sets distance range 120 of distance z' to distance range A by setting $\Delta Te'$ to 0 again in frame 4. Then, the distance range determiner repeats this operation thereafter.

Through the operation described above, distance range 120 of distance z' is scanned in a predefined cycle in the full scan mode, and thus the distance can be measured with high accuracy over a broad distance range.

Figure 13B:
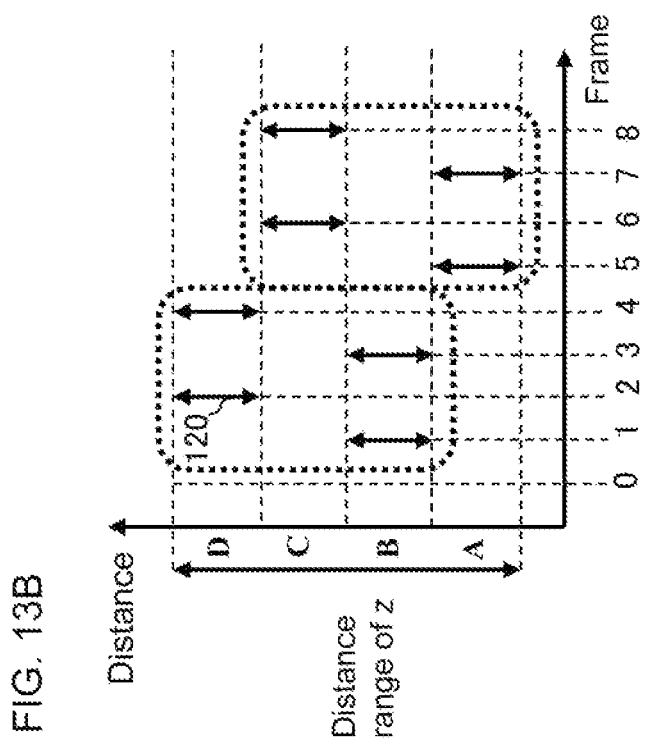
FIG. 13B is an illustration for describing another operation example of the distance range setter according to Embodiment 2.
Figure 13C:
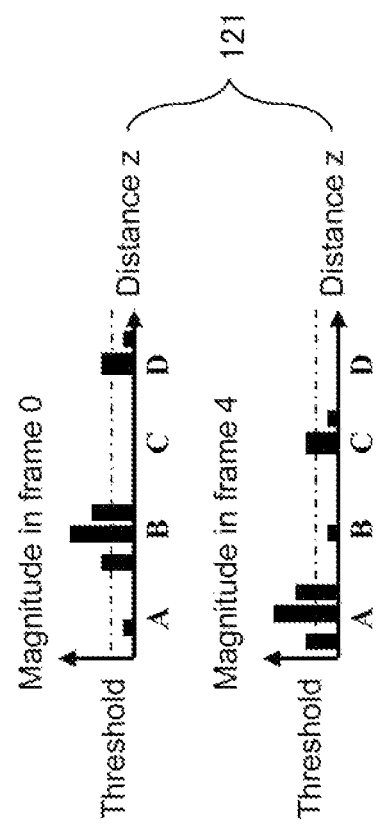
FIG. 13C is an illustration for describing a part of the other operation example of the distance range setter according to Embodiment 2.

Meanwhile, as shown in FIGS. 13B and 13C, in the selective scan mode, the distance range determiner calculates histogram 121 of distance z in a predefined cycle, determines distance range 120 of distance z' such that distance range 120 of distance z' overlaps the distance range in which the magnitude of histogram 121 is greater than or equal to a threshold, and performs the scan on a frame by frame basis. For example, as in the example shown in FIG. 13C, in a case where the distance range determiner calculates histograms 121 of distance z in each set of four frames, since the magnitude of histogram 121 exceeds the threshold in distance ranges B and D according to histogram 121 of distance z in frame 0, the distance range determiner scans only distance ranges B and D with respect to the distance range of distance z' in frames 1 to 4. Meanwhile, since the magnitude of histogram 121 exceeds the threshold in distance ranges A and C in frame 4, the distance range determiner scans only distance ranges A and C with respect to the distance range of distance z' in frames 5 to 8.

Through the operation described above, the distance range of distance z' is scanned selectively based on distance z to the object in the selective scan mode. Therefore, the distance can be measured with high accuracy in a shorter cycle in the selective scan mode than in the full scan mode, and thus the selective scan mode can provide a higher following performance in the range finding of a moving object.

In a case where a region in which an object of interest is to be imaged is known, histogram 121 of distance z may be calculated not in the entire imaging region but in the limited region in which the object of interest is to be imaged. In this case, the magnitude of the histogram is concentrated near the distance to the object of interest, and thus distance range 120 of distance z' can be scanned more efficiently. Moreover, in a case where there are a plurality of objects of interest, an operation similar to the one described above can be implemented by adding histograms 121 of distances z in the regions where the respective objects of interest are imaged.

The distance corrector is provided with a high precision mode and a multipass correction mode. In the high precision mode, the distance corrector increases the precision of a part of distance z by use of distance z'. In the multipass correction mode, the distance corrector reduces the influence of multipass on distance z by use of distance z'. The distance corrected by the distance corrector is output in the form of distance signal 115.

In the high precision mode, the distance corrector holds distance zh whose precision has been increased over a plurality of frames, updates distance zh in a partial region with distance z' of high precision on a frame by frame basis, and updates distance zh in the remaining region with distance z of low precision if there is a change in the distance (or if the change in the distance is large) or holds the original distance if there is no change in the distance (or if the change in the distance is small). For example, as shown in FIG. 14, in frame 0, the distance corrector initializes the entire region of distance zh with distance z (arrows 130) and then updates distance zh with distance z' for region A that falls within the distance range of distance z' (arrow 131). Then, in frame 1, the distance corrector updates distance zh with distance z' for region B that falls within the distance range of distance z' (arrow 131) and refrains from making any update for regions A and C since there is no difference between distance zh and distance z. In a similar manner, in frame 2, the distance corrector updates distance zh with distance z' for region C that falls within the distance range of distance z' (arrow 131) and refrains from making any update for regions A and C since there is no difference between distance zh and distance z. Moreover, in frame 3, the distance corrector updates distance zh with distance z' for region A that falls within the distance range of distance z' (arrow 131), updates distance zh with distance z for region B since there is a difference between distance zh and distance z (arrow 132), and refrains from making any update for region C since there is no difference between distance zh and distance z.

Through the operation described above, the distance to a stationary object can be measured with high distance precision while the range finding is performed so as to follow the moving object in the high precision mode.

Figure 15:
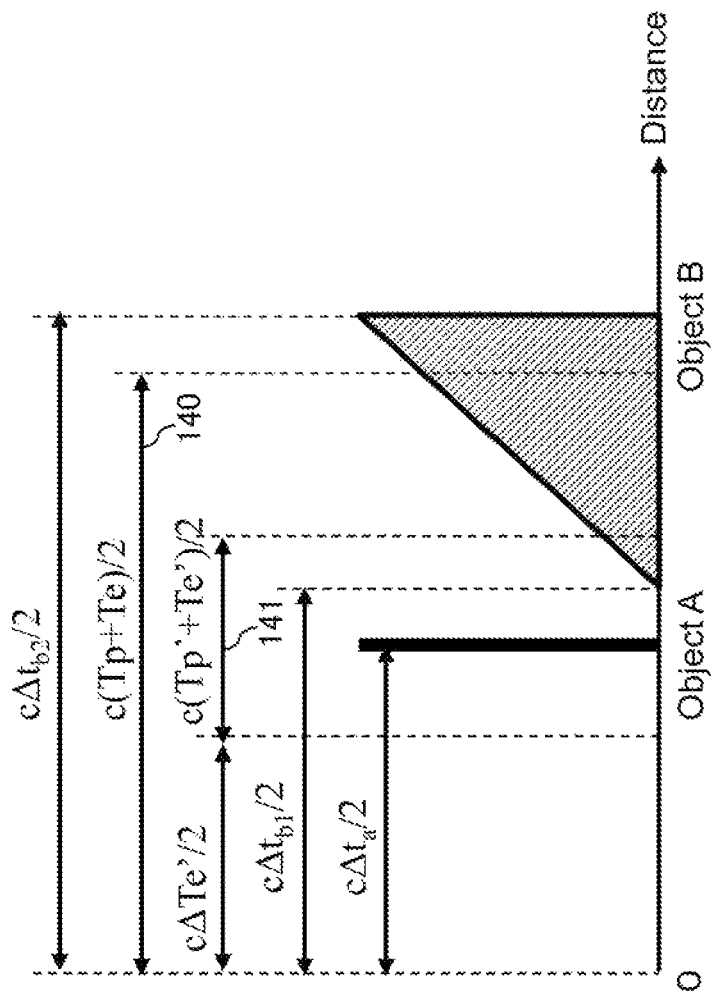
FIG. 15 is an illustration for describing an observation range of reflection light from a far object.

Meanwhile, in the multipass correction mode, the distance corrector calculates distance zc in which the influence of multipass has been reduced. In this example, the term "multipass" means multiple reflections of irradiation light. When a given object receives and reflects reflection light from another object located behind the given object, the point indicated by the measured distance may be shifted farther back than the point to be indicated by the actual distance. For example, considered below is a case in which the reflection light from object B is observed via object A when the object A is located at distance $c\Delta t_a/2$ and object B is located at distance $(c\Delta t_{b2}/2 - c\Delta t_{b1}/2)$, as shown in FIG. 15. First, observation range 140 of the reflection light from object B in long exposure sequences L1 and L2 spans from distance 0 to distance $c(Tp+Te)/2$. Meanwhile, observation range 141 of the reflection light from object B in short exposure sequences S1 and S2 spans from distance $c\Delta Te'/2$ to distance $c(\Delta Te'+Tp'+Te')/2$. In this example, the condition where $Te' < Te$ and $\Delta Te'+Tp' \le Tp$ yields $(\Delta Te'+Tp'+Te') \le (Tp+Te)$. Excluding the boundary condition, the reflection light from object B is observed less in observation range 141 than in observation range 140, and therefore any mismatch associated with the influence of multipass is smaller in distance z' than in distance z. Accordingly, in the multipass correction mode, for the region that falls within the distance range of distance z', the distance corrector determines that the range finding is under the influence of multipass and sets distance zc to distance z' if the difference between distance z and distance z' is greater than a value set in advance or sets distance zc to distance z if the distance corrector determines that the range finding is not under the influence of multipass.

Through the operation described above, in the multipass correction mode, the distance corrector detects any region that is under the influence of multipass and outputs selectively distance z' that is less affected by multipass. Thus, the influence of multipass can be reduced.

Alternatively, for the region that is under the influence of multipass, instead of simply selecting and outputting distance z', the distance corrector may calculate the weighted average of distance z' and distance z in accordance with the degree of influence of multipass and output the calculated weighted average. Moreover, the imaging device may include an anomaly notifier that outputs a signal for letting know of an anomaly, aside from distance signal 115, if the distance corrector has determined that the range finding is under the influence of multipass.

The distance range determiner and the distance corrector described above make it possible to achieve both the range finding in a broad distance range and the range finding with high accuracy by combining the two types of distances, namely distances z and z'. Moreover, reducing the influence of multipass makes it possible to measure the distance with higher accuracy.

As described thus far, the imaging device according to Embodiment 2 includes a distance corrector, and the distance corrector corrects the distance calculated in the long exposure sequence or in the first to third long exposure sequences by use of the distance calculated in the short exposure sequence or in the first to third short exposure sequences.

In this configuration, the imaging device may include an anomaly notifier, and the anomaly notifier may let know of an anomaly in a case where a difference between a part of the distance calculated in the long exposure sequence or in the first to third long exposure sequences and the distance calculated in the short exposure sequence or in the first to third short exposure sequences exceeds a prescribed range.

In this configuration, when the exposure period in the short exposure sequence or in the first to third short exposure sequences is regarded as a short exposure period, the short exposure period is changed in every frame, and in response to the change in the short exposure period in every frame, the scan may be performed with a condition that the distance range calculated in the short exposure sequence or in the first to third short exposure sequences overlaps a part of the distance range calculated in the long exposure sequence or in the first to third long exposure sequences.

In this configuration, the exposure period in the short exposure sequence or in the first to third short exposure sequences may be set based on the distance calculated in the first to third long exposure sequences of a preceding frame.

Embodiment 3

Now, an imaging device according to Embodiment 3 will be described with the description centered on the differences from the imaging device according to Embodiment 1. In the configuration example described in Embodiment 3, the dynamic range of the range finding is increased by use of a strong irradiation light and a weak irradiation light. That the dynamic range is increased means that the range in which the distance can be measured is broadened so that the distance to a near object with high reflectance as well as the distance to a far object with low reflectance can be measured. Therefore, like the imaging device according to Embodiment 1, the imaging device according to the present embodiment has the schematic configuration of the imaging device shown in FIG. 1 and includes the solid-state image sensor shown in FIGS. 4A and 4B. However, unlike the imaging device according to Embodiment 1, the imaging device according to the present embodiment performs the range finding by use of a plurality of exposure sequences in which the irradiation intensity of infrared light source 103 differs.

Figure 16A:
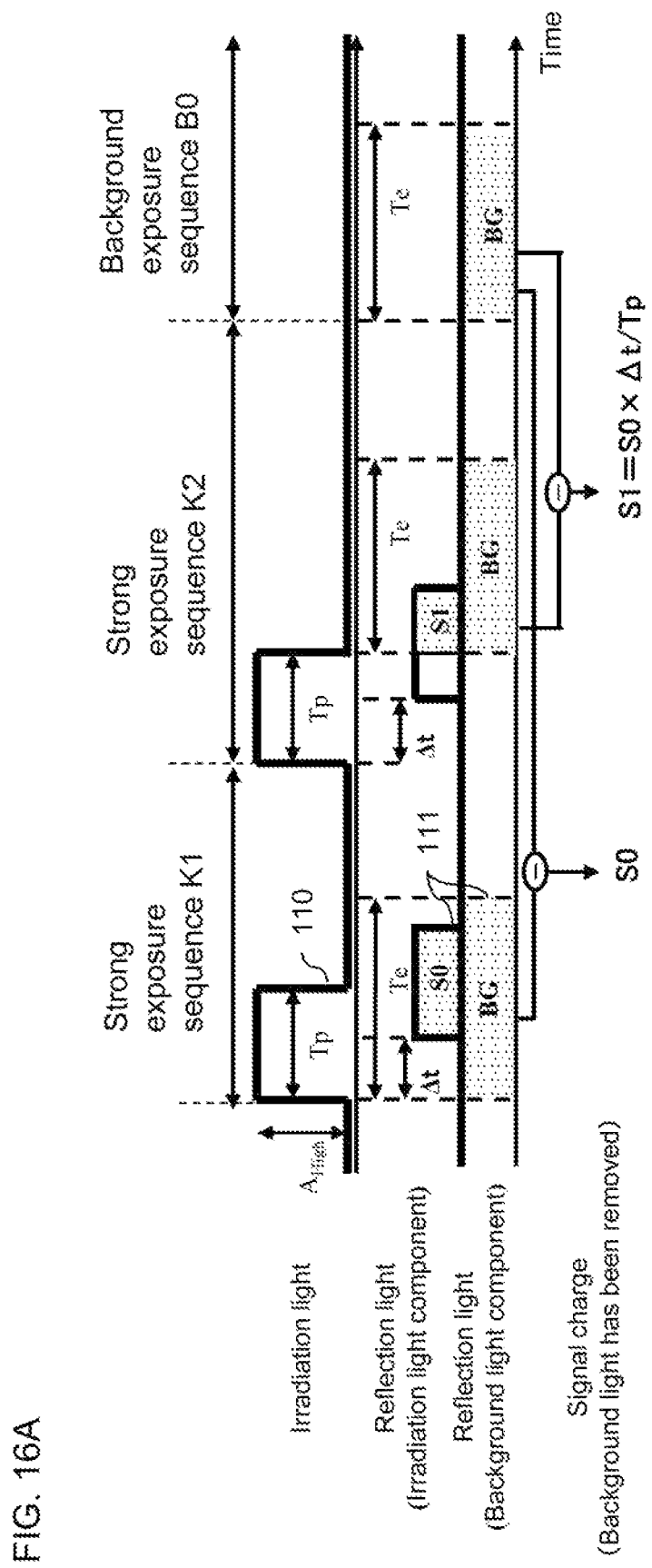
FIG. 16A is an illustration for describing an operation timing example and an operation principle of the imaging device according to Embodiment 3.
Figure 16B:
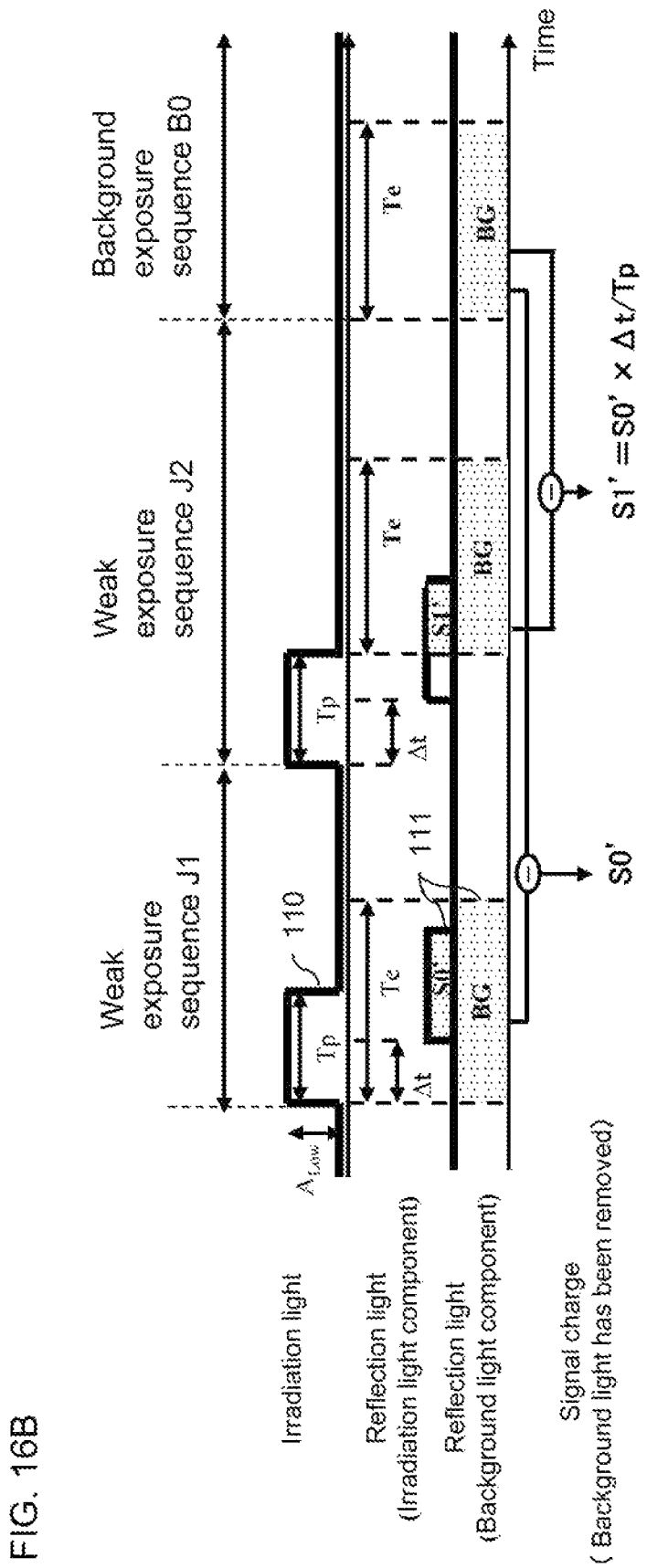
FIG. 16B is an illustration for describing another operation timing example and an operation principle of the imaging device according to Embodiment 3.

FIGS. 16A and 16B are illustrations for describing an operation timing and an operation principle of the imaging device according to the present embodiment. As shown in FIGS. 16A and 16B, an operation of the imaging device includes a total of five exposure sequences, namely strong exposure sequences K1 and K2, weak exposure sequences J1 and J2, and background exposure sequence B0. These exposure sequences are implemented as control arithmetic device 107 performs control 112 of controlling the irradiation timing of infrared light source 103 and control 113 of controlling the exposure timing of solid-state image sensor 106, and one type of signal charge is obtained in each of the exposure sequences. In this example, the pulse duration (the irradiation time) of irradiation light 110 is denoted by Tp, the delay between irradiation light 110 and reflection light 111 is denoted by Δt, and the length of the exposure period is denoted by Te.

First, as shown in FIG. 16A, in strong exposure sequence K1, with the irradiation intensity of irradiation light 110 set to AHigh, control arithmetic device 107 performs control 112 of controlling the irradiation timing and control 113 of controlling the exposure timing such that the exposure period starts at the rise of irradiation light 110 and includes the fall of reflection light 111. Thus, control arithmetic device 107 obtains signal charge S0+BG that is based on reflection light 111. Next, in strong exposure sequence K2, with the irradiation intensity of irradiation light 110 set to AHigh, control arithmetic device 107 performs control 112 of controlling the irradiation timing and control 113 of controlling the exposure timing such that the exposure period starts at the fall of irradiation light 110. Thus, control arithmetic device 107 obtains signal charge S1+BG that is based on reflection light 111. Moreover, in background exposure sequence B0, control arithmetic device 107 performs control 112 of controlling the irradiation timing and control 113 of controlling the exposure timing such that only the exposure is carried out without the irradiation of irradiation light 110. Thus, control arithmetic device 107 obtains signal charge BG that is based on reflection light 111. Thereafter, control arithmetic device 107 extracts signal charges S0 and S1 that are not dependent on the background light by subtracting BG from each of S0+BG and S1+BG.

In a similar manner, as shown in FIG. 16B, in weak exposure sequence 31, with the irradiation intensity of irradiation light 110 set to ALow that is lower than AHigh, control arithmetic device 107 performs control 112 of controlling the irradiation timing and control 113 of controlling the exposure timing such that the exposure period starts at the rise of irradiation light 110 and includes the fall of reflection light 111. Thus, control arithmetic device 107 obtains signal charge S0'+BG that is based on reflection light 111. Next, in weak exposure sequence J2, with the irradiation intensity of irradiation light 110 set to ALow, control arithmetic device 107 performs control 112 of controlling the irradiation timing and control 113 of controlling the exposure timing such that the exposure period starts at the fall of irradiation light 110. Thus, control arithmetic device 107 obtains signal charge S1'+BG that is based on reflection light 111. The operation in background exposure sequence B0 is similar to that described with reference to FIG. 16A. Thereafter, control arithmetic device 107 extracts signal charges S0' and S1' that are not dependent on the background light by subtracting BG from each of S0'+BG and S1'+BG.

Moreover, each exposure sequence is shown only once in FIGS. 16A and 16B for the sake of simplifying the description. In implementation, however, as shown in FIG. 17, each exposure sequence is repeated α×β times in one frame period in order to obtain a sufficient amount of signal charges from the standpoint of the S/N ratio.

In a case where it is difficult to adjust each of AHigh and ALow to a desired intensity because of the characteristics of infrared light source 103, the total amount of light in one frame period may be adjusted individually by repeating the set of strong exposure sequences K1 and K2 $\alpha_{High} \times \beta$ times and repeating the set of weak exposure sequences J1 and J2 $\alpha_{Low} \times \beta$ times. In this case, since the amount of charges in the background light component included in the signal charges differs between strong exposure sequences K1 and K2 and weak exposure sequences J1 and 32, BG to be subtracted may be corrected at the ratio of $\alpha_{High} : \alpha_{Low}$.

Figure 6:
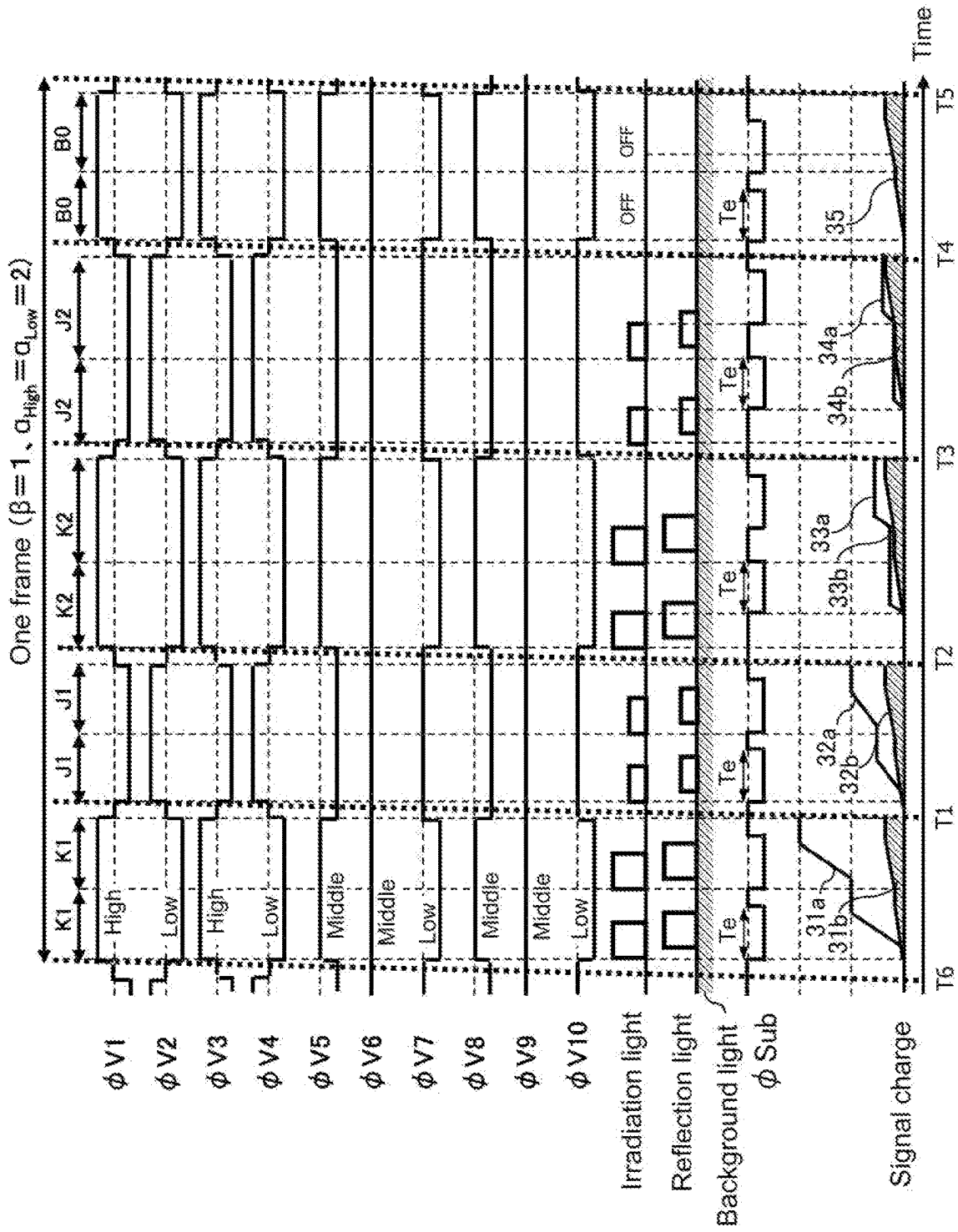
FIG. 6 is an illustration for describing a drive timing of a photoelectric converter and a vertical transferrer according to Embodiment 3.
Figure 7:
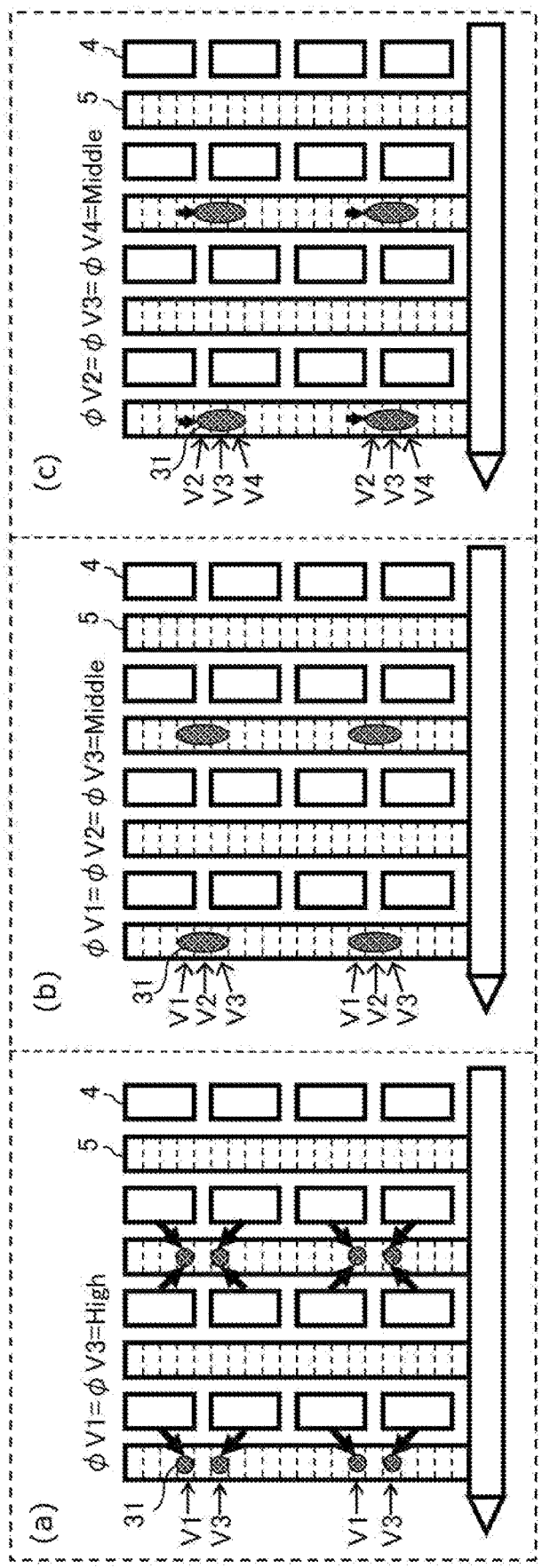
FIG. 7, including (a), (b), and (c), is an illustration for describing the addition and the transfer of signal charges in long exposure sequence L1 according to Embodiment 1 or 2, in strong exposure sequence K1 according to Embodiment 3, and in 750-nm sequence P1 according to Embodiment 4.
Figure 8:
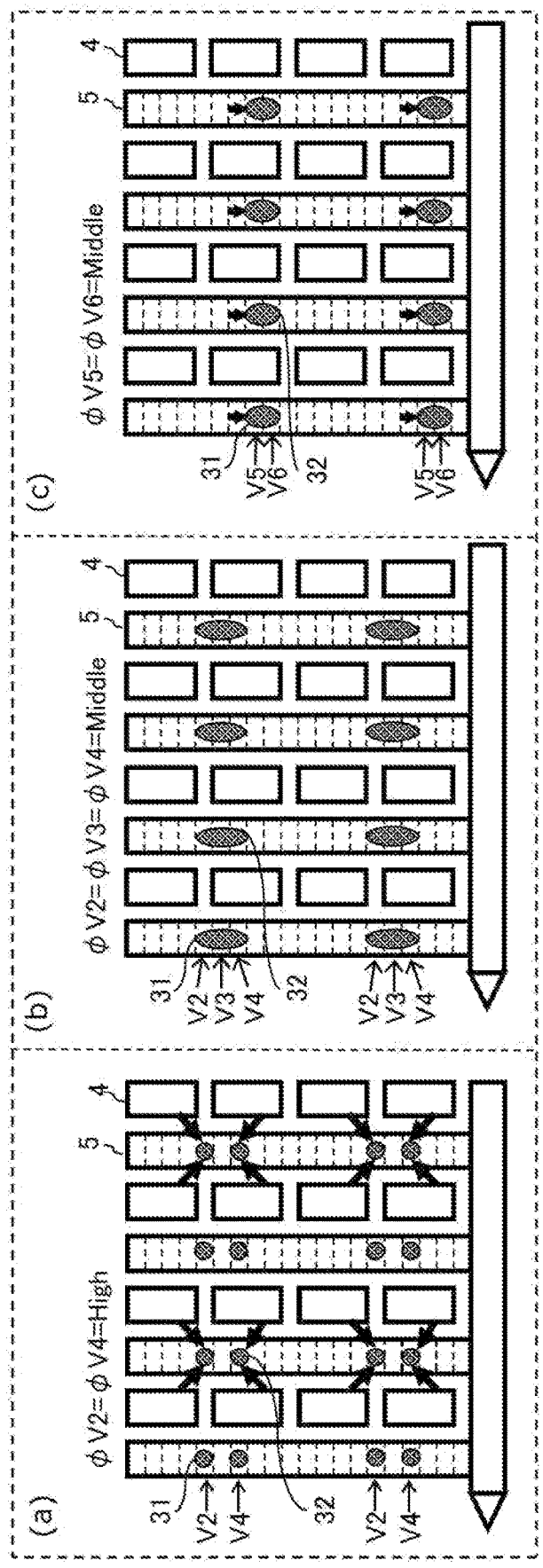
FIG. 8, including (a), (b), and (c), is an illustration for describing the addition and the transfer of signal charges in short exposure sequence S1 according to Embodiment 1 or 2, in weak exposure sequence 31 according to Embodiment 3, and in 850-nm sequence Q1 according to Embodiment 4.
Figure 9:
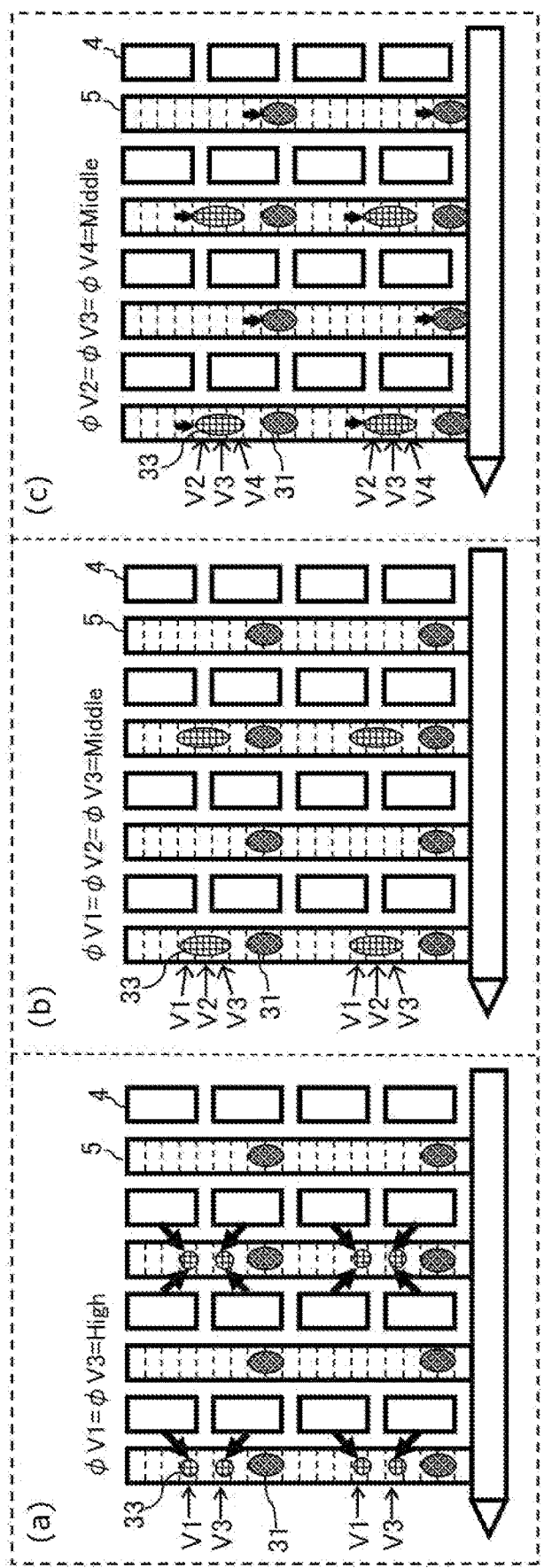
FIG. 9, including (a), (b), and (c), is an illustration for describing the addition and the transfer of signal charges in long exposure sequence L2 according to Embodiment 1 or 2, in strong exposure sequence K2 according to Embodiment 3, and in 750-nm sequence P2 according to Embodiment 4.
Figure 10:
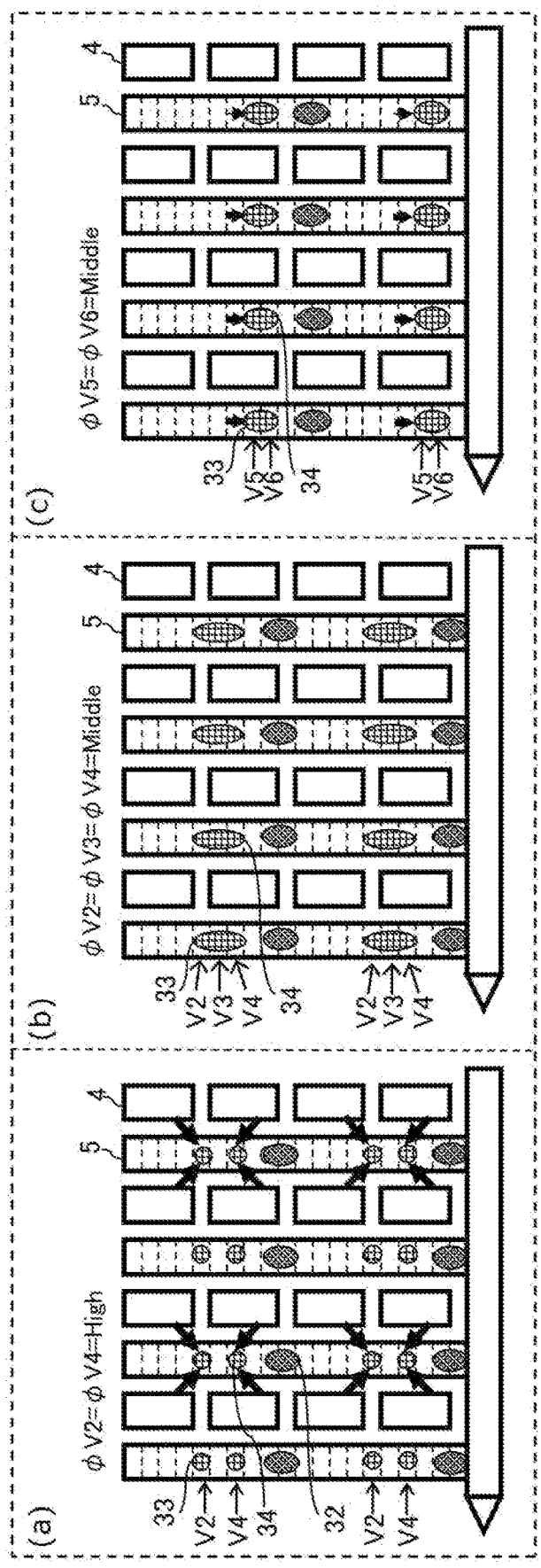
FIG. 10, including (a), (b), and (c), is an illustration for describing the addition and the transfer of signal charges in short exposure sequence S2 according to Embodiment 1 or 2, in weak exposure sequence 32 according to Embodiment 3, and in 850-nm sequence Q2 according to Embodiment 4.
Figure 11:
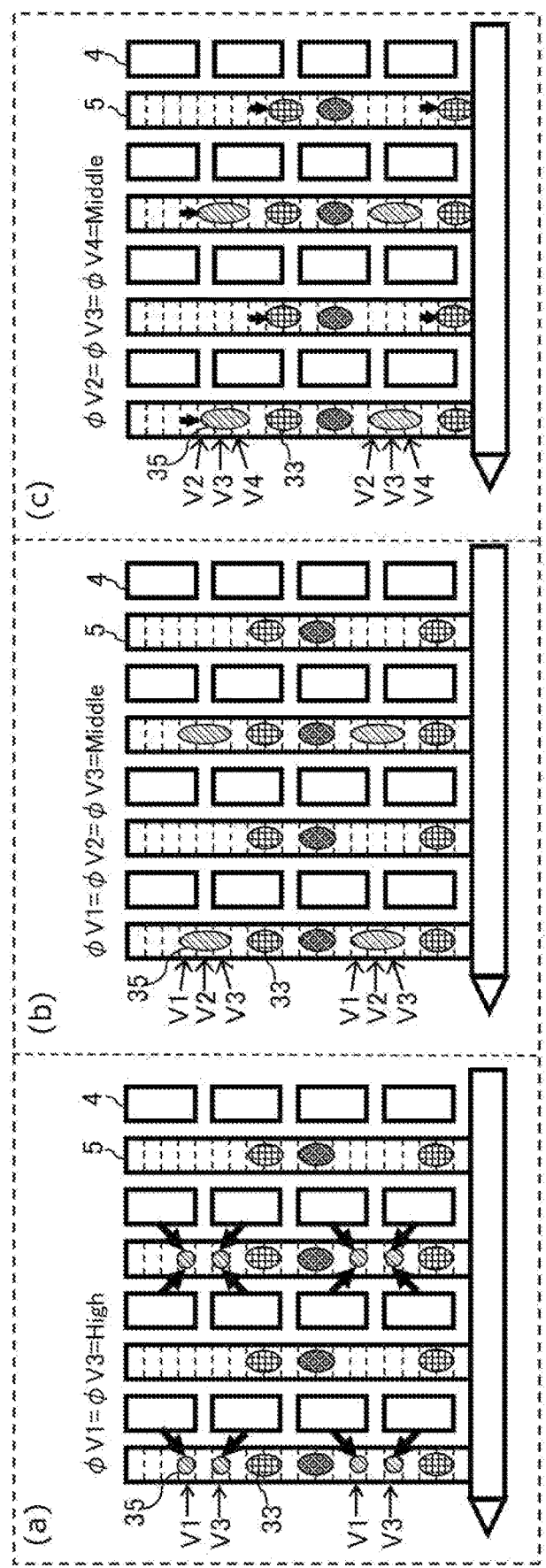
FIG. 11, including (a), (b), and (c), is an illustration for describing the addition and the transfer of signal charges in long exposure sequence L3 according to Embodiment 1 or 2, in background exposure sequence B0 according to Embodiment 3, and in 750-nm sequence P3 according to Embodiment 4.
Figure 12:
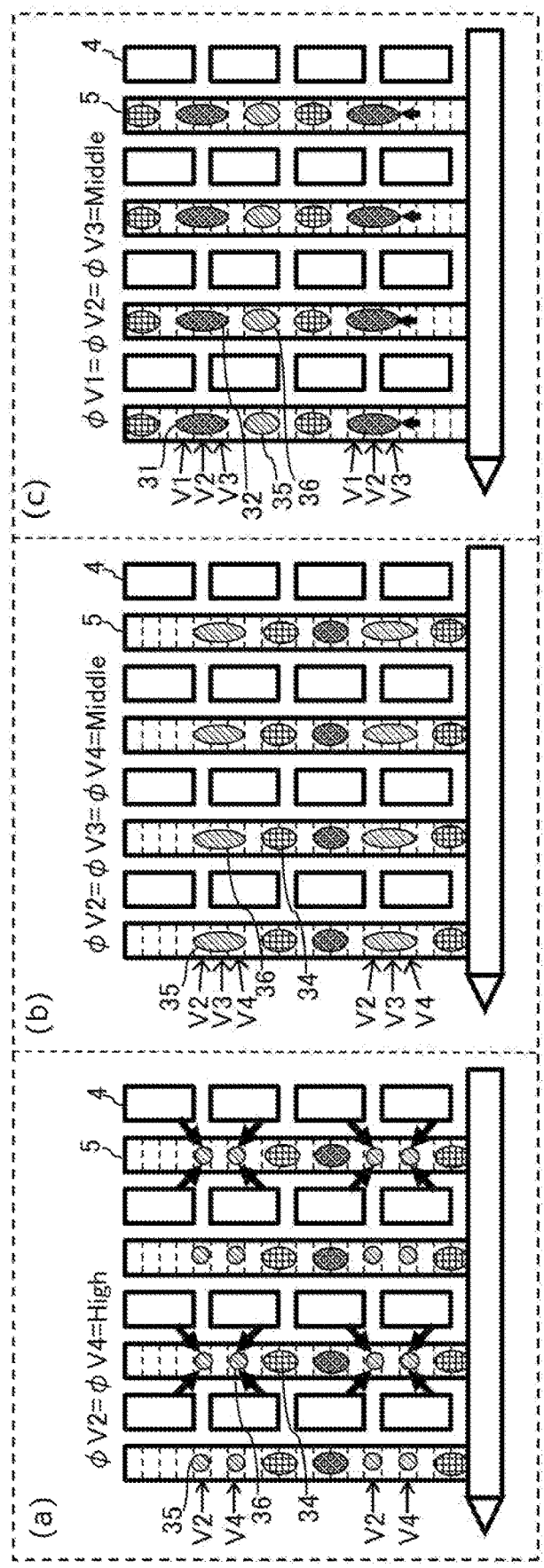
FIG. 12, including (a), (b), and (c), is an illustration for describing the addition and the transfer of signal charges in short exposure sequence S3 according to Embodiment 1 or 2 and in 850-nm sequence Q3 according to Embodiment 4.

Next, with reference to FIG. 6 and FIGS. 7 to 12, an operation timing of solid-state image sensor 106 in each exposure sequence will be described. FIG. 6 shows an example of a drive timing of photoelectric converters 4 and vertical transferrers 5 in five types of exposure sequences constituting one frame period. FIGS. 7 to 12 provide visual representations of the addition and the transfer of the signal charges. In FIG. 6, for the sake of simplifying the description, an operation corresponding to only a segment where β=1 is depicted, and each exposure sequence is repeated twice ($\alpha_{High} = \alpha_{Low} = 2$). Meanwhile, in FIGS. 7 to 12, the directions in which the signal charges are read out and transferred are indicated by the corresponding arrows.

First, in strong exposure sequence K1 shown in FIG. 6, the voltages of φV1 and φV3 are each set to the High level, and the voltages of φV2 and φV4 are each set to the Low level. This produces a state in which the signal charges can be read out from four photoelectric converters 4 connected to V1 and V3 of corresponding vertical transferrer 5 in the odd number columns. In this example, the voltage of φSub is set to the Low level for exposure period Te in synchronization with the irradiation light, and thus signal charges 31 from four photoelectric converters 4 are each accumulated into corresponding vertical transferrer 5 in the odd number columns, as shown in (a) in FIG. 7. Each signal charge 31 includes irradiation light component 31a and background light component 31b. Signal charges 31 are accumulated separately in V1 and V3 of corresponding vertical transferrer 5. When the voltages of φV1, φV2, and φV3 are each set to the Middle level at time T1 shown in FIG. 6, signal charges 31 are turned into one packet, as shown in (b) in FIG. 7, and this means that the signal charges from four photoelectric converters 4 have been added. Thereafter, as shown in (c) in FIG. 7, signal charges 31 are transferred vertically in the forward direction (in the downward direction of the drawing) and become accumulated in V2 to V4.

Next, in weak exposure sequence J1 shown in FIG. 6, the voltages of φV2 and φV4 are each set to the High level, and the voltages of φV1 and φV3 are each set to the Low level. This produces a state in which the signal charges can be read out from four photoelectric converters 4 connected to V2 and V4 of corresponding vertical transferrer 5 in the even number columns. In this example, the voltage of φSub is set to the Low level for exposure period Te' in synchronization with the irradiation light, and thus signal charges 32 from four photoelectric converters 4 are each accumulated into corresponding vertical transferrer 5 in the even number columns, as shown in (a) in FIG. 8. Each signal charge 32 includes irradiation light component 32a and background light component 32b. Signal charges 31 and signal charges 32 are each accumulated separately in V2 and V4 of corresponding vertical transferrer 5. When the voltages of φV2, φV3, and φV4 are each set to the Middle level at time T2 shown in FIG. 6, signal charges 31 and signal charges 32 are each turned into one packet, as shown in (b) in FIG. 8. Thereafter, as shown in (c) in FIG. 8, signal charges 31 and signal charges 32 are each transferred vertically in the forward direction (in the downward direction of the drawing) and become accumulated in V5 and V6.

Next, in strong exposure sequence K2 shown in FIG. 6, solid-state image sensor 106 is driven in a manner similar to that in strong exposure sequence K1 with the starting time of the exposure period shifted. Thus, as shown in (a) in FIG. 9, signal charges 33 from four photoelectric converters 4 are each accumulated into corresponding vertical transferrer 5 in the odd number columns. At this point, since signal charges 31 have each been moved already to V5 and V6 through the foregoing transfer in the forward direction, signal charges 31 do not get mixed with signal charges 33. Each signal charge 33 includes irradiation light component 33a and background light component 33b. Signal charges 33 are accumulated separately in V1 and V3 of corresponding vertical transferrer 5. When the voltages of φV1, φV2, and φV3 are each set to the Middle level at time T3 shown in FIG. 6, signal charges 33 are turned into one packet, as shown in (b) in FIG. 9, and this means that the signal charges from four photoelectric converters 4 have been added. Thereafter, as shown in (c) in FIG. 9, signal charges 33 are transferred vertically in the forward direction (in the downward direction of the drawing) and become accumulated in V2 to V4.

Next, in weak exposure sequence J2 shown in FIG. 6, solid-state image sensor 106 is driven in a manner similar to that in weak exposure sequence J1 with the starting time of the exposure period shifted. Thus, as shown in (a) in FIG. 10, signal charges 34 from four photoelectric converters 4 are each accumulated into corresponding vertical transferrer 5 in the even number columns. At this point, since signal charges 32 have each been accumulated already in V5 and V6 through the foregoing transfer in the forward direction, signal charges 32 do not get mixed with signal charges 34. Each signal charge 34 includes irradiation light component 34a and background light component 34b. Signal charges 33 and signal charges 34 are each accumulated separately in V2 and V4 of corresponding vertical transferrer 5. When the voltages of φV2, φV3, and φV4 are each set to the Middle level at time T4 shown in FIG. 6, signal charges 33 and signal charges 34 are each turned into one packet, as shown in (b) in FIG. 10. Thereafter, as shown in (c) in FIG. 10, signal charges 33 and signal charges 34 are each transferred vertically in the forward direction (in the downward direction of the drawing) and become accumulated in V5 and V6.

Next, in background exposure sequence B0 shown in FIG. 6, solid-state image sensor 106 is driven in a manner similar to that in strong exposure sequence K1 without the irradiation by the infrared light source. Thus, as shown in (a) in FIG. 11, signal charges 35 from four photoelectric converters 4 are each accumulated into corresponding vertical transferrer 5 in the odd number columns. At this point, since signal charges 33 have each been moved already to V5 and V6 through the foregoing transfer in the forward direction, signal charges 33 do not get mixed with signal charges 35. Signal charges 35 are accumulated separately in V1 and V3 of corresponding vertical transferrer 5. When the voltages of φV1, φV2, and φV3 are each set to the Middle level at time T5 shown in FIG. 6, signal charges 35 are turned into one packet, as shown in (b) in FIG. 11, and this means that the signal charges from four photoelectric converters 4 have been added. Thereafter, as shown in (c) in FIG. 12, signal charges 31 to signal charges 35 are transferred vertically in the reverse direction (in the upward direction of the drawing), and this produces a state in which signal charges 31 and signal charges 32 are each accumulated in V1 to V3, that is, a state in which strong exposure sequence K1 can be executed again. The positions of signal charges 36 are empty packets and are not used.

Repeating the above-described operation P times makes it possible to accumulate the five types of signal charges with respect to reflection light 111 corresponding to one frame period into vertical transferrers 5 independently and with high sensitivity.

Because of the difference in the irradiation intensity of irradiation light 110 in strong exposure sequences K1 and K2 and in weak exposure sequences J1 and J2, signal charge amounts S0+BG and S1+BG and signal charge amounts S0'+BG and S1'+BG each have sensitivity difference to the reflectance of the object and the distance to the object.

Expression 1 and Expression 3 below are for a calculator that calculates the two types of distances z and z' in control arithmetic device 107 according to the present embodiment. When the speed of light is represented by c, distance z is calculated through Expression 1 by use of signal charges S0 and S1, in which the influence of the background light obtained in strong exposure sequences K1 and K2 and background exposure sequence B0 has been removed. In a similar manner, distance z' is calculated through Expression 3 by use of signal charges S0' and S1', in which the influence of the background light obtained in weak exposure sequences J1 and J2 and background exposure sequence B0 has been removed. In this example, the division cannot be carried out properly when S0 is at the zero level, and therefore distance z cannot be calculated. Moreover, when S0+BG and S1+BG are each at a saturation level, S0 and BG cannot be extracted properly, and therefore distance z cannot be calculated. In a similar manner, when S1 is at the zero level and S0'+BG and S1'+BG are each at a saturation level, distance z' cannot be calculated.

$$z=(c \times Tp/2) \times (S1/S0) \qquad \text{Expression 1 (reproduced)}$$

$$z'=(c \times Tp/2) \times (S1'/S0') \qquad \text{Expression 3}$$

Figure 18:
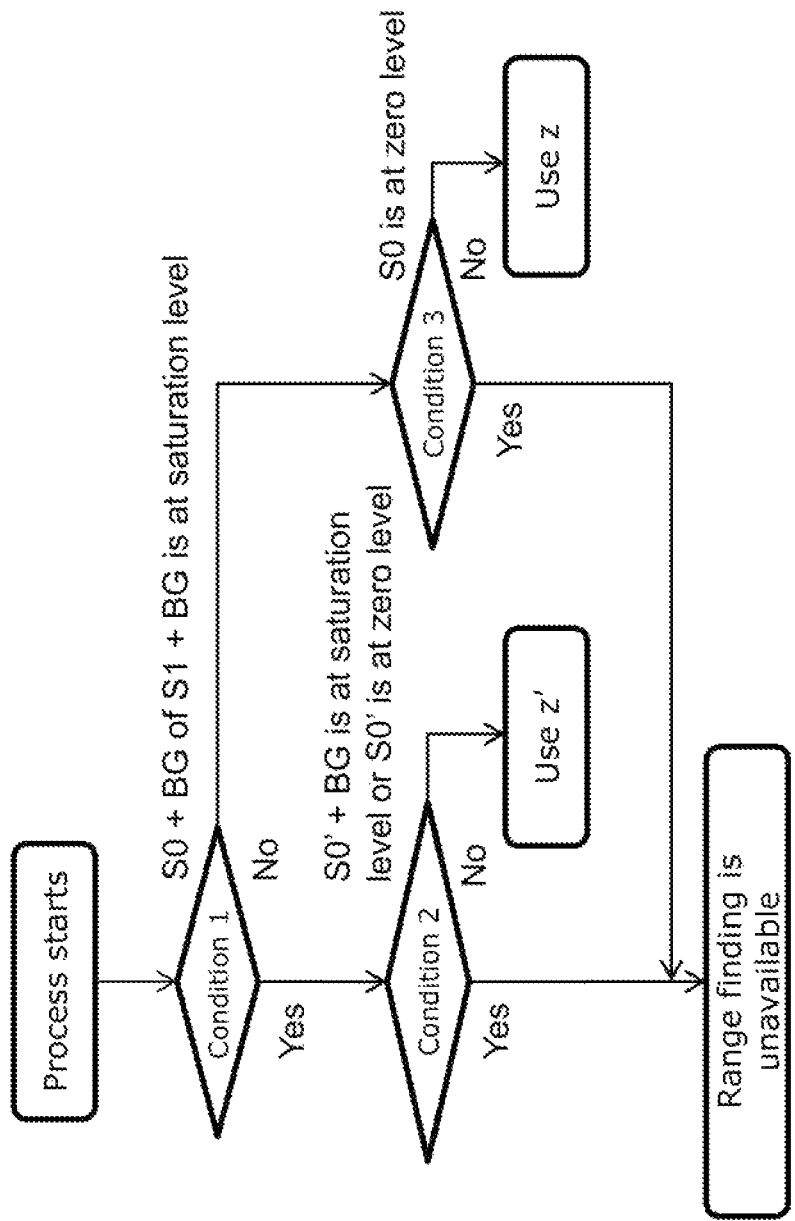
FIG. 18 is an illustration for describing a flow of selecting a distance signal according to Embodiment 3.

Therefore, control arithmetic device 107 selects as to which of the two types of distances z and z' should be calculated in accordance with the amount of the five types of signal charges. For example, as shown in FIG. 18, first, if S0+BG or S1+BG is at a saturation level at condition 1, the process proceeds to condition 2, otherwise the process proceeds to condition 3. Next, at condition 2, if S0'+BG is at a saturation level or S0' is at the zero level, it is determined that the range finding is not available, otherwise distance z' is adopted. Then, at condition 3, if S0 is at the zero level, distance z is adopted, otherwise it is determined that the range finding is not available.

As the distance calculator makes the selection as described above, the signal charge can be kept from reaching the saturation level or the zero level because of the influence of the reflectance of the object or the distance to the object, and the region where the range finding is not available can be kept to a minimum.

The operation described above makes it possible to accumulate the five types of signal charges independently in the vertical transferrers in one frame period. Moreover, since the signal charges from the four photoelectric converters are added, the sensitivity increases substantially twofold as compared with a conventional method in which the signal charges from two photoelectric converters are added. Therefore, any decrease in each charge amount associated with an increase in the number of types of signal charges to be accumulated can be canceled out. Accordingly, the distance calculator corresponding to the reflectance of the object or the distance to the object can be selected based on the five types of signal charges, and this makes it possible to achieve a range finding device that can be used in any shooting space.

Embodiment 4

An imaging device according to Embodiment 4 targets a light scattering body, such as an organism, as an object. To be more specific, the imaging device according to the present embodiment uses two types of infrared light having different peak wavelengths to detect, for example, the distribution of the amounts of changes in the blood flows in the outer layer of the skin and in the brain of a subject to be observed as well as the change over time in the distribution. Thus, a two-dimensional still image or a two-dimensional moving image showing the detected distribution can be generated. The use of the information obtained from such an image makes it possible to estimate the brain activity (e.g., the degree of concentration, the emotions, etc.) of the subject, for example.

The imaging device according to the present embodiment can detect the biometric information such as those described above contactlessly and within a single field. Therefore, the burden associated with the detection can be resolved, and the accuracy in detecting the information on the cerebral blood flow can be improved greatly, as compared to the existing techniques.

In the following, the imaging device according to the present embodiment that is capable of such detection with high accuracy will be described.

Figure 19:
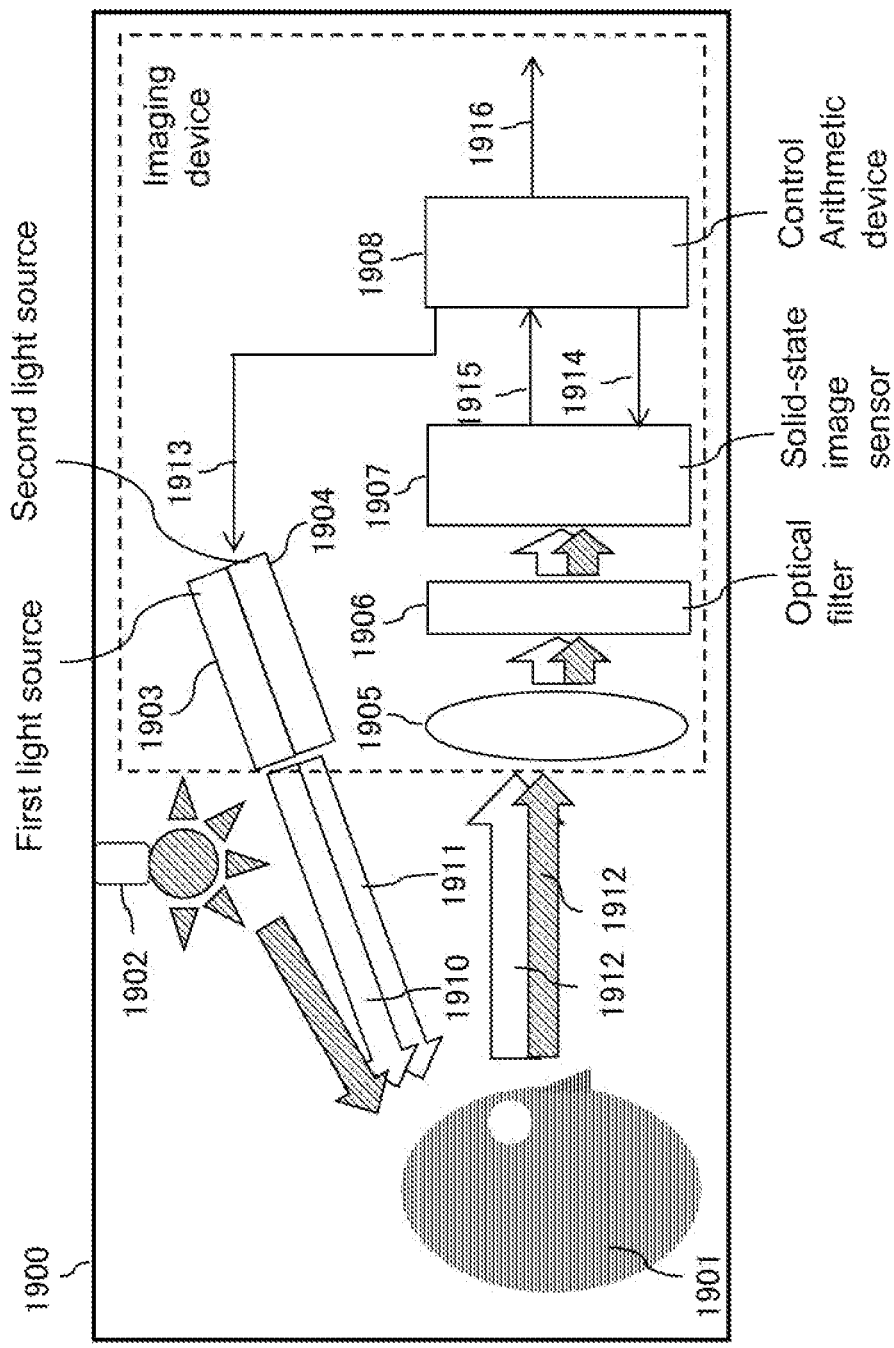
FIG. 19 is an illustration for describing a schematic configuration of a cerebral blood flow measuring device according to Embodiment 4.

FIG. 19 is a diagram schematically showing a configuration of the imaging device according to the present embodiment. FIG. 19 shows not only the imaging device but also object 1901 (the head of a human) to be subjected to the detection and shooting space 1900.

The present embodiment differs from Embodiments 1 to 3 in that two light sources that each emit a pulsed light at a different wavelength are used. In the example described below, the information on hemoglobin in the blood flow will be obtained by use of the imaging device according to Embodiment 4.

The imaging device according to the present embodiment includes first light source 1903, second light source 1904, optical system 1905, optical filter 1906, solid-state image sensor 1907, and control arithmetic device 1908.

First light source 1903 and second light source 1904 each emit a pulsed light toward the position where object 1901 is located. In the present embodiment, first light source 1903 is a laser light source that emits a narrow band pulsed light having a center wavelength of 750 nm, and second light source 1904 is a laser light source that emits a narrow band pulsed light having a center wavelength of 850 nm. Reflection light component 1912 from object 1901 enters optical system 1905. Reflection light component 1912 includes light reflected by the surface of object 1901 and light diffused inside object 1901 and then reflected by object 1901. Optical filter 1906 is disposed between optical system 1905 and solid-state image sensor 1907. Optical filter 1906 mainly transmits only light at a wavelength corresponding to the wavelength of the light from first light source 1903 and light at a wavelength corresponding to the light from second light source 1904. Control arithmetic device 1908 is connected to first light source 1903, second light source 1904, and solid-state image sensor 1907 and controls the operation of first light source 1903, second light source 1904, and solid-state image sensor 1907. To be more specific, control arithmetic device 1908 controls emission timing 1913 of first light source 1903 and second light source 1904 so that emission timing 1913 synchronizes with timing 1914 at which a signal is accumulated in and discharged from each pixel of solid-state image sensor 1907.

Control arithmetic device 1908 is connected to solid-state image sensor 1907. Control arithmetic device 1908 generates image data 1916 (e.g., data of a two-dimensional moving image) based on electric signal 1915 output from solid-state image sensor 1907 and outputs generated image data 1916. The generated image data may be sent, for example, to a display (not illustrated), and an image showing the state of the cerebral blood flow may be displayed on the display.

This makes it possible to detect the information on the blood flow in the scalp and in the brain in the organism with high accuracy and, in particular, to detect the amount of change in oxyhemoglobin and deoxyhemoglobin included in the blood flow.

In the following, each constituent element and its operation will be described in detail.

First light source 1903 according to the present embodiment is a pulsed laser light source that emits a narrow band pulsed light having a center wavelength of 750 nm, and second light source 1904 according to the present embodiment is a pulsed laser light source that emits a narrow band pulsed light having a center wavelength of 850 nm. As will be described later, first light source 1903 and second light source 1904 each emit light pulses repeatedly in a predetermined pattern determined by control arithmetic device 1908. Each light pulse emitted by first light source 1903 and second light source 1904 may be, for example, light of a rectangular wave of which the rising time in which the pulse starts to rise and completes the rise and a falling time in which the pulse starts to fall and completes the fall is close to zero.

First light source 1903 and second light source 1904 may each be a light source, such as a laser diode (LD), in which the rise of a light pulse and the fall of a light pulse is close to being perpendicular to the time axis (i.e., the time response property is rapid). First light source 1903 and second light source 1904 may each be implemented by any type of light source that emits a pulsed light, and examples of such a light source include a semiconductor laser, a solid-state laser, and a fiber laser.

In the imaging device according to the present embodiment, first light source 1903 and second light source 1904 that take into consideration an influence on a retina is used since object 1901 is a human body. For example, in a case where a laser light source is used, a light source that satisfies Class 1 of the laser safety standards defined in the applicable country may be used. When Class 1 is satisfied, object 1901 is irradiated with light having a low luminous intensity where the accessible emission limit (AEL) falls below 1 mW. Even if first light source 1903 and second light source 1904 do not themselves satisfy Class 1, Class 1 may be satisfied through a combination with other optical elements. For example, an element, such as a diffuser or a neutral density (ND) filter, may be disposed between object 1901 and first light source 1903 or second light source 1904, and Class 1 of the laser safety standards may be satisfied as the light is diffused or attenuated by such an element.

The wavelength of the light emitted by first light source 1903 and the wavelength of the light emitted by second light source 1904 are not limited to 750 nm and 850 nm, respectively. For example, light having a desired wavelength included in the wavelength range of greater than or equal to 650 nm and less than or equal to 950 nm (i.e., infrared light or near-infrared light) may be used. The wavelength range stated above is referred to as a "biological window" and has a property that makes such light absorbed relatively less by the moisture in an organism and the skin of the organism. In a case where an organism serves as the subject of detection, the detection sensitivity can be increased by use of the light in the wavelength range described above. In a case where a change in the blood flow in the skin and in the brain of object 1901 is detected, as in the present embodiment, the light used is conceivably absorbed mainly by oxyhemoglobin and deoxyhemoglobin, and the degree of absorption of the light differs for different wavelengths. When a change occurs in the blood flow, the concentration of oxyhemoglobin and deoxyhemoglobin changes conceivably, and the degree of absorption of the light also changes. Accordingly, the amount of light detected before and after the change in the blood flow also changes.

In the present disclosure, object 1901 is not limited to an organism. For example, any other types of light scattering bodies, such as a gas, a drug, or a food, can also serve as object 1901. The wavelength range of the light emitted by first light source 1903 and second light source 1904 is not limited to the wavelength range of near-infrared radiation (greater than or equal to about 700 nm and less than or equal to about 2500 nm). For example, the wavelength range of the light emitted by first light source 1903 and second light source 1904 may be a wavelength range of visible light (greater than or equal to about 400 nm and less than or equal to about 700 nm) or a wavelength range of ultraviolet radiation (greater than or equal to about 10 nm and less than or equal to about 400 nm). Depending on the intended use, an electromagnetic wave in a radio spectrum, such as mid-infrared radiation, far-infrared radiation, terahertz waves, or millimeter waves, can also be used.

Figure 20:
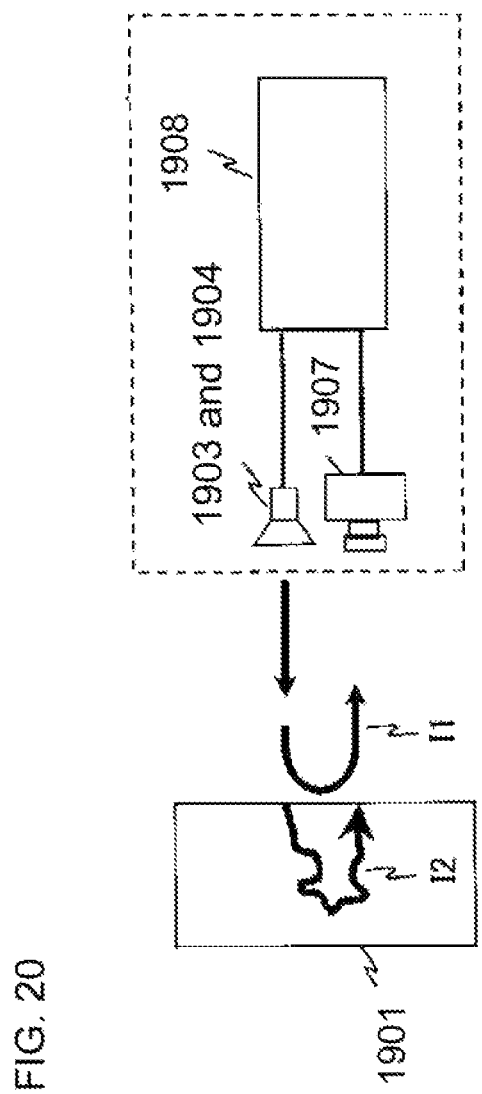
FIG. 20 is a diagram showing surface reflection and internal diffusion of an object.

As shown in FIG. 20, the light that has been emitted from first light source 1903 and second light source 1904 and has reached object 1901 is separated into surface reflection component I1 that has been reflected by the surface of object 1901 and internal scattering component I2 that has been reflected or scattered once inside object 1901 or scattered multiple times inside object 1901. Surface reflection component I1 includes two components, namely a direct reflection component and a diffuse reflection component. The direct reflection component is a component reflected at an angle of reflection equal to the angle of incidence. The diffuse reflection component is a component diffused and reflected in accordance with the uneven shape of the surface.

In the present disclosure, surface reflection component I1 reflected by the surface of object 1901 includes these two components described above. Meanwhile, internal scattering component I2 includes a component scattered and reflected by internal tissues near the surface of object 1901. The traveling direction of surface reflection component I1 and the traveling direction of internal scattering component I2 change upon reflection or scattering.

At this point, a large part of the energy of the light that has hit the head serving as object 1901 and that has wavelengths of 750 nm and 850 nm is reflected by the surface of object 1901. However, a small part of the energy reaches a deep part of object 1901 while being scattered and continues to travel while being further scattered, and a very small amount of its energy component containing more internal scattering component reaches the surface of the forehead of the head again. A part of that light is transmitted through optical system 1905 and optical filter 1906 and reaches solid-state image sensor 1907.

In this example, since it takes some time for the light to reach the deep part of object 1901 while being scattered, it is very important that a signal obtained from the exposure of the vicinity of the rise of the reflection light include a large amount of information on the surface of object 1901 and that a signal obtained from the exposure of the vicinity of the fall of the reflection light include a large amount of information on the deep part of object 1901.

Optical system 1905 according to the present embodiment may be for imaging the light on solid-state image sensor 1907 with high efficiency. Optical system 1905 may be a combination of a plurality lenses or may be a single lens. Moreover, optical system 1905 may be a telecentric optical system. Furthermore, a fisheye lens or a wide angle lens may be used to control the angle of view of the object, or a zoom lens may be used. In addition, a pupil may be set in front of, in the middle of, or behind a lens in order to control the brightness.

Figure 21:
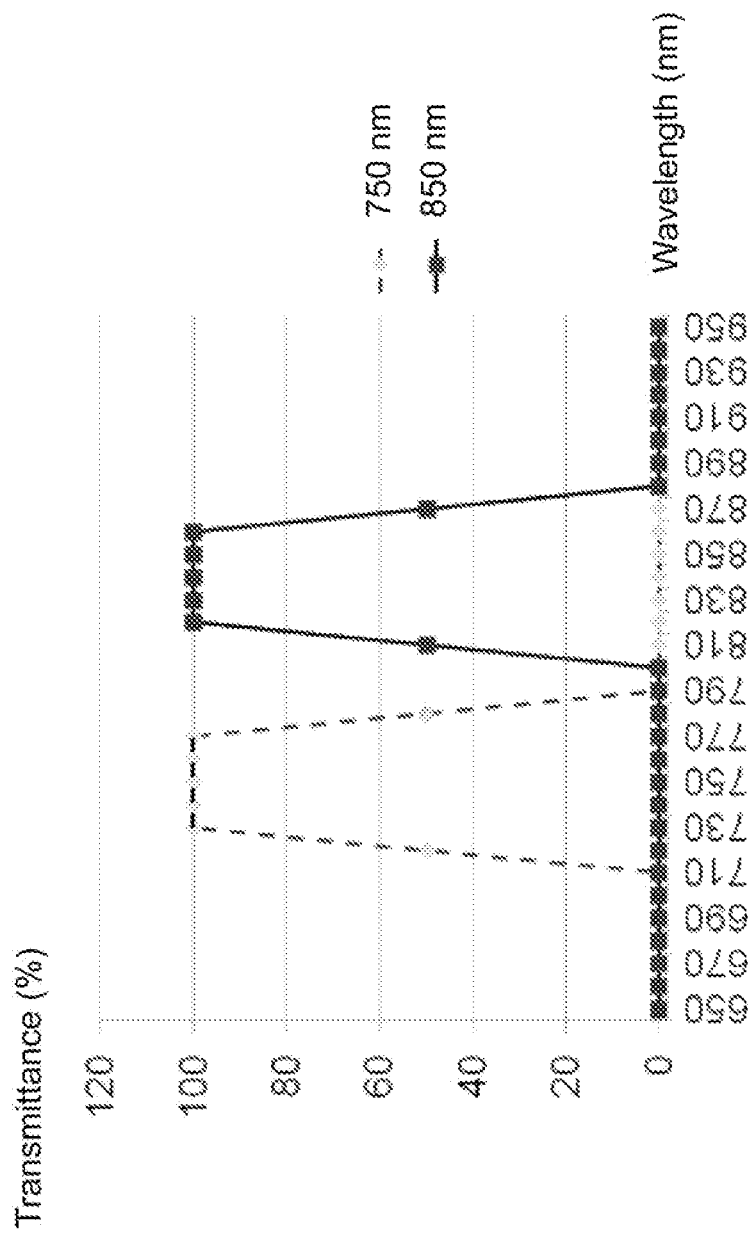
FIG. 21 shows a graph of transmission characteristics of an optical filter of the cerebral blood flow measuring device according to Embodiment 4.

FIG. 21 is a graph showing an example of the spectral transmittance of optical filter 1906. As shown in FIG. 21, optical filter 1906 transmits a narrow band light having a center wavelength of 750 nm emitted from first light source 1903 and a narrow band light having a center wavelength of 850 nm emitted from second light source 1904 and blocks light having any other wavelength. Disposing such optical filter 1906 makes it possible to keep any external disturbance light (e.g., background light) from entering solid-state image sensor 1907.

Solid-state image sensor 1907 receives the light that has been emitted from first light source 1903 and second light source 1904 and reflected by object 1901. Solid-state image sensor 1907 includes a plurality of pixels arrayed two-dimensionally on its imaging surface and acquires two-dimensional information on the inside of object 1901. For example, solid-state image sensor 1907 may be a CCD image sensor or a CMOS image sensor.

Solid-state image sensor 1907 includes an electronic shutter. The electronic shutter is a circuit that controls the shutter duration corresponding to the length of an exposure period that is a period of one instance of signal accumulation in which a received light is converted into a valid electric signal and accumulated, and the circuit also controls the time from when one exposure period ends to when the next exposure period starts. In the present embodiment, the state in which the electronic shutter is in the exposure is indicated as "OPEN", and the state in which the electronic shutter is not in the exposure is indicated as "CLOSED". Solid-state image sensor 1907 can adjust, by use of the electronic shutter, the time from when one exposure period ends to when the next exposure period starts with the time scale of a sub-nanosecond (e.g., from 30 ps to 1 ns).

In the use in which object 1901 is, for example, a human forehead and information on the cerebral blood flow or the like is to be detected, the attenuation rate of the light inside object 1901 is very high, and the light may be attenuated to about one-millionth the original light, for example. Therefore, an irradiation with a single pulse may not provide the amount of light sufficient to detect internal scattering component I2. In this case, first light source 1903 and second light source 1904 each emit a plurality of light pulses, and solid-state image sensor 1907 may perform the exposure a plurality of times accordingly by use of the electronic shutter in accordance with the emitted plurality of light pulses. Such an operation allows detection signals to be integrated and can improve the sensitivity.

FIG. 4A is a configuration diagram of the solid-state image sensor according to the present embodiment. Although the configuration of the solid-state image sensor according to the present embodiment is similar to the configuration of the solid-state image sensor according to Embodiment 1, they differ in the operation. In FIG. 4A, only four pixels in the vertical direction and only four pixels in the horizontal direction are depicted for the sake of simplifying the drawing.

The solid-state image sensor according to the present embodiment includes a plurality of photoelectric converters (photodiodes) 4, vertical transferrers 5, horizontal transferrer 10, and charge detector 11. The plurality of photoelectric converters 4 are disposed in a matrix on a semiconductor substrate and each convert a received right into a signal charge. Vertical transferrers 5 each accumulate signal charges read out from corresponding photoelectric converters 4 and transfers the signal charges in the row direction (in the vertical direction). Horizontal transferrer 10 transfers the signal charges transferred by vertical transferrers 5 into the column direction (in the horizontal direction). Charge detector 11 outputs the signal charges transferred by horizontal transferrer 10.

In this example, the solid-state image sensor is an interline transfer CCD. For example, vertical transferrers 5 are each a ten-phase drive system with ten gates of vertical transfer electrodes 8 per two photoelectric converters 4 that are adjacent in the vertical direction, and horizontal transferrer 10 is a two-phase drive system. Of vertical transfer electrodes 8, $\varphi V1$ and $\varphi V3$ serve also as readout electrodes for four photoelectric converters 4 connected to corresponding vertical transferrer 5 in the odd number columns, and $\varphi V2$ and $\varphi V4$ serve also as readout electrodes for four photoelectric converters 4 connected to corresponding vertical transferrer 5 in the even number columns. With this configuration, the signal charges accumulated in four photoelectric converters 4 are added and read out to the position indicated, for example, by corresponding signal packet 9a of each vertical transferrer 5 in the odd number columns when a high voltage is being applied to $\varphi V1$ and $\varphi V3$ or added and read out to the position indicated, for example, by corresponding signal packet 9b of each vertical transferrer 5 in the even number columns when a high voltage is being applied to $\varphi V2$ and $\varphi V4$. Thereafter, the signal charges in vertical transferrers 5 are transferred in the column direction upon a voltage being applied to vertical transfer electrodes 8.

Photoelectric converters 4 are provided with vertical overflow drain (VOD) 12 for sweeping the signal charges. Although VOD 12 is depicted in the lateral direction of the pixels in order to facilitate the understanding of the present disclosure, VOD 12 extends in the bulk direction of the pixels (in the depthwise direction of the semiconductor substrate) in reality. Upon a high voltage being applied to electrode $\varphi$Sub connected to the substrate of VOD 12, the signal charges in all photoelectric converters 4 are discharged at once to the substrate.

Figure 22A:
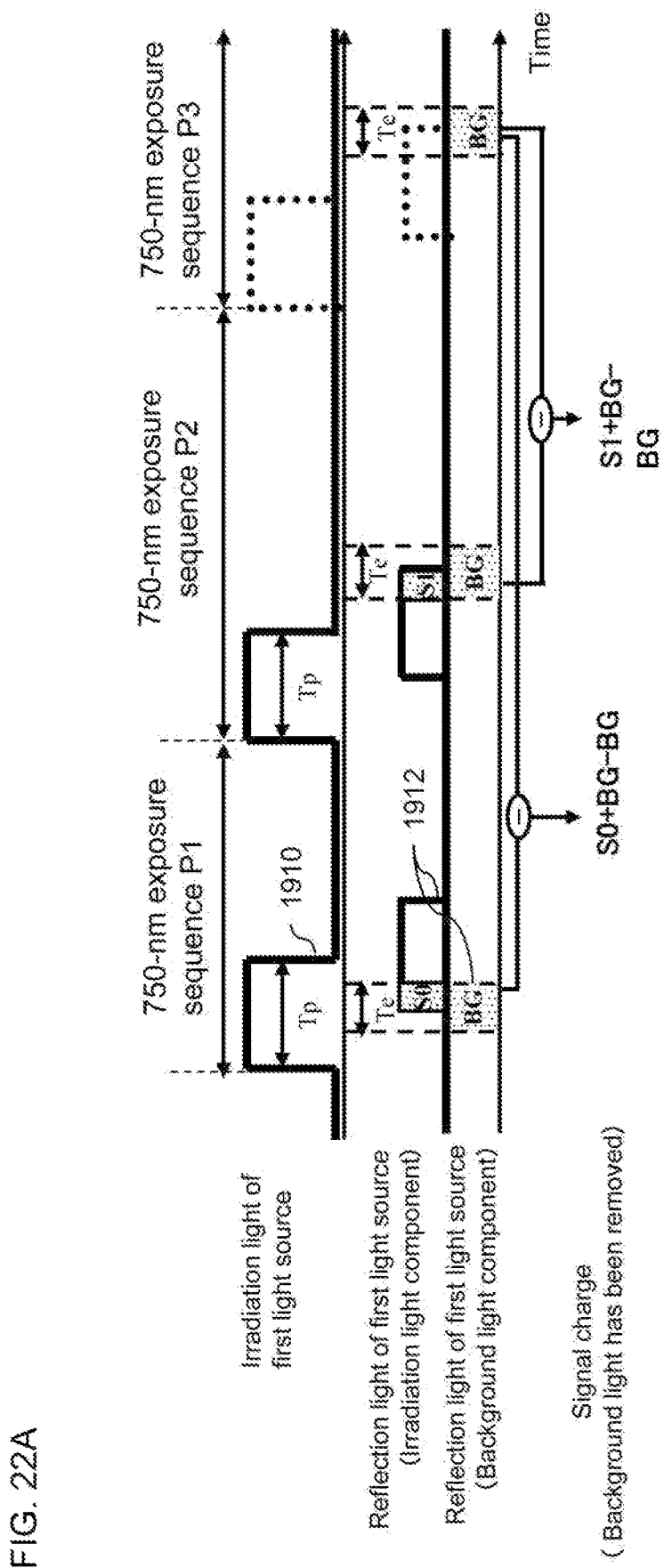
FIG. 22A is an illustration for describing an operation timing example and an operation principle of the cerebral blood flow measuring device according to Embodiment 4.
Figure 22B:
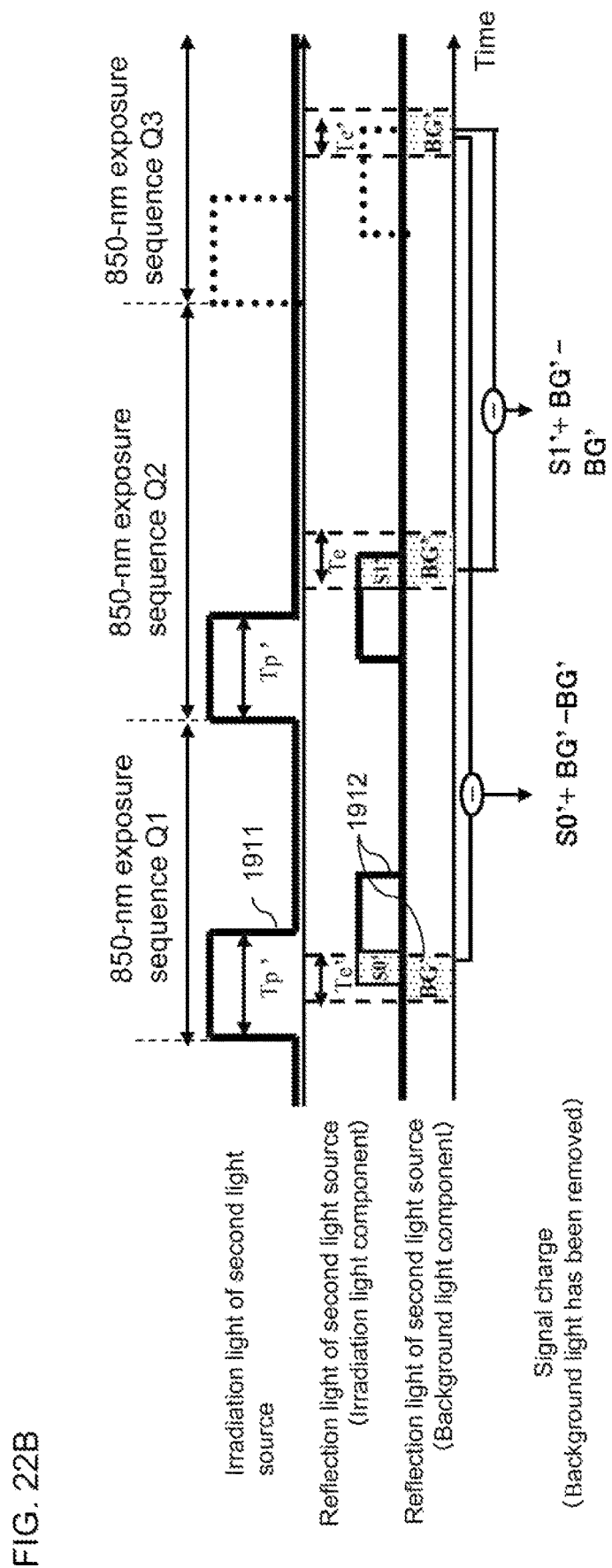
FIG. 22B is an illustration for describing another operation timing example and an operation principle of the cerebral blood flow measuring device according to Embodiment 4.

FIGS. 22A and 22B are illustrations for describing an operation timing and an operation principle of the cerebral blood flow measuring device according to Embodiment 4. The operation includes a total of six types of exposure sequences, namely 750-nm sequences P1 to P3 and 850-nm sequences Q1 to Q3, and two types of signals are calculated based on the signal charge amount obtained in each of the exposure sequences. In this example, the pulse duration (the irradiation time) of irradiation light 1910 at a wavelength of 750 nm is denoted by Tp, and the pulse duration (the irradiation time) of irradiation light 1911 at a wavelength of 850 nm is denoted by Tp'. The length of the exposure period of each of 750-nm sequences P1 to P3 is denoted by Te, the exposure period of each of 850-nm sequences Q1 to Q3 is denoted by Te', the background light component included in the reflection light of the first light source in each of 750-nm sequences P1 to P3 is denoted by BG, and the background light component included in the reflection light of the second light source in each of 850-nm sequences Q1 to Q3 is denoted by BG'.

First, as shown in FIG. 22A, in 750-nm sequence P1, exposure period Te includes the rise and its vicinity of reflection light 1912 of irradiation light 1910 emitted from first light source 1903, and the amount of the signal charge based on reflection light 1912 is S0+BG. Meanwhile, in 750-nm sequence P2, exposure period Te includes the fall and its vicinity of reflection light 1912 of irradiation light 1910 emitted from first light source 1903, and the amount of the signal charge based on reflection light 1912 is S1+BG. Moreover, since there is no irradiation light 1910 in 750-nm sequence P3, the amount of the signal charge based on reflection light 1912 is BG. Accordingly, signal charges S0 and S1 that are not dependent on the background light can be extracted by subtracting BG from each of S0+BG and S1+BG.

In a similar manner, as shown in FIG. 22B, in 850-nm sequence Q1, exposure period Te' includes the rise and its vicinity of reflection light 1912 of irradiation light 1911 emitted from second light source 1904, and the amount of the signal charge based on reflection light 1912 is S0'+BG'. Meanwhile, in 850-nm sequence Q2, exposure period Te' includes the fall and its vicinity of reflection light 1912 of irradiation light 1911 emitted from second light source 1904, and the amount of the signal charge based on reflection light 1912 is S1'+BG'. Moreover, since there is no irradiation light 1911 in 850-nm sequence Q3, the amount of the signal charge based on reflection light 1912 is BG'. Accordingly, signal charges S0' and S1' that are not dependent on the background light can be extracted by subtracting BG' from each of S0'+BG' and S1'+BG'.

Figure 22C:
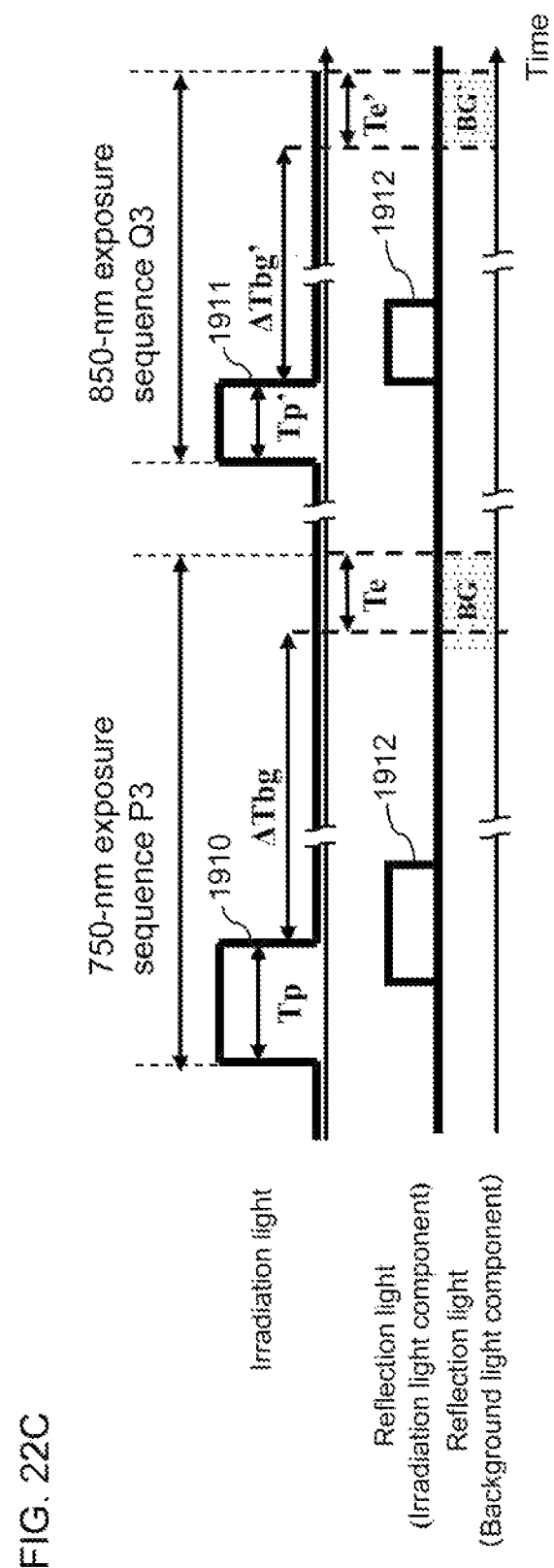
FIG. 22C is an illustration for describing yet another operation timing example and an operation principle of the cerebral blood flow measuring device according to Embodiment 4.

In the example shown in FIGS. 22A and 22B, no light is emitted from first light source 1903 or second light source 1904 in 750-nm sequence P3 or in 850-nm sequence Q3. Alternatively, as shown in FIG. 22C, the irradiation may be performed, and the starting time of the exposure period may be delayed by times ΔTbg and ΔTbg' in which the irradiation light component included in reflection light 1912 is attenuated to a negligible level to thus expose solid-state image sensor 1907 to only the background light component.

Figure 23:
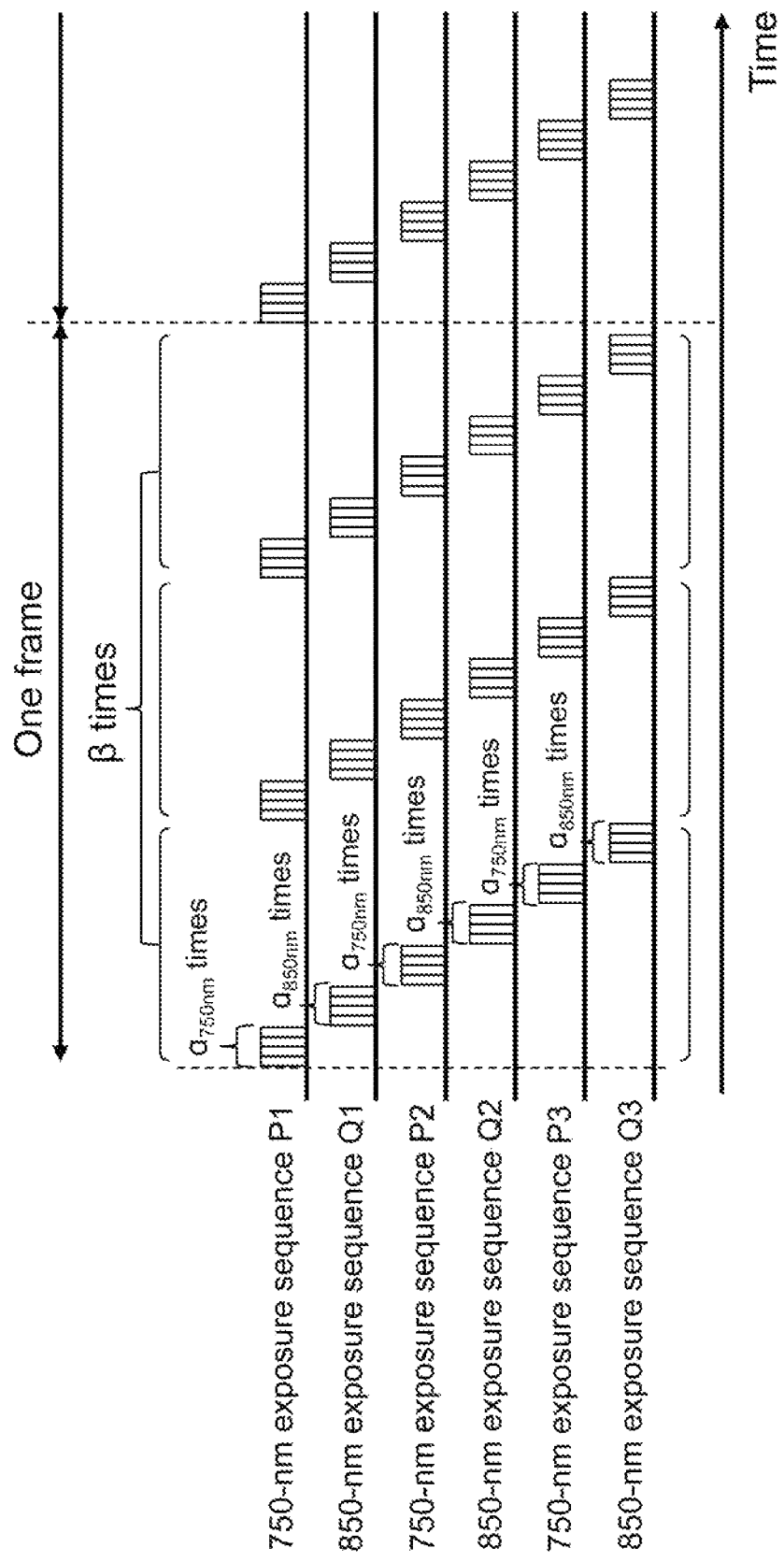
FIG. 23 is an illustration for describing an operation timing of the cerebral blood flow measuring device according to Embodiment 4.

Moreover, each exposure sequence is shown only once in FIGS. 22A and 22B for the sake of simplifying the description. In implementation, however, as shown in FIG. 23, 750-nm sequences P1 to P3 are repeated $\alpha_{750\,nm} \times \beta$ times in one frame period, and 850-nm sequences Q1 to Q3 are repeated $\alpha_{850\,nm} \times \beta$ times, in order to obtain a sufficient amount of signal charges from the standpoint of the S/N ratio. In this example, the level difference associated with the power of each light or the sensitivity or the like of the solid-state image sensor can be corrected by setting $\alpha_{750\,nm}$ and $\alpha_{850\,nm}$ independently in 750-nm sequences P1 to P3 and 850-nm sequences Q1 to Q3.

Figure 24:
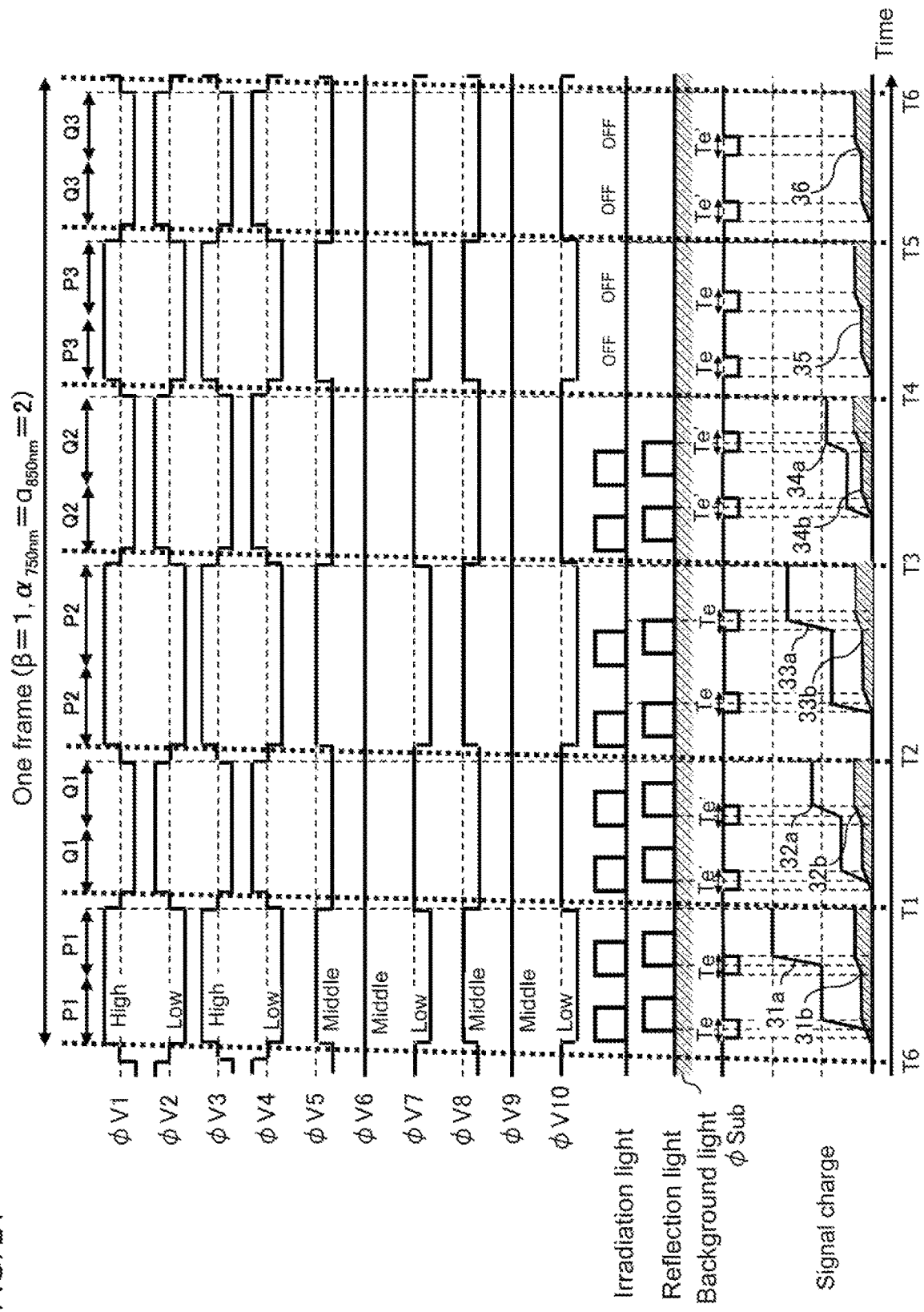
FIG. 24 is an illustration for describing a drive timing of a photoelectric converter and a vertical transferrer according to Embodiment 4.

Next, with reference to FIG. 24 and FIGS. 7 to 12, an operation timing of the solid-state image sensor shown in FIG. 4A will be described. FIG. 24 shows an example of a drive timing of photoelectric converters 4 and vertical transferrers 5 in the six types of exposure sequences constituting one frame period. FIGS. 7 to 12 provide visual representations of the addition and the transfer of the signal charges. In FIG. 24, for the sake of simplifying the description, an operation corresponding to only a segment where β=1 is depicted, and each exposure sequence is repeated twice ($\alpha_{750\,nm} = \alpha_{850\,nm} = 2$). Meanwhile, in FIGS. 7 to 12, the directions in which the signal charges are read out and transferred are indicated by corresponding arrows.

First, in 750-nm sequence P1 shown in FIG. 24, the voltages of φV1 and φV3 are each set to the High level, and the voltages of φV2 and φV4 are each set to the Low level. This produces a state in which the signal charges can be read out from four photoelectric converters 4 connected to V1 and V3 of corresponding vertical transferrer 5 in the odd number columns. In this example, the voltage of φSub is set to the Low level for exposure period Te in synchronization with the irradiation light, and thus signal charges 31 from four photoelectric converters 4 are each accumulated into corresponding vertical transferrer 5 in the odd number columns, as shown in (a) in FIG. 7. Each signal charge 31 includes irradiation light component 31a and background light component 31b. Signal charges 31 are accumulated separately in V1 and V3 of corresponding vertical transferrer 5. When the voltages of φV1, φV2, and φV3 are each set to the Middle level at time T1 shown in FIG. 24, signal charges 31 are turned into one packet, as shown in (b) in FIG. 7, and this means that the signal charges from four photoelectric converters 4 have been added. Thereafter, as shown in (c) in FIG. 7, signal charges 31 are transferred vertically in the forward direction (in the downward direction of the drawing) and become accumulated in V2 to V4.

Next, in 850-nm sequence Q1 shown in FIG. 24, the voltages of φV2 and φV4 are each set to the High level, and the voltages of φV1 and φV3 are each set to the Low level. This produces a state in which the signal charges can be read out from four photoelectric converters 4 connected to V2 and V4 of corresponding vertical transferrer 5 in the even number columns. In this example, the voltage of φSub is set to the Low level for exposure period Te' in synchronization with the irradiation light, and thus signal charges 32 from four photoelectric converters 4 are each accumulated into corresponding vertical transferrer 5 in the even number columns, as shown in (a) in FIG. 8. Each signal charge 32 includes irradiation light component 32a and background light component 32b. Signal charges 31 and signal charges 32 are each accumulated separately in V2 and V4 of corresponding vertical transferrer 5. When the voltages of φV2, φV3, and φV4 are each set to the Middle level at time T2 shown in FIG. 24, signal charges 31 and signal charges 32 are each turned into one packet, as shown in (b) in FIG. 8. Thereafter, as shown in (c) in FIG. 8, signal charges 31 and signal charges 32 are each transferred vertically in the forward direction (in the downward direction of the drawing) and become accumulated in V5 and V6.

Next, in 750-nm sequence P2 shown in FIG. 24, solid-state image sensor 1907 is driven in a manner similar to that in 750-nm sequence P1 with the starting time of the exposure period shifted. Thus, as shown in (a) in FIG. 9, signal charges 33 from four photoelectric converters 4 are each accumulated into corresponding vertical transferrer 5 in the odd number columns. At this point, since signal charges 31 have each been moved already to V5 and V6 through the foregoing transfer in the forward direction, signal charges 31 do not get mixed with signal charges 33. Each signal charge 33 includes irradiation light component 33a and background light component 33b. Signal charges 33 are accumulated separately in V1 and V3 of corresponding vertical transferrer 5. When the voltages of φV1, φV2, and φV3 are each set to the Middle level at time T3 shown in FIG. 24, signal charges 33 are turned into one packet, as shown in (b) in FIG. 9, and this means that the signal charges from four photoelectric converters 4 have been added. Thereafter, as shown in (c) in FIG. 9, signal charges 33 are transferred vertically in the forward direction (in the downward direction of the drawing) and become accumulated in V2 to V4.

Next, in 850-nm sequence Q2 shown in FIG. 24, solid-state image sensor 1907 is driven in a manner similar to that in 850-nm sequence Q1 with the starting time of the exposure period shifted. Thus, as shown in (a) in FIG. 10, signal charges 34 from four photoelectric converters 4 are each accumulated into corresponding vertical transferrer 5 in the even number columns. At this point, since signal charges 32 have each been accumulated already in V5 and V6 through the foregoing transfer in the forward direction, signal charges 32 do not get mixed with signal charges 34. Each signal charge 34 includes irradiation light component 34a and background light component 34b. Signal charges 33 and signal charges 34 are each accumulated separately in V2 and V4 of corresponding vertical transferrer 5. When the voltages of φV2, φV3, and φV4 are each set to the Middle level at time T4 shown in FIG. 24, signal charges 33 and signal charges 34 are each turned into one packet, as shown in (b) in FIG. 10. Thereafter, as shown in (c) in FIG. 10, signal charges 33 and signal charges 34 are each transferred vertically in the forward direction (in the downward direction of the drawing) and become accumulated in V5 and V6.

Next, in 750-nm sequence P3 shown in FIG. 24, solid-state image sensor 1907 is driven in a manner similar to that in 750-nm sequence P1 without the irradiation by the infrared light source. Thus, as shown in (a) in FIG. 11, signal charges 35 from four photoelectric converters 4 are each accumulated into corresponding vertical transferrer 5 in the odd number columns. At this point, since signal charges 33 have each been moved already to V5 and V6 through the foregoing transfer in the forward direction, signal charges 33 do not get mixed with signal charges 35. Signal charges 35 are accumulated separately in V1 and V3 of corresponding vertical transferrer 5. When the voltages of φV1, φV2, and φV3 are each set to the Middle level at time T5 shown in FIG. 24, signal charges 35 are turned into one packet, as shown in (b) in FIG. 11, and this means that the signal charges from four photoelectric converters 4 have been added. Thereafter, as shown in (c) in FIG. 11, signal charges 35 are transferred vertically in the forward direction (in the downward direction of the drawing) and become accumulated in V2 to V4.

Lastly, in 850-nm sequence Q3 shown in FIG. 24, solid-state image sensor 1907 is driven in a manner similar to that in 850-nm sequence Q1 without the irradiation by the infrared light source. Thus, as shown in (a) in FIG. 12, signal charges 36 from four photoelectric converters 4 are each accumulated into corresponding vertical transferrer 5 in the even number columns. At this point, since signal charges 34 have each been accumulated already in V5 and V6 through the foregoing transfer in the forward direction, signal charges 34 do not get mixed with signal charges 36. Signal charges 35 and signal charges 36 are each accumulated separately in V2 and V4 of corresponding vertical transferrer 5. When the voltages of φV2, φV3, and φV4 are each set to the Middle level at time T6 shown in FIG. 24, signal charges 35 and signal charges 36 are each turned into one packet, as shown in (b) in FIG. 12. Thereafter, as shown in (c) in FIG. 12, signal charges 31 to signal charges 36 are transferred vertically in the reverse direction (in the upward direction of the drawing), and this produces a state in which signal charges 31 and signal charges 32 are accumulated in V1 to V3. This allows 750-nm sequence P1 to be executed again, and the operation is repeated β times.

In this manner, highly accurate S0 and S0' that include a large amount of information on the surface of object 1901 and highly accurate S1 and S1' that include a large amount of information on the deep part of object 1901 are output from the solid-state image sensor.

In the example described in the present embodiment, solid-state image sensor 1907 is a CCD image sensor. Alternatively, solid-state image sensor 1907 may be a CMOS image sensor, a single photon counting image sensor, or an amplification-type image sensor, such as an electron multiplying CCD (EMCCD) image sensor or an intensified CCD (ICCD) image sensor.

Control arithmetic device 1908 may be, for example, a combination of a microprocessor, a memory, and a hardware logic circuit or an integrated circuit, such as a microcontroller with built-in processor and memory.

The hardware logic circuit may be, for example but not limited to, a programmable logic device (PLD), such as a digital signal processor (DSP) or a field programmable gate array (FPGA).

Control arithmetic device 1908 also controls the on and off of first light source 1903 and second light source 1904, the imaging by solid-state image sensor 1907, and the arithmetic operation process of signals from the solid-state image sensor.

The signal processor of control arithmetic device 1908 is a circuit that processes an image signal output from solid-state image sensor 1907. In the present embodiment, the signal processor of control arithmetic device 1908 generates moving image data that indicates the change over time in the blood flow in the skin and in the brain based on the signal output from solid-state image sensor 1907. Such moving image data is not a limiting example, and the signal processor of control arithmetic device 1908 may generate any other kind of information. For example, the signal processor of control arithmetic device 1908 may generate, by operating in synchronization with another device, biometric information on, for example but not limited to, the blood flow volume in the brain, the blood pressure, the saturation of peripheral oxygen, or the heart rate.

It is known that there is a close link between a change in the cerebral blood flow volume or in a component in the blood flow (e.g., hemoglobin) and the nerve activity of a human. For example, the activity of the nerve cells changes in response to a change in the emotion of a human, and the cerebral blood flow volume or the component in the blood flow changes accordingly. Therefore, the psychological state of a subject can be estimated if the biometric information, such as a change in the cerebral blood flow volume or in the component in the blood flow, can be measured. Examples of the psychological state of a subject include a feeling (e.g., feeing comfortable or uncomfortable), an emotion (e.g., feeling a sense of relief, anxious, sad, angry, etc.), a health condition (e.g., feeling well or tired), a thermal sense (e.g., feeling hot, cold, or humid). Stemming from the above, the index indicating the degree of the brain activity, such as the degree of mastery, the proficiency, or the degree of concentration, is also included in the psychological state. The signal processor of control arithmetic device 1908 may estimate the psychological state, such as the degree of concentration, of the subject based on the change in the cerebral blood flow volume or the like and output a signal indicating the result of the estimation.

Signals S0 and S0' transmitted from solid-state image sensor 1907 to control arithmetic device 1908 and obtained through the exposure of the rise and its vicinity of the reflection light accumulated on a frame by frame basis include mainly information on the change in the blood flow in the skin, and signals S1 and S1' obtained through the exposure of the fall and its vicinity of the reflection light include mainly information on the change in the blood flow in the skin and in the brain. Therefore, the information on the change in the blood flow in the brain alone can be extracted by separating the information on the change in the blood flow in the brain from the information on the change in the blood flow in the skin by use of the aforementioned signals.

Figure 25:
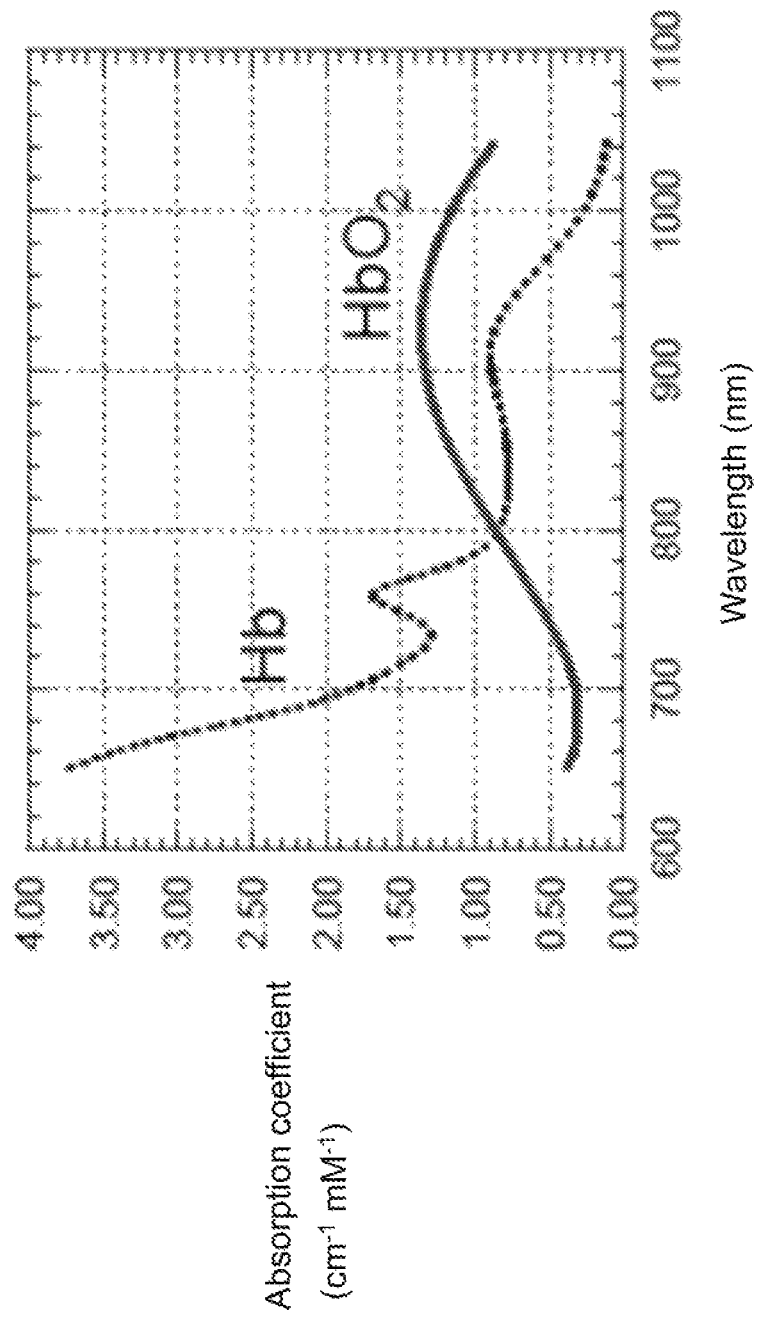
FIG. 25 shows a graph of a molar absorption spectrum of oxyhemoglobin and deoxyhemoglobin in a near-infrared range.

As shown in FIG. 25, the use of the light sources at two wavelengths of 750 nm and 850 nm can show that the molar absorption coefficients of infrared radiation in oxyhemoglobin (the solid line for $HbO_2$) and deoxyhemoglobin (the solid line for Hb) flip at 805 nm, and irradiating a subject with two wavelengths of around 805 nm and analyzing the reflection light thereof make it possible to obtain the amount of change in oxyhemoglobin and deoxyhemoglobin. It is to be noted that FIG. 25 is taken from "Chapter 3 Light Contributing to Healthy Living, 3 Noninvasive Biomedical Diagnosis by Using Light" on the Ministry of Education, Culture, Sports, Science and Technology's website.

The present inventors believe that the change in the blood flow in the skin and the change in the cerebral blood flow are both associated with the expanding and contracting action of the blood vessels or the capillary vessels and that, while focusing on the fact that the distribution of the blood vessels in the skin and the distribution of the blood vessels in the brain differ from each other, the distribution of the change in the blood flow in the skin and the distribution in the change in the blood flow in the brain are not correlated with each other. Based on this belief, the present inventors have separated an image showing a change in the blood flow in the skin and an image showing a change in the blood flow in the brain through an arithmetic operation that involves a signal reflected on the image created from a signal of the rise component of the reflection light and a signal reflected on the image created from a signal of the fall component of the reflection light. The detail of this will be described below.

The signal of the rise component and the signal of the fall component each include information on the change in the blood flow in the skin and information on the change in the cerebral blood flow at a different ratio, and this is expressed as in Logical Formula 1 below.

$$\begin{pmatrix} s0 \\ s1 \end{pmatrix} = \begin{pmatrix} a & b \\ c & d \end{pmatrix} \begin{pmatrix} Ss750 \text{ nm} \\ Sb750 \text{ nm} \end{pmatrix} \quad \text{[Math. 1]}$$

$$\begin{pmatrix} s0' \\ s1' \end{pmatrix} = \begin{pmatrix} e & f \\ g & h \end{pmatrix} \begin{pmatrix} Ss850 \text{ nm} \\ Sb850 \text{ nm} \end{pmatrix} \quad \text{[Math. 2]}$$

In the above, a, b, c, d, e, f, g, and h each denote a coefficient, Ss750 nm denotes the component of the change in the blood flow in the skin obtained when the subject is irradiated with light at a wavelength of 750 nm, Sb750 nm denotes the component of the change in the cerebral blood flow obtained when the subject is irradiated with light at a wavelength of 750 nm, Ss850 nm denotes the component of the change in the blood flow in the skin obtained when the subject is irradiated with light at a wavelength of 850 nm, and Sb850 nm denotes the component of the change in the cerebral blood flow obtained when the subject is irradiated with light at a wavelength of 850 nm. In other words, the left-hand side of each of the above formulae shows the known pixel signal value detected by the solid-state image sensor, and the right-hand sides are each unknown.

For example, provided that the rise component is composed of the component of the change in the blood flow in the skin, a=1, b=0, e=1, f=0, Ss750 nm=S0, Ss850 nm=S0' are each plugged in, c and d, g and h, and Sb750 nm and Sb850 nm are unknown. At this point, there are a number of combinations of unknowns that make the left-hand side and the right-hand side equal to each other. In this example, taking an advantage of the fact that the distribution of the change in the blood flow in the skin and the distribution of the change in the cerebral blood flow are not correlated with each other, the values of coefficients c and d, the values of coefficients g and h, and the values of Sb750 nm and Sb850 nm are extracted such that the correlation coefficient becomes closest to zero in all the pixel components of change Ss750 nm in the blood flow in the skin, change Ss850 nm in the blood flow in the skin, change Sb750 nm in the blood flow in the brain, and change Sb850 nm in the blood flow in the brain.

The signals of Ss750 nm and Sb750 nm obtained from the above indicate, respectively, the change in the blood flow in the skin and the change in the blood flow in the brain obtained when the subject is irradiated with light at a wavelength of 750 nm, and the signals of Ss850 nm and Sb850 nm indicate, respectively, the change in the blood flow in the skin and the change in the blood flow in the brain obtained when the subject is irradiated with light at a wavelength of 850 nm.

In the foregoing description, the presupposition is that the rise component is equal to the component of the change in the blood flow in the skin. However, since the rise component may include the component of the change in the cerebral blood flow slightly, a and b and e and f may be treated as variables.

In Expression 1 and Expression 2 described above, the correlativity of the distribution of the change in the blood flow in the skin and the distribution of the change in the cerebral blood flow is used. Alternatively, a multivariate analysis, such as an independent component analysis, may be used. Moreover, a, b, c, and d and e, f, g, and h that are optimal for separating the change in the blood flow in the skin and the change in the cerebral blood flow may be obtained in advance by use of a phantom having optical characteristics similar to the optical characteristics of a human.

The change in the blood flow in the skin and the change in the cerebral blood flow are each considered to change continuously over time. Therefore, the correlativity between frames are conceivably high. Thus, Ss750 nm and Sb750 nm and Ss850 nm and Sb850 nm that satisfy Expression 1 and Expression 2 may be obtained with high accuracy by obtaining the correlativity between frames and the motion vector for each pixel as well.

Performing such an arithmetic operation on the image makes it possible to separate the change in oxyhemoglobin in the blood flow in the skin and the change in deoxyhemoglobin in the blood flow in the skin from the change in oxyhemoglobin in the cerebral blood flow and the change in deoxyhemoglobin in the cerebral blood flow in the form of an image and output the resulting image, based on the component of the change in the blood flow in the skin and the component of the change in the cerebral blood flow included at a different ratio in each of the rise component and the fall component.

Two types of light at difference wavelengths are used in the present embodiment. Alternatively, three or more types of light at different wavelengths may be used.

The operation described above makes it possible to accumulate the six types of signal charges independently in the vertical transferrers in one frame period. Moreover, since the signal charges from the four photoelectric converters are added, the sensitivity increases substantially twofold as compared with a conventional method in which the signal charges from two photoelectric converters are added. Therefore, any decrease in each charge amount associated with an increase in the number of types of signal charges to be accumulated can be canceled out. This makes it possible to separate the change in the blood flow in the skin and the change in the cerebral blood flow within one frame and output the separated changes and in turn to display the result in the form of a moving image when the imaging device is operated continuously.

The above-described imaging device captures a change in the light scattered inside a subject's head. Therefore, the necessity to increase the two-dimensional resolution of the image is low. However, an extremely subtle optical detection is needed as the scattered light inside the head returns to the surface again and reaches the solid-state image sensor. Therefore, the technique that can increase the sensitivity while sacrificing the two-dimensional resolution can be said to be a very reasonable technique.

As described thus far, in the imaging device according to Embodiment 4, when the period from when the intensity of reflection light from an object starts increasing to when the increase ends is regarded as a rise period and the period from when the intensity of the reflection light from the object starts decreasing to when the decrease ends is regarded as a fall period, in the m types of exposure sequences, the exposure period of the solid-state image sensor is set so as to coincide partially with one of a first period that includes at least a part of the rise period but does not include the fall period and a second period that includes a part of the fall period but does not include the rise period.

In this configuration, the m types of exposure sequences may include an exposure sequence in which light having different irradiation wavelengths are emitted.

In this configuration, the imaging device may be an observation device that observes the inside of a light scattering body through an application of time-domain imaging, the photoelectric converters may be disposed in a matrix, the m types of exposure sequences may include first to third long wavelength sequences and first to third short wavelength sequences, the irradiation wavelength in the first to third long wavelength sequences may be longer than the irradiation wavelength in the first to third short wavelength sequences, the first long wavelength sequence and the first short wavelength sequence may each have an exposure period that is equal to the first period, the second long wavelength sequence and the second short wavelength sequence may each have an exposure period that is equal to the second period, the third long wavelength sequence and the third short wavelength sequence may each involve the exposure of background light that includes no reflection light component that is associated with the irradiation by the light source, the first to third long wavelength sequences and the first to third short wavelength sequences may be repeated a plurality of times within one frame period, the n photoelectric converters may be four of the photoelectric converters arrayed in two rows by two columns, and the imaging device may include an arithmetic operator that obtains the structure and the condition of the inside of the light scattering body through an arithmetic operation by use of each of the signal charges accumulated in the first to third long wavelength sequences and the signal charges accumulated in the first to third short wavelength sequences.

In this configuration, the irradiation by the light source may be performed in the third long wavelength sequence and the third short wavelength sequence, and the period after the reflection light has become extinct may serve as the exposure period.

In this configuration, the arithmetic operator may obtain the structure and the condition of the deep part of the light scattering body and the structure and the condition of the surface layer part of the light scattering body by use of the result from the imaging in the first to third long wavelength sequences and the result from the imaging in the first to third short wavelength sequences.

It is to be noted that the various exposure sequences in Embodiment 1 to Embodiment 4 may be combined. For example, all of or one of more of long exposure sequences L1 to L3, short exposure sequences S1 to S3, strong exposure sequences K1 and K2, weak exposure sequences J1 and J2, background exposure sequence B0, 750-nm sequences P1 to P3, and 850-nm sequences Q1 to Q3 may be combined.

Figure 26:
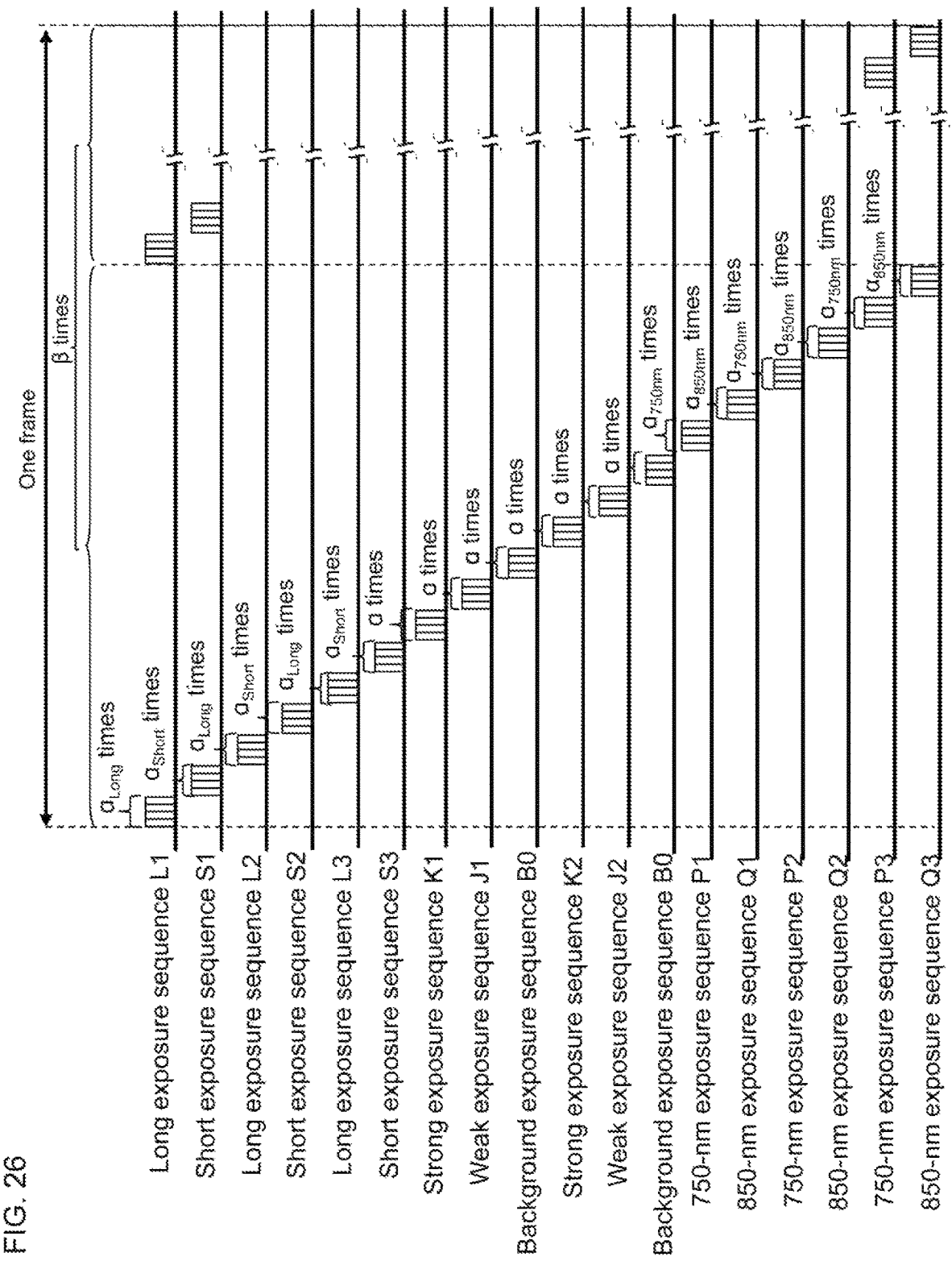
FIG. 26 is an illustration for describing an operation example in which the exposure sequences according to Embodiments 1 to 4 are combined.

FIG. 26 is an illustration for describing an operation example in which the exposure sequences according to Embodiments 1 to 4 are combined. FIG. 26 shows an operation example in which all of or one or more of long exposure sequences L1 to L3, short exposure sequences S1 to S3, strong exposure sequences K1 and K2, weak exposure sequences J1 and J2, background exposure sequence B0, 750-nm sequences P1 to P3, and 850-nm sequences Q1 to Q3 are combined.

Although only some exemplary embodiments of the present disclosure have been described in detail above, those skilled in the art will readily appreciate that many modifications are possible in the exemplary embodiments without materially departing from the novel teachings and advantages of the present disclosure. Accordingly, all such modifications are intended to be included within the scope of the present disclosure.

INDUSTRIAL APPLICABILITY

The present disclosure makes it possible to obtain a high-precision distance image with high efficiency and can thus find its use in an imaging device, or in particular in a range finding camera, for example. Moreover, the present disclosure makes it possible to obtain information on the inside of an object contactlessly with high efficiency and can thus find its use in the biometry and material analysis.

The invention claimed is:

1. An imaging device, comprising:
a light source that irradiates an object with light;
a solid-state image sensor that is exposed to reflection light from the object and accumulates the reflection light as a signal charge; and
a controller that controls irradiation by the light source and exposure of the solid-state image sensor, wherein the solid-state image sensor includes:
a plurality of photoelectric converters that convert the reflection light from the object into signal charges, each of the signal charges being the signal charge; and a plurality of charge accumulators that accumulate the signal charges, and the imaging device:
- performs, within one frame period, m types of exposure sequences for controlling the irradiation and the exposure, m being an integer greater than or equal to four;
- assigns the plurality of charge accumulators exclusively to the m types of exposure sequences;
- sets correspondence between a set of n photoelectric converters among the plurality of photoelectric converters and one charge accumulator among the plurality of charge accumulators in at least one type of exposure sequence among the m types of exposure sequences, n being an integer greater than or equal to three;
- adds the signal charges obtained from the n photoelectric converters and accumulates the signal charges added into the one charge accumulator corresponding to the n photoelectric converters; and
- changes a combination of the n photoelectric converters in every k types of exposure sequences among the m types of exposure sequences, k being an integer greater than or equal to one.

2. The imaging device according to claim 1, wherein the imaging device performs the at least one type of exposure sequence repeatedly within one frame period.

3. The imaging device according to claim 2, wherein the imaging device sets a total number of repetitions of the m types of exposure sequences based on an irradiation intensity of the light source, an irradiation time of the light source, an irradiation wavelength of the light source, and an exposure period of the solid-state image sensor.

4. The imaging device according to claim 1, wherein the m types of exposure sequences differ from each other in terms of at least one of an irradiation intensity of the light source, an irradiation time of the light source, an irradiation wavelength of the light source, or an exposure period of the solid-state image sensor.

5. The imaging device according to claim 4, wherein the imaging device is a time of flight (TOF) range finding device, and
the imaging device includes a distance calculator that calculates a distance to the object by use of the signal charges accumulated in the plurality of charge accumulators in at least two types of exposure sequences among the m types of exposure sequences.

6. The imaging device according to claim 5, wherein the m types of exposure sequences include a long exposure sequence and a short exposure sequence,
the irradiation time of the light source and the exposure period of the solid-state image sensor are each set longer in the long exposure sequence than in the short exposure sequence, and
the distance calculator calculates at least two types of distances to the object based on the m types of exposure sequences.

7. The imaging device according to claim 6, wherein the imaging device includes a distance corrector that corrects a distance calculated in the long exposure sequence by use of a distance calculated in the short exposure sequence.

8. The imaging device according to claim 6, wherein the imaging device includes an anomaly notifier that lets know of an anomaly when a difference between a part of a distance calculated in the long exposure sequence and a distance calculated in the short exposure sequence exceeds a prescribed range.

9. The imaging device according to claim 6, wherein when the exposure period in the short exposure sequence is regarded as a short exposure period,
the short exposure period is changed in every frame, and
in response to a change in the short exposure sequence in every frame, a scan is performed with a condition that a distance range calculated in the short exposure sequence overlaps a part of a distance range calculated in the long exposure sequence.

10. The imaging device according to claim 6, wherein the exposure period in the short exposure sequence is set based on a distance calculated in the long exposure sequence for a preceding frame.

11. The imaging device according to claim 1, wherein the imaging device changes, in each of frames, a combination of the n photoelectric converters from which the signal charges are obtained and added.

12. The imaging device according to claim 1, wherein m is five or six,
the plurality of photoelectric converters are disposed in a matrix,
the imaging device repeats each of the five or six types of exposure sequences a plurality of times within one frame period, and
the n photoelectric converters are a set of four photoelectric converters, among the plurality of photoelectric converters, that are arrayed in two rows by two columns.

13. The imaging device according to claim 1, wherein the imaging device is a TOF range finding device,
the plurality of photoelectric converters are disposed in a matrix,
the m types of exposure sequences include a first long exposure sequence, a second long exposure sequence, a third long exposure sequence, a first short exposure sequence, a second short exposure sequence, and a third short exposure sequence,
an irradiation time of the light source and an exposure period of the solid-state image sensor are each longer in the first long exposure sequence, the second long exposure sequence, and the third long exposure sequence than in the first short exposure sequence, the second short exposure sequence, and the third short exposure sequence,
the exposure period in the second long exposure sequence differs from the exposure period in the first long exposure sequence,
the exposure period in the second short exposure sequence differs from the exposure period in the first short exposure sequence,
the third long exposure sequence and the third short exposure sequence each involve the exposure of background light that includes no reflection light component associated with the irradiation by the light source,
the first long exposure sequence, the second long exposure sequence, the third long exposure sequence, the first short exposure sequence, the second short exposure sequence, and the third short exposure sequence are each repeated a plurality of times within one frame period,
the n photoelectric converters are four photoelectric converters, among the plurality of photoelectric converters, that are arrayed in two rows by two columns, and
the imaging device includes a distance calculator that calculates two types of distances to the object by use of the signal charges accumulated in the first long exposure sequence, the second long exposure sequence, and the third long exposure sequence and the signal charges added and accumulated in the first short exposure sequence, the second short exposure sequence, and the third short exposure sequence.

14. The imaging device according to claim 13, wherein the irradiation by the light source is performed in the third long exposure sequence and the third short exposure sequence, and a period after the reflection light has become extinct serves as the exposure period.

15. The imaging device according to claim 1, wherein
the imaging device is a TOF range finding device,
the plurality of photoelectric converters are disposed in a matrix,
the m types of exposure sequences include a first strong exposure sequence, a second strong exposure sequence, a first weak exposure sequence, a second weak exposure sequence, and a background exposure sequence,
an irradiation intensity of the light source is greater in the first strong exposure sequence and the second strong exposure sequence than in the first weak exposure sequence and the second weak exposure sequence,
an exposure period in the second strong exposure sequence differs from an exposure period in the first strong exposure sequence,
an exposure period in the second weak exposure sequence differs from an exposure period in the first weak exposure sequence,
the background exposure sequence involves the exposure of background light that does not include the reflection light,
the first strong exposure sequence, the second strong exposure sequence, the first weak exposure sequence, the second weak exposure sequence, and the background exposure sequence are each repeated a plurality of times within one frame period,
the n photoelectric converters are four photoelectric converters, among the plurality of photoelectric converters, that are arrayed in two rows by two columns, and
the imaging device includes a distance calculator that, for every set of the n photoelectric converters, calculates a distance by use of the signal charges in the background exposure sequence and one of the signal charges in the first strong exposure sequence and the second strong exposure sequence and the signal charges in the first weak exposure sequence and the second weak exposure sequence.

16. The imaging device according to claim 1, wherein
when a period from when an intensity of the reflection light from the object starts increasing to when the intensity stops increasing is regarded as a rise period and a period from when the intensity of the reflection light from the object starts decreasing to when the intensity stops decreasing is regarded as a fall period, in the m types of exposure sequences, an exposure period of the solid-state image sensor is set so as to coincide with one of a first period that includes at least a part of the rise period but does not include the fall period and a second period that includes a part of the fall period but does not include the rise period.

17. The imaging device according to claim 16, wherein
the m types of exposure sequences include an exposure sequence in which the object is irradiated with light having different irradiation wavelengths.

18. The imaging device according to claim 16, wherein
the imaging device is an observation device that observes an inside of a light scattering body through an application of time-domain imaging,
the plurality of photoelectric converters are disposed in a matrix,
the m types of exposure sequences include a first long wavelength sequence, a second long wavelength sequence, a third long wavelength sequence, a first short wavelength sequence, a second short wavelength sequence, and a third short wavelength sequence,
an irradiation wavelength is longer in the first long wavelength sequence, the second long wavelength sequence, and the third long wavelength sequence than in the first short wavelength sequence, the second short wavelength sequence, and the third short wavelength sequence,
the exposure period in each of the first long wavelength sequence and the first short wavelength sequence is equal to the first period,
the exposure period in each of the second long wavelength sequence and the second short wavelength sequence is equal to the second period,
the third long wavelength sequence and the third short wavelength sequence each involve the exposure of background light that includes no reflection light component associated with the irradiation by the light source,
the first long wavelength sequence, the second long wavelength sequence, the third long wavelength sequence, the first short wavelength sequence, the second short wavelength sequence, and the third short wavelength sequence are each repeated a plurality of times within one frame period,
the n photoelectric converters are four photoelectric converters, among the plurality of photoelectric converters, that are arrayed in two rows by two columns, and
the imaging device includes an arithmetic operator that obtains a structure and a condition of the inside of the light scattering body through an arithmetic operation by use of each of the signal charges accumulated in the first long wavelength sequence, the second long wavelength sequence, and the third long wavelength sequence and the signal charges accumulated in the first short wavelength sequence, the second short wavelength sequence, and the third short wavelength sequence.

19. The imaging device according to claim 18, wherein
The irradiation by the light source is performed in the third long wavelength sequence and the third short wavelength sequence, and a period after the reflection light has become extinct serves as the exposure period.

20. The imaging device according to claim 18, wherein
the arithmetic operator obtains the structure and the condition of a deep part of the light scattering body and the structure and the condition of a surface layer part of the light scattering body by use of a result from imaging in the first long wavelength sequence, the second long wavelength sequence, and the third long wavelength sequence and a result from imaging in the first short wavelength sequence, the second short wavelength sequence, and the third short wavelength sequence.

* * * * *